US011666082B2

(12) United States Patent
Lu et al.

(10) Patent No.: US 11,666,082 B2
(45) Date of Patent: Jun. 6, 2023

(54) REDUCING TOBACCO SPECIFIC NITROSAMINES THROUGH ALTERATION OF THE NITRATE ASSIMILATION PATHWAY

(71) Applicants: PHILIP MORRIS PRODUCTS S.A., Neuchatel (CH); NORTH CAROLINA STATE UNIVERSITY, Raleigh, NC (US)

(72) Inventors: Jianli Lu, Cary, NC (US); Ramsey S. Lewis, Apex, NC (US); Ralph Dewey, Apex, NC (US); Lucien Bovet, La Chaux-de-Fonds (CH)

(73) Assignees: Philip Morris Products S.A., Neuchatel (CH); North Carolina State University, Raleigh, NC (US)

( * ) Notice: Subject to any disclaimer, the term of this patent is extended or adjusted under 35 U.S.C. 154(b) by 625 days.

(21) Appl. No.: 15/513,229

(22) PCT Filed: Sep. 23, 2015

(86) PCT No.: PCT/EP2015/071919
§ 371 (c)(1),
(2) Date: Mar. 22, 2017

(87) PCT Pub. No.: WO2016/046288
PCT Pub. Date: Mar. 31, 2016

(65) Prior Publication Data
US 2017/0303582 A1 Oct. 26, 2017

(30) Foreign Application Priority Data

Sep. 26, 2014 (EP) .................................... 14186705
Nov. 25, 2014 (EP) .................................... 14194798

(51) Int. Cl.
| | | |
|---|---|---|
| *C12N 15/00* | (2006.01) | |
| *A24B 15/24* | (2006.01) | |
| *C12N 9/00* | (2006.01) | |
| *C12N 9/06* | (2006.01) | |
| *C12N 15/82* | (2006.01) | |

(52) U.S. Cl.
CPC ............ *A24B 15/245* (2013.01); *A24B 15/24* (2013.01); *C12N 9/0044* (2013.01); *C12N 15/8243* (2013.01); *C12Y 107/01001* (2013.01); *C12Y 107/01002* (2013.01); *C12Y 107/01003* (2013.01); *C12N 15/00* (2013.01); *C12Y 107/00* (2013.01)

(58) Field of Classification Search
None
See application file for complete search history.

(56) References Cited

U.S. PATENT DOCUMENTS

| | | |
|---|---|---|
| 4,945,050 A | 7/1990 | Sanford |
| 5,563,055 A | 10/1996 | Townsend |
| 5,879,918 A | 3/1999 | Tomes |
| 5,886,244 A | 3/1999 | Tomes |
| 5,932,782 A | 8/1999 | Bidney |
| 5,981,840 A | 11/1999 | Zhao |
| 9,247,706 B2 | 2/2016 | Dewey |
| 2009/0205072 A1* | 8/2009 | Dewey ............... C12N 15/8243 800/278 |
| 2012/0216822 A1 | 8/2012 | Lewis |

FOREIGN PATENT DOCUMENTS

| | | |
|---|---|---|
| CN | 102858983 A | 8/2015 |
| RU | 2324737 | 5/2008 |
| WO | WO 2008/070274 | 6/2008 |
| WO | WO 2013/140155 | 9/2013 |

OTHER PUBLICATIONS

Lea et al., 2006, Plant Physiology 140: 1085-104.*
Predicted nitrate reductase [NADH] 2 from Nicotiana sylvestris, NCBI/GenBank accession No. XP_009758007, version XP_009758007.1, published on Oct. 21, 2014.*
Nitrate reductase from Nicotiana tabacum, NCBI/GenBank accession No. CAA32217, version CAA32217.1, published on Nov. 14, 2006.*
Lillo et al., 2004, Mechanism and importance of post-translational regulation of nitrate reductase, J. Exp. Bot. 55: 1275-1282.*
Morozkina and Zvyagilskaya, 2007, Nitrate reductases: structure, functions, and effect of stress factors, Biochemistry (Mosc). 72(10): 1151-1160.*
Office Action issued in China for Application No. 201580049814.7 dated Jan. 26, 2018 (34 pages). English translation included.
PCT International Search Report and Written Opinion for PCT/EP2015/071919 dated Nov. 25, 2015 (13 pages).
Lea et al., "Posttranslational Regulation of Nitrate Reductase Strongly Affects the Levels of Free Amino Acids and Nitrate, Whereas Transcriptional Regulation Has Only Minor Influence", *Plant Physiology*, vol. 140, No. 3, Mar. 2006, pp. 1085-1094.
Lewis et al., "Three Nicotine Demethylase Genes Mediate Nornicotine Biosynthesis in *Nicotiana tabacum* L.: Functional Characterization of the CYP82E10 Gene", *Phytochemistry*, vol. 71, No. 17-18, Dec. 1, 2010, pp. 1988-1998.
Nussaume et al., "Post-Transcriptional Regulation of Nitrate Reductase by Light is Abolished by an N-Terminal Deletion", *The Plant Cell*, vol. 7, No. 5, 1995, pp. 611-621.
International Preliminary Report on Patentability dated Apr. 18, 2017 (4 pages).
GenBank Accession No. 77944 (replaced by P07166.1).
Ausubel et al., Current Protocols in Molecular Biology, vols. 1-3, John Wiley & Sons, Inc., Hoboken, N.J. (1993).

(Continued)

*Primary Examiner* — Weihua Fan
(74) *Attorney, Agent, or Firm* — Mueting Raasch Group

(57) ABSTRACT

Provided are modified tobacco plants having reduced nitrate levels and tobacco products generated from the modified tobacco plants having reduced tobacco specific nitrosamines (TSNAs). Also provided are methods of reducing TSNAs in tobacco products by altering the gene expression of the nitrate assimilation pathway

21 Claims, 16 Drawing Sheets

Specification includes a Sequence Listing.

(56) References Cited

OTHER PUBLICATIONS

Chakrabarti et al., "CYP82E4-Mediated Nicotine to Nornicotine Conversion in Tobacco is Regulated by a Senescence-Specific Signaling Pathway", *Plant Mol. Biol.* 66:415-427 (2008).

Chen et al., "Complete Sequence of the Binary Vector pBI121 and its Application in Cloning T-DNA Insertion from Transgenic Plants", *Mol. Breed.* 11:287-293 (2003).

Crossway et al., "Micromanipulation Techniques in Plant Biotechnology", *Biotechniques* 4:320-334 (1986).

Crutchfield and Grove, "A New Cadmium Reduction Device for the Microplate Determination of Nitrate in Water, Soil, Plant Tissue, and Physiological Fluids," *J. AOAC International* 94:1898-1905 (2011).

Dubois et al., "Localization of Tobacco Cytosolic Glutamine Synthetase Enzymes and the Corresponding Transcripts Shows Organ- and Cell-Specific Patterns of Protein Synthesis and Gene Express", *Plant Mol. Biol.* 31:803-817 (1996).

Lancien et al., "*Arabidopsis* glt1-T Mutant Defines a Role for NADH-GOGAT in the Non-Photorespiratory Ammonium Assimilatory Pathway," *Plant Journal* 29:347-358 (2002).

Lewis et al., "Three Nicotine Demethylase Genes Mediate Nornicotine Biosynthesis in *Nicotiana tabacum* L.: Functional Characterization of the CYP82E10 Gene", *Phytochem.* 71:1988-1998 (2010).

Lillo et al., "Mutation of the Regulatory Phosphorylation Site of Tobacco Nitrate and Reductase Results in Constitutive Activation of the Enzyme in Vivo and Nitrate Accumulation", *Plant Journal* 35:566-573 (2003).

McCabe et al., "Stable Transformation of Soybean (*Clycine max*) by Particle Acceleration", *Biotechnology* 6:923-926 (1988).

Morgan et al., A Collaborative Study for the Determination of Tobacco Specific Nitrosamines in Tobacco, *Beit. Tabakforschung* 23:192-203 (2004).

Paszkowski et al., "Direct Gene Transfer to Plants", *EMBO J.* 3:2717-2722 (1984).

Perbal, A Practical Guide to Molecular Cloning, 2nd edition, John Wiley & Sons, New York, N.Y. (1988).

Riggs et al., "Stable Transformation of Tobacco by Electroporation: Evidence for Plasmid Concatenation", *Proc. Natl. Acad. Sci. USA* 83:5602-5606 (1986).

Tomes et al., "Direct DNA Transfer into Intact Plant Cells via Microprojectile Bombardment", *Plant Cell, Tissue, and Organ Culture*: Fundamental Methods, ed. Gamborg and Phillips (Springer-Verlag, Berlin) (1995).

Vaucheret et al., "Complete Nucleotide Sequence of the Two Homeologous Tobacco Nitrate Reductase Genes", Plant Mol. Biol. 12:597-200 (1989).

Luo Yunbo edited, "Introduction to Food Biotechnology", China Agricultural University Press, the $2^{nd}$ Edition, Aug. 30, 2011.

Jin Pinzhgeng et al., edited, "Safety and Hazard Prevention of Cigarette Smoke", China Light Industry Press, the $1^{st}$ Edition in Sep. 2009, p. 147.

Getu Beyene et al., Two New Cysteine Proteinases with Specific Expression Patterns in Mature and Senescent Tobacco (*Nicotiana tabacum* L.) leaves, Journal of Experimental Botany, 2006, vol. 57, No. 6, pp. 1431-1443 (abstract).

Office Action issued in Russia for Application No. 2017114356 dated Apr. 29, 2019 (15 pages). English translation included.

Office Action issued in China for Application No. 201580049814.7 dated Jun. 19, 2019 (26 pages). English translation included.

Lillo et al., "Mechanism and Importance of Post-Translational Regulation of Nitrate Reductase", Journal of Experimental Botany, vol. 55, No. 401, pp. 1275-1282, Jun. 2004.

UniProt Database, Vaucheret H et al., "Nitrate Reductase Enzyme (NADH) 2", Oct. 16, 2013, pp. 1-5.

Office Action issued in China for Application No. 201580049814.7 dated Jun. 17, 2021 (13 page). English translation included.

* cited by examiner

| Plants | Gene | Residues | Sequence |
|---|---|---|---|
| Tomato | NIA | 523 - 533 | L K K S I S T P F M N |
| Tobacco | NIA1 | 518 - 528 | L K K S I S T P F M N |
| Tobacco | NIA2 | 518 - 528 | L K K S I S T P F M N |
| Petunia | NIA | 522 - 532 | L K K S I S T P F M N |
| Squash | NIA | 530 - 540 | L K K S V S T P F M N |
| Birch | NIA1 | 515 - 525 | L K K S V S T P F M N |
| Arabidopsis | NIA1 | 532 - 542 | L K K S V S S P F M N |
| Arabidopsis | NIA2 | 529 - 539 | L K K S V S T P F M N |
| Rape | NIA1 | 526 - 536 | L K K S V S S P F M N |
| Rape | NIA2 | 526 - 536 | L K K S V S T P F M N |
| Soybean | NIA2 | 504 - 514 | L K K S V S S P F M N |
| Kidney bean | NIA1 | 502 - 512 | L K K S V S T P F M N |
| Kidney bean | NIA2 | 500 - 510 | L K K S V S S P F M N |
| *Lotus japonicus* | NIA | 508 - 518 | L K K S V S S P F M N |
| Cichorium | NIA1 | 521 - 531 | L K K S V S S P F M N |
| Maize | NIA1 | 234 - 244 | L K R S T S T P F M N |
| Barley | NIA1 | 524 - 534 | L K R S T S T P F M N |
| Barley | NIA2 | 521 - 531 | L K R S T S T P F M N |
| Rice | NIA1 | 527 - 537 | L K R S T S T P F M N |
| Spinach | NIA | 538 - 548 | L K R T A S T P F M N |

FIG. 2

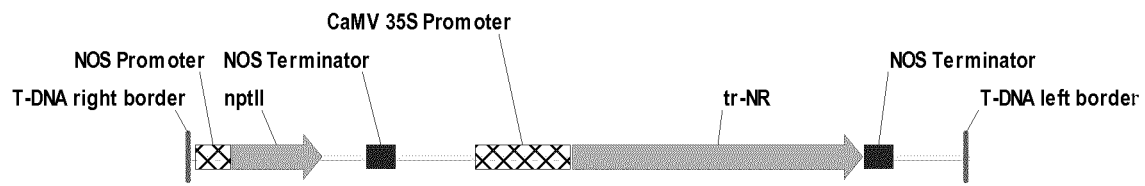
35S:tr-NR (6864 bp)
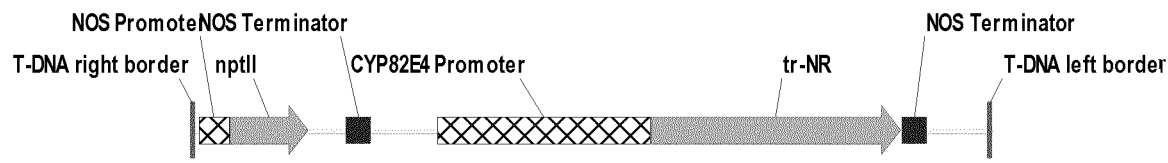
E4:tr-NR (8166 bp)
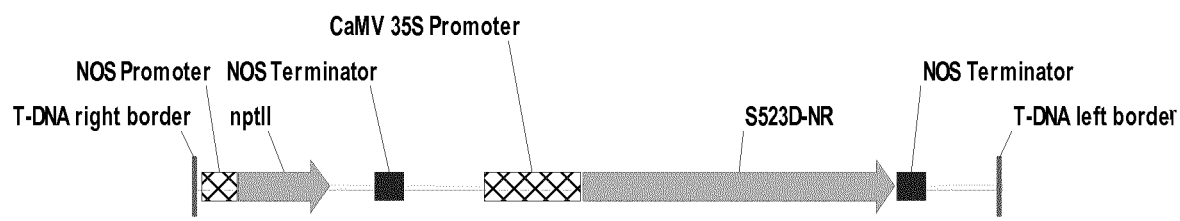
35S:S523D-NR (7032 bp)
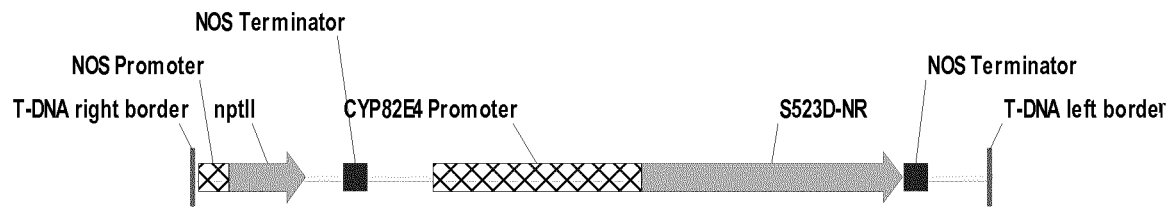
E4:S523D-NR (8334 bp)
FIG. 3B

SEQUENCE LISTING

```
<160> NUMBER OF SEQ ID NOS: 28

<210> SEQ ID NO 1
<211> LENGTH: 2715
<212> TYPE: DNA
<213> ORGANISM: Artificial Sequence
<220> FEATURE:
<223> OTHER INFORMATION: Synthetic Oligonucleotide

<400> SEQUENCE: 1
atggcggcat ctgtcgaaaa caggcagttc agtcacatag aagccggttt atcccggtct     60
ttcaagcctc ggtctgattc cccggttcgt ggctgcaact tccctccgcc caacagtact    120
aatttccaaa agaaaccaaa ttccaccatt ttccttgatt actcgtcgag tgaagacgac    180
gatgatgatg acgaaaaaaa tgagtacctt caaatgatca aaaaagggaa ttcagaatta    240
gagccatctg ttcatgacag cagggacgaa ggtaccgctg ataactggat tgaacgcaac    300
ttttccttga ttcgtctcac cggaaagcat ccatttaact ccgaaccgcc gttgaaccgt    360
ctcatgcacc acggttttat cacaccggtc ccacttcatt acgttcgtaa ccatggaccg    420
gttcccaagg gcacatggga tgactggacc gtggaagtca cgggactagt gaaacgtcct    480
atgaaattca aatggacca gttggttaac gaattccctt ccagagaatt gcccgttacg    540
cttgtgtgtg ctggcaaccg aaggaaagaa cagaacatgt taaacaaac cattggtttc    600 aactggggtg ccgctgccgt ttcaacaact gtatggcgcg gggtacccct acgcgctttg    660
ttaaaacggt acggtgtttt tagcaagaat aaagggcgc ttaatgtttg cttcgaagga    720
gctgatgtct tgcccggagg cggtggttca aagtatggaa ccagcattaa gaaggaattt    780
gcaatggatc cagcacgaga tatcataata gcttacatgc agaacggaga aaaattggca    840
cccgaccacg ggttctccagt acgaatgata attccaggat tcattggagg aagaatggtg    900
aaatggataa agaggattat agtcaccacc caagaatcag acagctatta tcatttcaag    960
```

|  |  |  |  |  |  |
|---|---|---|---|---|---|
| gacaatagag | ttcttcctcc | ccatgttgat | gctgaacttg | caaatactga | agcatggtgg | 1020 |
| tacaagccag | agtacatcat | caatgagctc | aatattaact | ctgtcattac | gacgccgtgt | 1080 |
| catgaagaaa | ttttgcctat | aacgcctgg | acgactcagc | gaccttacac | gttgaggggc | 1140 |
| tattcttatt | ctggcggagg | gaaaaaagta | acgcgagtag | aagtgacctt | ggatggagga | 1200 |
| gaaacatggc | aagtttgcac | actagatcac | ccagagaagc | ccaccaaata | tggcaagtac | 1260 |
| tggtgttggt | gcttttggtc | actcgaggtt | gaggtgttag | acttgctcag | tgccaaagaa | 1320 |
| attgctgttc | gagcttggga | tgagaccctc | aatactcaac | ctgagaagct | tatttggaat | 1380 |
| gtcatgggaa | tgatgaacaa | ttgctggttc | cgagtaaaga | tgaatgtgtg | caagcctcac | 1440 |
| aagggagaga | ttggaatagt | gtttgaacac | ccgactcaac | ctggaaacca | atcaggtgga | 1500 |
| tggatggcaa | aggagaggca | tttggagata | tcagcagagg | cacctccaac | actaaagaag | 1560 |
| agtatctcaa | ctccattcat | gaacacagct | tccaagatgt | actccatgtc | ggaggtgagg | 1620 |
| aaacacagct | ctgctgactc | tgcttggatc | atagtccatg | gtcatatcta | tgacgccacg | 1680 |
| cgtttcttga | aagatcaccc | cggtggttct | gacagcattc | tcatcaatgc | tggcactgat | 1740 |
| tgcactgagg | aatttgatgc | aattcattct | gataaggcta | agaagctatt | ggaggaattc | 1800 |
| aggattggtg | aactcctaac | tactggttac | acctctgact | ctcctggcaa | ctccgtccat | 1860 |
| ggatcttctt | ccttcagcag | ctttctagca | cctattaagg | aacttgttcc | agcgcagagg | 1920 |
| agtgtggccc | tcattccaag | agagaaaatc | ccatgcaaac | tcatcgacaa | caatccatc | 1980 |
| tcccctgatg | ttaggaaatt | tcgatttgca | ttgccctctg | aggatcaagt | cttgggcttg | 2040 |
| cctgttggta | aacacatctt | cctctgtgcc | gttattgacg | ataagctctg | catgcgcgcc | 2100 |
| tacacgccta | ctagcacgat | cgatgaggtg | gggtacttcg | agttggttgt | caagatatac | 2160 |
| ttcaaaggaa | ttcaccctaa | attccccaat | gggggggcaaa | tgtcacaata | ccttgattct | 2220 |
| ctccaattag | ggtcatttct | cgacgtgaaa | ggtccattag | gtcacattga | ataccaagga | 2280 |
| aagggcaatt | tcttagttca | tggcaaacaa | aagtttgcca | agaagttggc | catgatagca | 2340 |
| ggtggaacag | ggataactcc | agtttatcaa | gtcatgcagg | caattctgaa | agatccagaa | 2400 |
| gatgacacag | aaatgtatgt | ggtctatgct | aatagaacag | aggatgatat | tttacttaag | 2460 |
| gaagagcttg | attcatgggc | tgagaaaatt | ccagaaaggg | ttaaagtttg | gtatgtggtt | 2520 |
| caagattcta | ttaaagaagg | atggaagtac | agccttggtt | ttatttcaga | agccatttg | 2580 |
| agagaacata | tccctgagcc | atctcacaca | acactggctt | tggcttgtgg | accacctcct | 2640 |
| atgattcaat | ttgctgttaa | tccaaacttg | gagaagatgg | gctatgacat | taaggattcc | 2700 |
| ttattggtgt | tctaa |  |  |  |  | 2715 |

<210> SEQ ID NO 2
<211> LENGTH: 904
<212> TYPE: PRT
<213> ORGANISM: Artificial Sequence
<220> FEATURE:
<223> OTHER INFORMATION: Synthetic Peptide

<400> SEQUENCE: 2

Met Ala Ala Ser Val Glu Asn Arg Gln Phe Ser His Ile Glu Ala Gly
1               5                   10                  15

Leu Ser Arg Ser Phe Lys Pro Arg Ser Asp Ser Pro Val Arg Gly Cys
                20                  25                  30

Asn Phe Pro Pro Pro Asn Ser Thr Asn Phe Gln Lys Lys Pro Asn Ser
            35                  40                  45

```
Thr Ile Phe Leu Asp Tyr Ser Ser Glu Asp Asp Asp Asp Asp
    50              55              60
Glu Lys Asn Glu Tyr Leu Gln Met Ile Lys Lys Gly Asn Ser Glu Leu
65              70              75              80
Glu Pro Ser Val His Asp Ser Arg Asp Glu Gly Thr Ala Asp Asn Trp
                85              90              95
Ile Glu Arg Asn Phe Ser Leu Ile Arg Leu Thr Gly Lys His Pro Phe
            100             105             110
Asn Ser Glu Pro Pro Leu Asn Arg Leu Met His His Gly Phe Ile Thr
        115             120             125
Pro Val Pro Leu His Tyr Val Arg Asn His Gly Pro Val Pro Lys Gly
    130             135             140
Thr Trp Asp Asp Trp Thr Val Glu Val Thr Gly Leu Val Lys Arg Pro
145             150             155             160
Met Lys Phe Thr Met Asp Gln Leu Val Asn Glu Phe Pro Ser Arg Glu
                165             170             175
Leu Pro Val Thr Leu Val Cys Ala Gly Asn Arg Arg Lys Glu Gln Asn
            180             185             190
Met Val Lys Gln Thr Ile Gly Phe Asn Trp Gly Ala Ala Val Ser
        195             200             205
Thr Thr Val Trp Arg Gly Val Pro Leu Arg Ala Leu Leu Lys Arg Tyr
    210             215             220
Gly Val Phe Ser Lys Asn Lys Gly Ala Leu Asn Val Cys Phe Glu Gly
225             230             235             240
Ala Asp Val Leu Pro Gly Gly Gly Ser Lys Tyr Gly Thr Ser Ile
                245             250             255
Lys Lys Glu Phe Ala Met Asp Pro Ala Arg Asp Ile Ile Ala Tyr
            260             265             270
Met Gln Asn Gly Glu Lys Leu Ala Pro Asp His Gly Phe Pro Val Arg
        275             280             285
Met Ile Ile Pro Gly Phe Ile Gly Gly Arg Met Val Lys Trp Ile Lys
    290             295             300
Arg Ile Ile Val Thr Thr Gln Glu Ser Asp Ser Tyr Tyr His Phe Lys
305             310             315             320
Asp Asn Arg Val Leu Pro Pro His Val Asp Ala Glu Leu Ala Asn Thr
                325             330             335
Glu Ala Trp Trp Tyr Lys Pro Glu Tyr Ile Ile Asn Glu Leu Asn Ile
            340             345             350
Asn Ser Val Ile Thr Thr Pro Cys His Glu Glu Ile Leu Pro Ile Asn
        355             360             365
Ala Trp Thr Thr Gln Arg Pro Tyr Thr Leu Arg Gly Tyr Ser Tyr Ser
    370             375             380
Gly Gly Gly Lys Lys Val Thr Arg Val Glu Val Thr Leu Asp Gly Gly
385             390             395             400
Glu Thr Trp Gln Val Cys Thr Leu Asp His Pro Glu Lys Pro Thr Lys
                405             410             415
Tyr Gly Lys Tyr Trp Cys Trp Cys Phe Trp Ser Leu Glu Val Glu Val
            420             425             430
Leu Asp Leu Leu Ser Ala Lys Glu Ile Ala Val Arg Ala Trp Asp Glu
        435             440             445
Thr Leu Asn Thr Gln Pro Glu Lys Leu Ile Trp Asn Val Met Gly Met
    450             455             460
Met Asn Asn Cys Trp Phe Arg Val Lys Met Asn Val Cys Lys Pro His
```

-continued

```
              465                 470                 475                 480
Lys Gly Glu Ile Gly Ile Val Phe Glu His Pro Thr Gln Pro Gly Asn
                        485                 490                 495
Gln Ser Gly Gly Trp Met Ala Lys Glu Arg His Leu Glu Ile Ser Ala
                500                 505                 510
Glu Ala Pro Pro Thr Leu Lys Lys Ser Ile Ser Thr Pro Phe Met Asn
                515                 520                 525
Thr Ala Ser Lys Met Tyr Ser Met Ser Glu Val Arg Lys His Ser Ser
        530                 535                 540
Ala Asp Ser Ala Trp Ile Ile Val His Gly His Ile Tyr Asp Ala Thr
545                 550                 555                 560
Arg Phe Leu Lys Asp His Pro Gly Gly Ser Asp Ser Ile Leu Ile Asn
                565                 570                 575
Ala Gly Thr Asp Cys Thr Glu Glu Phe Asp Ala Ile His Ser Asp Lys
                580                 585                 590
Ala Lys Lys Leu Leu Glu Glu Phe Arg Ile Gly Glu Leu Leu Thr Thr
        595                 600                 605
Gly Tyr Thr Ser Asp Ser Pro Gly Asn Ser Val His Gly Ser Ser Ser
        610                 615                 620
Phe Ser Ser Phe Leu Ala Pro Ile Lys Glu Leu Val Pro Ala Gln Arg
625                 630                 635                 640
Ser Val Ala Leu Ile Pro Arg Glu Lys Ile Pro Cys Lys Leu Ile Asp
                645                 650                 655
Lys Gln Ser Ile Ser Pro Asp Val Arg Lys Phe Arg Phe Ala Leu Pro
                660                 665                 670
Ser Glu Asp Gln Val Leu Gly Leu Pro Val Gly Lys His Ile Phe Leu
        675                 680                 685
Cys Ala Val Ile Asp Asp Lys Leu Cys Met Arg Ala Tyr Thr Pro Thr
        690                 695                 700
Ser Thr Ile Asp Glu Val Gly Tyr Phe Glu Leu Val Val Lys Ile Tyr
705                 710                 715                 720
Phe Lys Gly Ile His Pro Lys Phe Pro Asn Gly Gly Gln Met Ser Gln
                725                 730                 735
Tyr Leu Asp Ser Leu Gln Leu Gly Ser Phe Leu Asp Val Lys Gly Pro
                740                 745                 750
Leu Gly His Ile Glu Tyr Gln Gly Lys Gly Asn Phe Leu Val His Gly
        755                 760                 765
Lys Gln Lys Phe Ala Lys Lys Leu Ala Met Ile Ala Gly Gly Thr Gly
        770                 775                 780
Ile Thr Pro Val Tyr Gln Val Met Gln Ala Ile Leu Lys Asp Pro Glu
785                 790                 795                 800
Asp Asp Thr Glu Met Tyr Val Val Tyr Ala Asn Arg Thr Glu Asp Asp
                805                 810                 815
Ile Leu Leu Lys Glu Glu Leu Asp Ser Trp Ala Glu Lys Ile Pro Glu
                820                 825                 830
Arg Val Lys Val Trp Tyr Val Gln Asp Ser Ile Lys Glu Gly Trp
        835                 840                 845
Lys Tyr Ser Leu Gly Phe Ile Ser Glu Ala Ile Leu Arg Glu His Ile
        850                 855                 860
Pro Glu Pro Ser His Thr Thr Leu Ala Leu Ala Cys Gly Pro Pro Pro
865                 870                 875                 880
Met Ile Gln Phe Ala Val Asn Pro Asn Leu Glu Lys Met Gly Tyr Asp
                885                 890                 895
```

Ile Lys Asp Ser Leu Leu Val Phe
              900

<210> SEQ ID NO 3
<211> LENGTH: 2715
<212> TYPE: DNA
<213> ORGANISM: Artificial Sequence
<220> FEATURE:
<223> OTHER INFORMATION: Synthetic Oligonucleotide

<400> SEQUENCE: 3

| | | | | | |
|---|---|---|---|---|---|
| atggcggcat | ctgtcgaaaa | caggcagttc | agtcacctag | aagccggttt | atcccggtct | 60 |
| ttcaagcccc | ggtctgattc | cccggttcgt | ggctgcaact | tcccttcgcc | caacagtact | 120 |
| aatttccaaa | agaaaccaaa | ttccaccatt | taccttgatt | actcgtcgag | tgaagacgac | 180 |
| gatgatgatg | acgaaaaaaa | tgagtacctt | caaatgatta | aaaaagggaa | ttcagagtta | 240 |
| gagccatctg | ttcatgacac | tagggacgaa | ggtaccgctg | ataattggat | tgaacgcaac | 300 |
| ttttccatga | ttcgtctcac | cggaaagcat | ccatttaact | ccgaaccacc | gttgaaccgg | 360 |
| ctcatgcacc | acggctttat | cacaccggtc | ccacttcatt | acgttcgtaa | ccatggaccg | 420 |
| gttcccaagg | gcacgtggga | tgactggacc | gtggaagtca | cgggactagt | gaagcgtcct | 480 |
| atgaaattca | caatggacca | gttggttaac | gaattccctt | gtagagaatt | gcccgttacg | 540 |
| cttgtttgtg | ctggcaatcg | aaggaaagaa | cagaacatgg | ttaaacaaac | cattggtttc | 600 |
| aactggggcg | ccgctgccgt | ttcaacaacg | atatggcgcg | gggtaccct | ccgcgctttg | 660 |
| ctaaaacggt | gcggtgtttt | tagcaagaat | aaggggcgc | ttaatgtttg | cttcgaagga | 720 |
| gctgatgtgt | tgcccggagg | tggtggttca | agtatggaa | ccagcattaa | gaaggaattt | 780 |
| gcaatggatc | cagcacgaga | tatcatcgta | gcctacatgc | agaacggaga | aaaattggca | 840 |
| cccgaccacg | ggtttccagt | acgaatgata | attccaggat | tcattggagg | aagaatggtg | 900 |
| aaatggataa | agaggattat | agtcaccacc | caagaatcag | acagctatta | tcatttcaag | 960 |
| gacaatagag | ttcttcctcc | ccatgttgat | gctgaacttg | caaataccga | agcatggtgg | 1020 |
| tacaagccag | agtatatcat | caatgagctt | aatattaact | ctgtcattac | gacgccgtgt | 1080 |
| catgaagaaa | ttttgccaat | taacgcctgg | acgactcagc | gaccttacac | gttgaggggc | 1140 |
| tattcttatt | ctggcggagg | gaaaaaagta | acgcgagtag | aagtgacgtt | ggatggagga | 1200 |
| gaaacatggc | aagttagcac | actagatcac | ccagagaagc | ccaccaaata | tggcaagtac | 1260 |
| tggtgttggt | gcttttggtc | actcgaggtt | gaggtgttag | acttgctcag | tgctaaagaa | 1320 |
| attgctgttc | gagcttggga | tgagaccctc | aatactcaac | ccgagaagct | tatttggaac | 1380 |
| gtcatgggaa | tgatgaataa | ttgctggttc | cgagtaaaga | tgaatgtgtg | caagcctcac | 1440 |
| aagggagaga | ttggaatagt | gtttgagcat | ccgactcaac | ctggaaacca | atcaggtgga | 1500 |
| tggatggcga | aggagagaca | tttggagata | tcagcagagg | cacctcaaac | actaagaag | 1560 |
| agtatctcaa | ctccattcat | gaacacagct | tccaagatgt | actccatgtc | cgaggtcagg | 1620 |
| aaacacagct | ctgctgactc | tgcttggatc | atagtccatg | gtcatatcta | tgacgccacg | 1680 |
| cgtttcttga | agatcacccc | tggtgggact | gacagcattc | tcatcaatgc | tggcactgat | 1740 |
| tgcactgagg | aatttgatgc | aattcattct | gataaggcta | agaagctctt | ggaggatttc | 1800 |
| aggattggtg | aactcataac | tactggttac | acctctgact | ctcctggcaa | ctccgtgcac | 1860 |
| ggatcttctt | ccttcagcag | ctttctagca | cctattaagg | aacttgttcc | agcgcagagg | 1920 |
| agtgtggccc | taattccaag | agagaaaatc | ccatgcaaac | tcatcgacaa | gcaatccatc | 1980 |

```
tcccatgatg ttaggaaatt tcgatttgca ttgccctctg aggatcaagt cttgggcttg    2040
cctgttggaa acatatctt cctctgtgcc gttattgacg ataagctctg catgcgcgct     2100
tacacgccta ctagcacgat cgatgaggtg gggtacttcg agttggttgt caagatatac    2160
ttcaaaggaa ttcaccctaa attccccaat ggagggcaaa tgtcacagta tcttgattct    2220
atgccgttag ggtcatttct cgacgtgaaa ggtccattag gtcacattga ataccaagga    2280
aagggaaatt tcttagttca tggcaaacag aagtttgcca agaagttggc catgatagca    2340
ggtggaacag gaataactcc agtgtatcaa gtcatgcagg caattctgaa agatccagaa    2400
gatgacacag aaatgtatgt ggtgtatgct aacagaacag aggatgatat tttacttaag    2460
gaagagcttg attcatgggc tgagaaaatt ccagagaggg ttaaagtttg gtatgtggtt    2520
caggattcta ttaaagaagg atggaagtac agcattggtt ttattacaga agccattttg    2580
agagaacata tccctgagcc atctcacaca cactggcttt ggcttgtgg accacctcct     2640 atgattcaat tgctgttaa tccaaacttg gagaagatgg gctatgacat taaggattcc     2700
ttattggtgt tctaa                                                     2715

<210> SEQ ID NO 4
<211> LENGTH: 904
<212> TYPE: PRT
<213> ORGANISM: Artificial Sequence
<220> FEATURE:
<223> OTHER INFORMATION: Synthetic Peptide

<400> SEQUENCE: 4

Met Ala Ala Ser Val Glu Asn Arg Gln Phe Ser His Leu Glu Ala Gly
1               5                   10                  15

Leu Ser Arg Ser Phe Lys Pro Arg Ser Asp Ser Pro Val Arg Gly Cys
            20                  25                  30

Asn Phe Pro Ser Pro Asn Ser Thr Asn Phe Gln Lys Lys Pro Asn Ser
        35                  40                  45

Thr Ile Tyr Leu Asp Tyr Ser Ser Ser Glu Asp Asp Asp Asp Asp
    50                  55                  60

Glu Lys Asn Glu Tyr Leu Gln Met Ile Lys Lys Gly Asn Ser Glu Leu
65                  70                  75                  80

Glu Pro Ser Val His Asp Thr Arg Asp Glu Gly Thr Ala Asp Asn Trp
                85                  90                  95

Ile Glu Arg Asn Phe Ser Met Ile Arg Leu Thr Gly Lys His Pro Phe
            100                 105                 110

Asn Ser Glu Pro Pro Leu Asn Arg Leu Met His His Gly Phe Ile Thr
        115                 120                 125

Pro Val Pro Leu His Tyr Val Arg Asn His Gly Pro Val Pro Lys Gly
    130                 135                 140

Thr Trp Asp Asp Trp Thr Val Glu Val Thr Gly Leu Val Lys Arg Pro
145                 150                 155                 160

Met Lys Phe Thr Met Asp Gln Leu Val Asn Glu Phe Pro Cys Arg Glu
                165                 170                 175

Leu Pro Val Thr Leu Val Cys Ala Gly Asn Arg Arg Lys Glu Gln Asn
            180                 185                 190

Met Val Lys Gln Thr Ile Gly Phe Asn Trp Gly Ala Ala Ala Val Ser
        195                 200                 205

Thr Thr Ile Trp Arg Gly Val Pro Leu Arg Ala Leu Leu Lys Arg Cys
    210                 215                 220
```

-continued

```
Gly Val Phe Ser Lys Asn Lys Gly Ala Leu Asn Val Cys Phe Glu Gly
225                 230                 235                 240

Ala Asp Val Leu Pro Gly Gly Gly Ser Lys Tyr Gly Thr Ser Ile
            245                 250                 255

Lys Lys Glu Phe Ala Met Asp Pro Ala Arg Asp Ile Ile Val Ala Tyr
        260                 265                 270

Met Gln Asn Gly Glu Lys Leu Ala Pro Asp His Gly Phe Pro Val Arg
    275                 280                 285

Met Ile Ile Pro Gly Phe Ile Gly Gly Arg Met Val Lys Trp Ile Lys
    290                 295                 300

Arg Ile Ile Val Thr Thr Gln Glu Ser Asp Ser Tyr Tyr His Phe Lys
305                 310                 315                 320

Asp Asn Arg Val Leu Pro Pro His Val Asp Ala Glu Leu Ala Asn Thr
            325                 330                 335

Glu Ala Trp Trp Tyr Lys Pro Glu Tyr Ile Ile Asn Glu Leu Asn Ile
        340                 345                 350

Asn Ser Val Ile Thr Thr Pro Cys His Glu Glu Ile Leu Pro Ile Asn
    355                 360                 365

Ala Trp Thr Thr Gln Arg Pro Tyr Thr Leu Arg Gly Tyr Ser Tyr Ser
    370                 375                 380

Gly Gly Gly Lys Lys Val Thr Arg Val Glu Val Thr Leu Asp Gly Gly
385                 390                 395                 400

Glu Thr Trp Gln Val Ser Thr Leu Asp His Pro Glu Lys Pro Thr Lys
            405                 410                 415

Tyr Gly Lys Tyr Trp Cys Trp Cys Phe Trp Ser Leu Glu Val Glu Val
        420                 425                 430

Leu Asp Leu Leu Ser Ala Lys Glu Ile Ala Val Arg Ala Trp Asp Glu
    435                 440                 445

Thr Leu Asn Thr Gln Pro Glu Lys Leu Ile Trp Asn Val Met Gly Met
450                 455                 460

Met Asn Asn Cys Trp Phe Arg Val Lys Met Asn Val Cys Lys Pro His
465                 470                 475                 480

Lys Gly Glu Ile Gly Ile Val Phe Glu His Pro Thr Gln Pro Gly Asn
            485                 490                 495

Gln Ser Gly Gly Trp Met Ala Lys Glu Arg His Leu Glu Ile Ser Ala
        500                 505                 510

Glu Ala Pro Gln Thr Leu Lys Lys Ser Ile Ser Thr Pro Phe Met Asn
    515                 520                 525

Thr Ala Ser Lys Met Tyr Ser Met Ser Glu Val Arg Lys His Ser Ser
    530                 535                 540

Ala Asp Ser Ala Trp Ile Ile Val His Gly His Ile Tyr Asp Ala Thr
545                 550                 555                 560

Arg Phe Leu Lys Asp His Pro Gly Gly Thr Asp Ser Ile Leu Ile Asn
            565                 570                 575

Ala Gly Thr Asp Cys Thr Glu Glu Phe Asp Ala Ile His Ser Asp Lys
        580                 585                 590

Ala Lys Lys Leu Leu Glu Asp Phe Arg Ile Gly Glu Leu Ile Thr Thr
    595                 600                 605

Gly Tyr Thr Ser Asp Ser Pro Gly Asn Ser Val His Gly Ser Ser Ser
    610                 615                 620

Phe Ser Ser Phe Leu Ala Pro Ile Lys Glu Leu Val Pro Ala Gln Arg
625                 630                 635                 640

Ser Val Ala Leu Ile Pro Arg Glu Lys Ile Pro Cys Lys Leu Ile Asp
```

```
                    645                 650                 655
    Lys Gln Ser Ile Ser His Asp Val Arg Lys Phe Arg Phe Ala Leu Pro
                    660                 665                 670

Ser Glu Asp Gln Val Leu Gly Leu Pro Val Gly Lys His Ile Phe Leu
                675                 680                 685

Cys Ala Val Ile Asp Asp Lys Leu Cys Met Arg Ala Tyr Thr Pro Thr
            690                 695                 700

Ser Thr Ile Asp Glu Val Gly Tyr Phe Glu Leu Val Val Lys Ile Tyr
    705                 710                 715                 720

Phe Lys Gly Ile His Pro Lys Phe Pro Asn Gly Gly Gln Met Ser Gln
                    725                 730                 735

Tyr Leu Asp Ser Met Pro Leu Gly Ser Phe Leu Asp Val Lys Gly Pro
                740                 745                 750

Leu Gly His Ile Glu Tyr Gln Gly Lys Gly Asn Phe Leu Val His Gly
            755                 760                 765

Lys Gln Lys Phe Ala Lys Lys Leu Ala Met Ile Ala Gly Gly Thr Gly
    770                 775                 780

Ile Thr Pro Val Tyr Gln Val Met Gln Ala Ile Leu Lys Asp Pro Glu
    785                 790                 795                 800

Asp Asp Thr Glu Met Tyr Val Tyr Ala Asn Arg Thr Glu Asp Asp
                    805                 810                 815

Ile Leu Leu Lys Glu Glu Leu Asp Ser Trp Ala Glu Lys Ile Pro Glu
                820                 825                 830

Arg Val Lys Val Trp Tyr Val Val Gln Asp Ser Ile Lys Glu Gly Trp
            835                 840                 845

Lys Tyr Ser Ile Gly Phe Ile Thr Glu Ala Ile Leu Arg Glu His Ile
    850                 855                 860

Pro Glu Pro Ser His Thr Thr Leu Ala Leu Ala Cys Gly Pro Pro Pro
    865                 870                 875                 880

Met Ile Gln Phe Ala Val Asn Pro Asn Leu Glu Lys Met Gly Tyr Asp
                    885                 890                 895

Ile Lys Asp Ser Leu Leu Val Phe
                    900

<210> SEQ ID NO 5
<211> LENGTH: 2715
<212> TYPE: DNA
<213> ORGANISM: Artificial Sequence
<220> FEATURE:
<223> OTHER INFORMATION: Synthetic Oligonucleotide

<400> SEQUENCE: 5
atggcggcat ctgtcgaaaa caggcagttc agtcacctag aagccggttt atcccggtct    60
ttcaagcccc ggtctgattc cccggttcgt ggctgcaact tcccttcgcc aacagtact    120 aatttccaaa agaaaccaaa ttccaccatt taccttgatt actcgtcgag tgaagacgac    180
gatgatgatg acgaaaaaaa tgagtaccttt caaatgatta aaaaagggaa ttcagagtta    240
gagccatctg ttcatgacac tagggacgaa ggtaccgctg ataattggat tgaacgcaac    300 tttttccatga ttcgtctcac cggaaagcat ccatttaact ccgaaccacc gttgaaccgg    360
ctcatgcacc acggctttat cacaccggtc ccacttcatt acgttcgtaa ccatggaccg    420
gttcccaagg gcacgtggga tgactggacc gtggaagtca cgggactagt gaagcgtcct    480
atgaaattca atggaccag ttggttaac gaattccctt gtagagaatt gcccgttacg    540 cttgttgtg ctggcaatcg aaggaaagaa cagaacatgg ttaaacaaac cattggtttc    600
```

```
aactggggcg ccgctgccgt ttcaacaacg atatggcgcg gggtacccct ccgcgctttg    660
ctaaaacggt gcggtgtttt tagcaagaat aaagggggcgc ttaatgtttg cttcgaagga   720
gctgatgtgt tgcccggagg tggtggttca agtatggaa ccagcattaa gaaggaattt    780
gcaatggatc cagcacgaga tatcatcgta gcctacatgc agaacggaga aaaattggca   840
cccgaccacg ggtttccagt acgaatgata attccaggat tcattggagg aagaatggtg   900
aaatggataa agaggattat agtcaccacc caagaatcag acagctatta tcatttcaag   960
gacaatagag ttcttcctcc ccatgttgat gctgaacttg caaataccga agcatggtgg  1020
tacaagccag agtatatcat caatgagctt aatattaact ctgtcattac gacgccgtgt  1080
catgaagaaa ttttgccaat taacgcctgg acgactcagc gaccttacac gttgaggggc  1140
tattcttatt ctggcggagg gaaaaaagta acgcgagtag aagtgacgtt ggatggagga  1200
gaaacatggc aagttagcac actagatcac ccagagaagc ccaccaaata tggcaagtac  1260
tggtgttggt gcttttggtc actcgaggtt gaggtgttag acttgctcag tgctaaagaa  1320
attgctgttc gagcttggga tgagaccctc aatactcaac ccgagaagct tatttggaac  1380
gtcatgggaa tgatgaataa ttgctggttc cgagtaaaga tgaatgtgtg caagcctcac  1440
aagggagaga ttggaatagt gttttgagcat ccgactcaac ctggaaacca atcaggtgga  1500
tggatggcga aggagagaca tttggagata tcagcagagg cacctcaaac actaaagaag  1560
agtatcgata ctccattcat gaacacagct tccaagatgt actccatgtc cgaggtcagg  1620
aaacacagct ctgctgactc tgcttggatc atagtccatg gtcatatcta tgacgccacg  1680
cgtttcttga aagatcaccc tggtgggact gacagcattc tcatcaatgc tggcactgat  1740
tgcactgagg aatttgatgc aattcattct gataaggcta agaagctctt ggaggatttc  1800
aggattggtg aactcataac tactggttac acctctgact ctcctggcaa ctccgtgcac  1860
ggatcttctt ccttcagcag ctttctagca cctattaagg aacttgttcc agcgcagagg  1920
agtgtggccc taattccaag agagaaaatc ccatgcaaac tcatcgacaa gcaatccatc  1980
tcccatgatg ttaggaaatt tcgatttgca ttgccctctg aggatcaagt cttgggcttg  2040
cctgttggaa aacatatctt cctctgtgcc gttattgacg ataagctctg catgcgcgct  2100
tacacgccta ctagcacgat cgatgaggtg gggtacttcg agttggttgt caagatatac  2160
ttcaaaggaa ttcaccctaa attccccaat ggagggcaaa tgtcacagta tcttgattct  2220
atgccgttag ggtcatttct cgacgtgaaa ggtccattag gtcacattga ataccaagga  2280
aagggaaatt tcttagttca tggcaaacag aagtttgcca agaagttggc catgatagca  2340
ggtggaacag gaataactcc agtgtatcaa gtcatgcagg caattctgaa agatccagaa  2400
gatgacacag aaatgtatgt ggtgtatgct aacagaacag aggatgatat tttacttaag  2460
gaagagcttg attcatgggc tgagaaaatt ccagagaggg ttaaagtttg gtatgtggtt  2520
caggattcta ttaaagaagg atggaagtac agcattggtt ttattacaga agccattttg  2580
agagaacata tccctgagcc atctcacaca acactggctt tggcttgtgg accacctcct  2640
atgattcaat tgctgttaa tccaaacttg gagaagatgg gctatgacat taaggattcc  2700
ttattggtgt tctaa                                                    2715
```

<210> SEQ ID NO 6
<211> LENGTH: 904
<212> TYPE: PRT
<213> ORGANISM: Artificial Sequence
<220> FEATURE:

<223> OTHER INFORMATION: Synthetic Peptide

<400> SEQUENCE: 6

```
Met Ala Ala Ser Val Glu Asn Arg Gln Phe Ser His Leu Glu Ala Gly
1               5                   10                  15

Leu Ser Arg Ser Phe Lys Pro Arg Ser Asp Ser Pro Val Arg Gly Cys
            20                  25                  30

Asn Phe Pro Ser Pro Asn Ser Thr Asn Phe Gln Lys Lys Pro Asn Ser
        35                  40                  45

Thr Ile Tyr Leu Asp Tyr Ser Ser Glu Asp Asp Asp Asp Asp
    50                  55                  60

Glu Lys Asn Glu Tyr Leu Gln Met Ile Lys Lys Gly Asn Ser Glu Leu
65                  70                  75                  80

Glu Pro Ser Val His Asp Thr Arg Asp Glu Gly Thr Ala Asp Asn Trp
                85                  90                  95

Ile Glu Arg Asn Phe Ser Met Ile Arg Leu Thr Gly Lys His Pro Phe
            100                 105                 110

Asn Ser Glu Pro Pro Leu Asn Arg Leu Met His His Gly Phe Ile Thr
        115                 120                 125

Pro Val Pro Leu His Tyr Val Arg Asn His Gly Pro Val Pro Lys Gly
    130                 135                 140

Thr Trp Asp Asp Trp Thr Val Glu Val Thr Gly Leu Val Lys Arg Pro
145                 150                 155                 160

Met Lys Phe Thr Met Asp Gln Leu Val Asn Glu Phe Pro Cys Arg Glu
                165                 170                 175

Leu Pro Val Thr Leu Val Cys Ala Gly Asn Arg Arg Lys Glu Gln Asn
            180                 185                 190

Met Val Lys Gln Thr Ile Gly Phe Asn Trp Gly Ala Ala Ala Val Ser
        195                 200                 205

Thr Thr Ile Trp Arg Gly Val Pro Leu Arg Ala Leu Leu Lys Arg Cys
    210                 215                 220

Gly Val Phe Ser Lys Asn Lys Gly Ala Leu Asn Val Cys Phe Glu Gly
225                 230                 235                 240

Ala Asp Val Leu Pro Gly Gly Gly Gly Ser Lys Tyr Gly Thr Ser Ile
                245                 250                 255

Lys Lys Glu Phe Ala Met Asp Pro Ala Arg Asp Ile Ile Val Ala Tyr
            260                 265                 270

Met Gln Asn Gly Glu Lys Leu Ala Pro Asp His Gly Phe Pro Val Arg
        275                 280                 285

Met Ile Ile Pro Gly Phe Ile Gly Gly Arg Met Val Lys Trp Ile Lys
    290                 295                 300

Arg Ile Ile Val Thr Thr Gln Glu Ser Asp Ser Tyr Tyr His Phe Lys
305                 310                 315                 320

Asp Asn Arg Val Leu Pro Pro His Val Asp Ala Glu Leu Ala Asn Thr
                325                 330                 335

Glu Ala Trp Trp Tyr Lys Pro Glu Tyr Ile Ile Asn Glu Leu Asn Ile
            340                 345                 350

Asn Ser Val Ile Thr Thr Pro Cys His Glu Glu Ile Leu Pro Ile Asn
        355                 360                 365

Ala Trp Thr Thr Gln Arg Pro Tyr Thr Leu Arg Gly Tyr Ser Tyr Ser
    370                 375                 380

Gly Gly Gly Lys Lys Val Thr Arg Val Glu Val Thr Leu Asp Gly Gly
385                 390                 395                 400
```

```
Glu Thr Trp Gln Val Ser Thr Leu Asp His Pro Glu Lys Pro Thr Lys
                405                 410                 415

Tyr Gly Lys Tyr Trp Cys Trp Cys Phe Trp Ser Leu Glu Val Glu Val
            420                 425                 430

Leu Asp Leu Leu Ser Ala Lys Glu Ile Ala Val Arg Ala Trp Asp Glu
        435                 440                 445

Thr Leu Asn Thr Gln Pro Glu Lys Leu Ile Trp Asn Val Met Gly Met
    450                 455                 460

Met Asn Asn Cys Trp Phe Arg Val Lys Met Asn Val Cys Lys Pro His
465                 470                 475                 480

Lys Gly Glu Ile Gly Ile Val Phe Glu His Pro Thr Gln Pro Gly Asn
                485                 490                 495

Gln Ser Gly Gly Trp Met Ala Lys Glu Arg His Leu Glu Ile Ser Ala
            500                 505                 510

Glu Ala Pro Gln Thr Leu Lys Lys Ser Ile Asp Thr Pro Phe Met Asn
        515                 520                 525

Thr Ala Ser Lys Met Tyr Ser Met Ser Glu Val Arg Lys His Ser Ser
    530                 535                 540

Ala Asp Ser Ala Trp Ile Ile Val His Gly His Ile Tyr Asp Ala Thr
545                 550                 555                 560

Arg Phe Leu Lys Asp His Pro Gly Gly Thr Asp Ser Ile Leu Ile Asn
                565                 570                 575

Ala Gly Thr Asp Cys Thr Glu Glu Phe Asp Ala Ile His Ser Asp Lys
            580                 585                 590

Ala Lys Lys Leu Leu Glu Asp Phe Arg Ile Gly Glu Leu Ile Thr Thr
        595                 600                 605

Gly Tyr Thr Ser Asp Ser Pro Gly Asn Ser Val His Gly Ser Ser Ser
    610                 615                 620

Phe Ser Ser Phe Leu Ala Pro Ile Lys Glu Leu Val Pro Ala Gln Arg
625                 630                 635                 640

Ser Val Ala Leu Ile Pro Arg Glu Lys Ile Pro Cys Lys Leu Ile Asp
                645                 650                 655

Lys Gln Ser Ile Ser His Asp Val Arg Lys Phe Arg Phe Ala Leu Pro
            660                 665                 670

Ser Glu Asp Gln Val Leu Gly Leu Pro Val Gly Lys His Ile Phe Leu
        675                 680                 685

Cys Ala Val Ile Asp Asp Lys Leu Cys Met Arg Ala Tyr Thr Pro Thr
    690                 695                 700

Ser Thr Ile Asp Glu Val Gly Tyr Phe Glu Leu Val Val Lys Ile Tyr
705                 710                 715                 720

Phe Lys Gly Ile His Pro Lys Phe Pro Asn Gly Gly Gln Met Ser Gln
                725                 730                 735

Tyr Leu Asp Ser Met Pro Leu Gly Ser Phe Leu Asp Val Lys Gly Pro
            740                 745                 750

Leu Gly His Ile Glu Tyr Gln Gly Lys Gly Asn Phe Leu Val His Gly
        755                 760                 765

Lys Gln Lys Phe Ala Lys Lys Leu Ala Met Ile Ala Gly Gly Thr Gly
    770                 775                 780

Ile Thr Pro Val Tyr Gln Val Met Gln Ala Ile Leu Lys Asp Pro Glu
785                 790                 795                 800

Asp Asp Thr Glu Met Tyr Val Val Tyr Ala Asn Arg Thr Glu Asp Asp
                805                 810                 815

Ile Leu Leu Lys Glu Glu Leu Asp Ser Trp Ala Glu Lys Ile Pro Glu
```

-continued

```
                820                 825                 830
Arg Val Lys Val Trp Tyr Val Val Gln Asp Ser Ile Lys Glu Gly Trp
            835                 840                 845

Lys Tyr Ser Ile Gly Phe Ile Thr Glu Ala Ile Leu Arg Glu His Ile
        850                 855                 860

Pro Glu Pro Ser His Thr Thr Leu Ala Leu Ala Cys Gly Pro Pro Pro
865                 870                 875                 880

Met Ile Gln Phe Ala Val Asn Pro Asn Leu Glu Lys Met Gly Tyr Asp
                885                 890                 895

Ile Lys Asp Ser Leu Leu Val Phe
            900

<210> SEQ ID NO 7
<211> LENGTH: 2547
<212> TYPE: DNA
<213> ORGANISM: Artificial Sequence
<220> FEATURE:
<223> OTHER INFORMATION: Synthetic Oligonucleotide

<400> SEQUENCE: 7
atggcggcat ctgtcgaaaa caggcagttc agtcacctag aagccggttt atcccggtct      60
aattcagagt tagagccatc tgttcatgac actagggacg aaggtaccgc tgataattgg     120
attgaacgca acttttccat gattcgtctc accggaaagc atccatttaa ctccgaacca     180
ccgttgaacc ggctcatgca ccacggcttt atcacaccgg tcccacttca ttacgttcgt     240
aaccatggac cggttcccaa gggcacgtgg atgactgga ccgtggaagt cacgggacta     300
gtgaagcgtc ctatgaaatt cacaatggac cagttggtta cgaattccc ttgtagagaa     360 ttgcccgtta cgcttgtttg tgctggcaat cgaaggaaag aacagaacat ggttaaacaa     420
accattggtt tcaactgggg cgccgctgcc gtttcaacaa cgatatggcg cggggtaccc     480
ctccgcgctt tgctaaaacg gtgcggtgtt tttagcaaga ataaaggggc gcttaatgtt     540
tgcttcgaag gagctgatgt gttgcccgga ggtggtggtt caaagtatgg aaccagcatt     600
aagaaggaat ttgcaatgga tccagcacga gatatcatcg tagcctacat gcagaacgga     660
gaaaaattgg cacccgacca cgggtttcca gtacgaatga taattccagg attcattgga     720
ggaagaatgg tgaaatggat aaagaggatt atagtcacca cccaagaatc agacagctat     780
tatcatttca aggacaatag agttcttcct ccccatgttg atgctgaact tgcaaatacc     840
gaagcatggt ggtacaagcc agagtatatc atcaatgagc ttaatattaa ctctgtcatt     900
acgacgccgt gtcatgaaga aattttgcca attaacgcct ggacgactca gcgaccttac     960
acgttgaggg gctattctta ttctggcgga gggaaaaaag taacgcgagt agaagtgacg    1020
ttggatggag gagaaacatg gcaagttagc acactagatc acccagagaa gcccaccaaa    1080
tatggcaagt actggtgttg gtgctttttgg tcactcgagg ttgaggtgtt agacttgctc    1140
agtgctaaag aaattgctgt tcgagcttgg gatgagaccc tcaatactca acccgagaag    1200
cttatttgga acgtcatggg aatgatgaat aattgctggt tccgagtaaa gatgaatgtg    1260
tgcaagcctc acaagggaga gattggaata gtgtttgagc atccgactca acctggaaac    1320
caatcaggtg gatggatggc gaaggagaga catttggaga tatcagcaga ggcacctcaa    1380
acactaaaga gagtatctc aactccattc atgaacacag cttccaagat gtactccatg    1440
tccgaggtca ggaaacacag ctctgctgac tctgcttgga tcatagtcca tggtcatatc    1500
tatgacgcca cgcgtttctt gaaagatcac cctggtggga ctgacagcat tctcatcaat    1560
```

```
gctggcactg attgcactga ggaatttgat gcaattcatt ctgataaggc taagaagctc    1620
ttggaggatt tcaggattgg tgaactcata actactggtt acacctctga ctctcctggc    1680
aactccgtgc acggatcttc ttccttcagc agctttctag cacctattaa ggaacttgtt    1740
ccagcgcaga ggagtgtggc cctaattcca agagagaaaa tcccatgcaa actcatcgac    1800
aagcaatcca tctcccatga tgttaggaaa tttcgatttg cattgccctc tgaggatcaa    1860
gtcttgggct tgcctgttgg aaaacatatc ttcctctgtg ccgttattga cgataagctc    1920
tgcatgcgcg cttacacgcc tactagcacg atcgatgagg tggggtactt cgagttggtt    1980
gtcaagatat acttcaaagg aattcaccct aaattcccca atggagggca aatgtcacag    2040
tatcttgatt ctatgccgtt agggtcattt ctcgacgtga aggtccatt aggtcacatt     2100 gaataccaag gaaagggaaa tttcttagtt catggcaaac agaagtttgc caagaagttg    2160
gccatgatag caggtggaac aggaataact ccagtgtatc aagtcatgca ggcaattctg    2220
aaagatccag aagatgacac agaaatgtat gtggtgtatg ctaacagaac agaggatgat    2280
attttactta aggaagagct tgattcatgg gctgagaaaa ttccagagag ggttaaagtt    2340
tggtatgtgg ttcaggattc tattaaagaa ggatggaagt acagcattgg tttttattaca    2400 gaagccattt tgagagaaca tatccctgag ccatctcaca caacactggc tttggcttgt    2460
ggaccacctc ctatgattca atttgctgtt aatccaaact tggagaagat gggctatgac    2520
attaaggatt ccttattggt gttctaa                                        2547
```

<210> SEQ ID NO 8
<211> LENGTH: 848
<212> TYPE: PRT
<213> ORGANISM: Artificial Sequence
<220> FEATURE:
<223> OTHER INFORMATION: Synthetic Peptide

<400> SEQUENCE: 8

```
Met Ala Ala Ser Val Glu Asn Arg Gln Phe Ser His Leu Glu Ala Gly
1               5                   10                  15

Leu Ser Arg Ser Asn Ser Glu Leu Glu Pro Ser Val His Asp Thr Arg
            20                  25                  30

Asp Glu Gly Thr Ala Asp Asn Trp Ile Glu Arg Asn Phe Ser Met Ile
        35                  40                  45

Arg Leu Thr Gly Lys His Pro Phe Asn Ser Glu Pro Pro Leu Asn Arg
    50                  55                  60

Leu Met His His Gly Phe Ile Thr Pro Val Pro Leu His Tyr Val Arg
65                  70                  75                  80

Asn His Gly Pro Val Pro Lys Gly Thr Trp Asp Asp Trp Thr Val Glu
                85                  90                  95

Val Thr Gly Leu Val Lys Arg Pro Met Lys Phe Thr Met Asp Gln Leu
            100                 105                 110

Val Asn Glu Phe Pro Cys Arg Glu Leu Pro Val Thr Leu Val Cys Ala
        115                 120                 125

Gly Asn Arg Arg Lys Glu Gln Asn Met Val Lys Gln Thr Ile Gly Phe
    130                 135                 140

Asn Trp Gly Ala Ala Val Ser Thr Thr Ile Trp Arg Gly Val Pro
145                 150                 155                 160

Leu Arg Ala Leu Leu Lys Arg Cys Gly Val Phe Ser Lys Asn Lys Gly
                165                 170                 175

Ala Leu Asn Val Cys Phe Glu Gly Ala Asp Val Leu Pro Gly Gly Gly
            180                 185                 190
```

```
Gly Ser Lys Tyr Gly Thr Ser Ile Lys Lys Glu Phe Ala Met Asp Pro
            195                 200                 205

Ala Arg Asp Ile Ile Val Ala Tyr Met Gln Asn Gly Glu Lys Leu Ala
            210                 215                 220

Pro Asp His Gly Phe Pro Val Arg Met Ile Ile Pro Gly Phe Ile Gly
225                 230                 235                 240

Gly Arg Met Val Lys Trp Ile Lys Arg Ile Val Thr Thr Gln Glu
                245                 250                 255

Ser Asp Ser Tyr Tyr His Phe Lys Asp Asn Arg Val Leu Pro Pro His
                260                 265                 270

Val Asp Ala Glu Leu Ala Asn Thr Glu Ala Trp Trp Tyr Lys Pro Glu
            275                 280                 285

Tyr Ile Ile Asn Glu Leu Asn Ile Asn Ser Val Ile Thr Thr Pro Cys
            290                 295                 300

His Glu Glu Ile Leu Pro Ile Asn Ala Trp Thr Thr Gln Arg Pro Tyr
305                 310                 315                 320

Thr Leu Arg Gly Tyr Ser Tyr Ser Gly Gly Lys Lys Val Thr Arg
                325                 330                 335

Val Glu Val Thr Leu Asp Gly Gly Glu Thr Trp Gln Val Ser Thr Leu
            340                 345                 350

Asp His Pro Glu Lys Pro Thr Lys Tyr Gly Lys Tyr Trp Cys Trp Cys
            355                 360                 365

Phe Trp Ser Leu Glu Val Glu Val Leu Asp Leu Leu Ser Ala Lys Glu
            370                 375                 380

Ile Ala Val Arg Ala Trp Asp Glu Thr Leu Asn Thr Gln Pro Glu Lys
385                 390                 395                 400

Leu Ile Trp Asn Val Met Gly Met Met Asn Asn Cys Trp Phe Arg Val
                405                 410                 415

Lys Met Asn Val Cys Lys Pro His Lys Gly Glu Ile Gly Ile Val Phe
                420                 425                 430

Glu His Pro Thr Gln Pro Gly Asn Gln Ser Gly Gly Trp Met Ala Lys
            435                 440                 445

Glu Arg His Leu Glu Ile Ser Ala Glu Ala Pro Gln Thr Leu Lys Lys
            450                 455                 460

Ser Ile Ser Thr Pro Phe Met Asn Thr Ala Ser Lys Met Tyr Ser Met
465                 470                 475                 480

Ser Glu Val Arg Lys His Ser Ser Ala Asp Ser Ala Trp Ile Ile Val
                485                 490                 495

His Gly His Ile Tyr Asp Ala Thr Arg Phe Leu Lys Asp His Pro Gly
            500                 505                 510

Gly Thr Asp Ser Ile Leu Ile Asn Ala Gly Thr Asp Cys Thr Glu Glu
            515                 520                 525

Phe Asp Ala Ile His Ser Asp Lys Ala Lys Lys Leu Leu Glu Asp Phe
530                 535                 540

Arg Ile Gly Glu Leu Ile Thr Thr Gly Tyr Thr Ser Asp Ser Pro Gly
545                 550                 555                 560

Asn Ser Val His Gly Ser Ser Ser Phe Ser Ser Phe Leu Ala Pro Ile
                565                 570                 575

Lys Glu Leu Val Pro Ala Gln Arg Ser Val Ala Leu Ile Pro Arg Glu
            580                 585                 590

Lys Ile Pro Cys Lys Leu Ile Asp Lys Gln Ser Ile Ser His Asp Val
            595                 600                 605
```

```
Arg Lys Phe Arg Phe Ala Leu Pro Ser Glu Asp Gln Val Leu Gly Leu
    610                 615                 620

Pro Val Gly Lys His Ile Phe Leu Cys Ala Val Ile Asp Asp Lys Leu
625                 630                 635                 640

Cys Met Arg Ala Tyr Thr Pro Thr Ser Thr Ile Asp Glu Val Gly Tyr
                645                 650                 655

Phe Glu Leu Val Val Lys Ile Tyr Phe Lys Gly Ile His Pro Lys Phe
            660                 665                 670

Pro Asn Gly Gly Gln Met Ser Gln Tyr Leu Asp Ser Met Pro Leu Gly
        675                 680                 685

Ser Phe Leu Asp Val Lys Gly Pro Leu Gly His Ile Glu Tyr Gln Gly
690                 695                 700

Lys Gly Asn Phe Leu Val His Gly Lys Gln Lys Phe Ala Lys Lys Leu
705                 710                 715                 720

Ala Met Ile Ala Gly Gly Thr Gly Ile Thr Pro Val Tyr Gln Val Met
                725                 730                 735

Gln Ala Ile Leu Lys Asp Pro Glu Asp Thr Glu Met Tyr Val Val
            740                 745                 750

Tyr Ala Asn Arg Thr Glu Asp Asp Ile Leu Leu Lys Glu Glu Leu Asp
        755                 760                 765

Ser Trp Ala Glu Lys Ile Pro Glu Arg Val Lys Val Trp Tyr Val Val
770                 775                 780

Gln Asp Ser Ile Lys Glu Gly Trp Lys Tyr Ser Ile Gly Phe Ile Thr
785                 790                 795                 800

Glu Ala Ile Leu Arg Glu His Ile Pro Glu Pro Ser His Thr Thr Leu
                805                 810                 815

Ala Leu Ala Cys Gly Pro Pro Met Ile Gln Phe Ala Val Asn Pro
            820                 825                 830

Asn Leu Glu Lys Met Gly Tyr Asp Ile Lys Asp Ser Leu Leu Val Phe
        835                 840                 845

<210> SEQ ID NO 9
<211> LENGTH: 11
<212> TYPE: PRT
<213> ORGANISM: Artificial Sequence
<220> FEATURE:
<223> OTHER INFORMATION: Tomato; NIA; 523-533

<400> SEQUENCE: 9

Leu Lys Lys Ser Ile Ser Thr Pro Phe Met Asn
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Tobacco; NIA1; 518-528

<400> SEQUENCE: 10

Leu Lys Lys Ser Ile Ser Thr Pro Phe Met Asn
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Tobacco; NIA2; 518-528
```

```
<400> SEQUENCE: 11

Leu Lys Lys Ser Ile Ser Thr Pro Phe Met Asn
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Petunia; NIA; 522-532

<400> SEQUENCE: 12

Leu Lys Lys Ser Ile Ser Thr Pro Phe Met Asn
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Squash; NIA; 530-540

<400> SEQUENCE: 13

Leu Lys Lys Ser Val Ser Thr Pro Phe Met Asn
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Birch; NIA1; 515-525

<400> SEQUENCE: 14

Leu Lys Lys Ser Val Ser Thr Pro Phe Met Asn
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Arabidopsis; NIA1; 532-542

<400> SEQUENCE: 15

Leu Lys Lys Ser Val Ser Ser Pro Phe Met Asn
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Arabidopsis; NIA2; 529-539

<400> SEQUENCE: 16

Leu Lys Lys Ser Val Ser Thr Pro Phe Met Asn
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Rape; NIA1; 526-536

<400> SEQUENCE: 17
```

Leu Lys Lys Ser Val Ser Ser Pro Phe Met Asn
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Rape; NIA2; 526-536

<400> SEQUENCE: 18

Leu Lys Lys Ser Val Ser Thr Pro Phe Met Asn
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Soybean; NIA2; 504-514

<400> SEQUENCE: 19

Leu Lys Lys Ser Val Ser Ser Pro Phe Met Asn
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Kidney bean; NIA1; 502-512

<400> SEQUENCE: 20

Leu Lys Lys Ser Val Ser Thr Pro Phe Met Asn
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Kidney bean; NIA2; 500-510

<400> SEQUENCE: 21

Leu Lys Lys Ser Val Ser Ser Pro Phe Met Asn
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Lotus japonicus; NIA; 508-518

<400> SEQUENCE: 22

Leu Lys Lys Ser Val Ser Ser Pro Phe Met Asn
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Cichorium; NIA1; 521-531

<400> SEQUENCE: 23

```
Leu Lys Lys Ser Val Ser Ser Pro Phe Met Asn
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Maize; NIA1; 234-244

<400> SEQUENCE: 24

Leu Lys Arg Ser Thr Ser Thr Pro Phe Met Asn
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Barley; NIA1; 524-534

<400> SEQUENCE: 25

Leu Lys Arg Ser Thr Ser Thr Pro Phe Met Asn
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Barley; NIA2; 521-531

<400> SEQUENCE: 26

Leu Lys Arg Ser Thr Ser Thr Pro Phe Met Asn
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Rice; NIA1; 527-537

<400> SEQUENCE: 27

Leu Lys Arg Ser Thr Ser Thr Pro Phe Met Asn
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Spinach; NIA; 538-548

<400> SEQUENCE: 28

Leu Lys Arg Thr Ala Ser Thr Pro Phe Met Asn
1               5                   10
```

REDUCING TOBACCO SPECIFIC NITROSAMINES THROUGH ALTERATION OF THE NITRATE ASSIMILATION PATHWAY

This application is a U.S. National Stage Application of International Application No. PCT/EP2015/071919, filed Sep. 23, 2015, which was published in English on Mar. 31, 2016, as International Publication No. WO 2016/046288 A1. International Application No. PCT/EP2015/071919 claims priority to European Application No. 14186705.1, filed Sep. 26, 2014 and European Application No. 14194798.6 dated Nov. 25, 2014.

FIELD OF THE INVENTION

The present invention relates to modified tobacco plants having reduced nitrate levels, tobacco products generated from the modified tobacco plants having reduced tobacco specific nitrosamines (TSNAs), and methods of reducing TSNAs in tobacco products by altering the gene expression of the nitrate assimilation pathway.

BACKGROUND

Commercial tobacco plants, such as burley tobacco, accumulate high levels of free nitrate in their leaves, which are undesirable because high levels of nitrate have been associated with the formation of carcinogenic compounds referred to as tobacco-specific nitrosamines (TSNAs). TSNAs are a class of compounds that are predominantly produced during the curing of tobacco leaves, though additional formation can occur in the subsequent processing and storage of leaf, and possibly via pyrosynthesis during combustion. Two of the TSNAs found in the cured leaf, N-nitrosonornicotine (NNN) and 4-(methylnitrosamino)-1-(3-pyridyl)-1-butanone (NNK), are classified as Group I carcinogens (the highest designation) by the International Agency for Research on Cancer. Due to the volume of evidence implicating these compounds with various tobacco-associated cancers, the World Health organization and other experts in the field have recommended that mandates be implemented to ensure that future tobacco products have reduced levels of these toxicants. TSNAs represent nitrosation products of tobacco alkaloids. In air-cured tobaccos there is a general consensus that nitrite is the agent directly responsible for TSNA formation. Due to its cellular toxicity, however, endogenous nitrite levels are typically very low in plant tissues. Instead, it is believed that the great majority of the nitrite involved in TSNA formation is derived from the nitrate reductase (NR) activity of microbes residing on the leaf surface during the 6-10 week curing process that converts a portion of the leaf nitrate pools to nitrite as cellular membranes and organelles become degraded during this period.

TSNAs are formed primarily during the curing process of leaves and involve the nitrosation of tobacco alkaloids. Genetic strategies to lower TSNA content and levels in the cured leaf have focused on targeting either: (1) the alkaloid precursor(s); or (2) the nitrosating agent(s) involved. Most efforts to reduce TSNAs at the level of altering the genetics of tobacco have targeted the alkaloid precursors to TSNAs. Such strategies provide substantial reductions in NNN through the downregulation of the gene family responsible for the synthesis of its alkaloid precursor nomicotine. However, such strategies do not reduce all of the TSNA levels found in tobacco products. Accordingly, there remains a great need for reducing all TSNAs levels in a tobacco product.

SUMMARY OF INVENTION

The present invention is directed, in on aspect, to a tobacco product having reduced tobacco specific nitrosamine (TSNA) levels which is generated from a tobacco plant, said tobacco plant being modified to comprise: (i) a polynucleotide comprising, consisting or consisting essentially of a sequence encoding a deregulated nitrate reductase enzyme; (ii) a polypeptide encoded by the polynucleotide set forth in (i); (iii) a polypeptide comprising, consisting or consisting essentially of a deregulated nitrate reductase enzyme; or (iv) a construct, vector or expression vector comprising the polynucleotide set forth in (i), wherein the expression or activity of said nitrate reductase is deregulated as compared to a control unmodified tobacco plant; and wherein the deregulated nitrate reductase enzyme comprises (a) a nitrate reductase polypeptide comprising an amino acid substitution at a position corresponding to position 523 of SEQ ID NO: 4; or (b) a nitrate reductase polypeptide comprising an amino acid substitution at a position corresponding to position 523 of SEQ ID NO: 4, wherein the amino acid at position 523 of SEQ ID NO: 4 is substituted to an aspartic acid. The deregulated nitrate reductase enzyme may be a nitrate reductase enzyme that is constitutively active. The tobacco plant may be from the species *Nicotiana tabacum*, e.g. the tobacco product may comprise plant material from a tobacco plant of the species *Nicotiana tabacum*. The polynucleotide encoding a deregulated nitrate reductase may be a heterologous polynucleotide encoding a modified nitrate reductase polypeptide. The heterologous polynucleotide may be linked to a promoter not natively associated with an endogenous nitrate reductase gene. The promoter may be the Cauliflower Mosaic Virus 35S promoter. The polynucleotide encoding a deregulated nitrate reductase may comprise a polynucleotide sequence of SEQ ID NO: 5. The polynucleotide encoding a deregulated nitrate reductase may encode an endogenous nitrate reductase gene that has been modified by a genome editing system or by a mutagen. The genome editing system may comprise an engineered CRISPR/Cas-based system, an engineered Transcription Activator-Like effector nuclease, an engineered zinc finger nuclease, or an engineered meganuclease. The tobacco may be a burley tobacco. The tobacco product may have reduced tobacco specific nitrosamine (TSNA) levels compared to a tobacco product derived from a control tobacco plant in which the nitrate reductase enzyme has not been deregulated. The total TSNA level may be measured in a leaf from the tobacco plant, wherein (a) the leaf is freshly harvested; (b) the leaf is cured, stored or processed; or (c) the leaf is air-cured. The level of at least one TSNA in the tobacco product may be reduced compared to a control level for the at least one TSNA, wherein the at least one TSNA is selected from the group consisting of N-nitrosonornicotine (NNN), 4-(methylnitrosamino)-1-(3-pyridyl)-1-butanone (NNK), N-nitrosoanabasine (NAB), N-nitrosoanatabine (NAT), and combinations thereof. The total levels of TSNA may be reduced by at least 50%. The TSNA levels may be measured in smoke obtained from combustion of leaves of the tobacco plant. The total TSNA levels in smoke may be reduced by at least 70%. The level of NNN may be reduced by about 90%. The level of NNK may be reduced by about 66%. The level of NAB may be reduced by about 92%. The level of NAT may be reduced by about 88%. The tobacco plant may further comprise a modified nornicotine pathway gene. The modified nornicotine pathway gene may comprise a modified nicotine demethylase gene or cytochrome P450 gene. The tobacco plant may comprise a modified CYP82E4 or modified CYP82E10 gene. The modified CYP82E4 gene or modified CYP82E10 gene may be inactivated.

The present invention is directed, in one aspect, to a method for producing a tobacco product wherein TSNA levels measured in smoke obtained from combustion of leaves of a modified tobacco plant are reduced compared to TSNA levels measured in smoke obtained from combustion of an unmodified tobacco plant. The method comprises (a) modifying a tobacco plant to comprise: (i) a polynucleotide comprising, consisting or consisting essentially of a sequence encoding a deregulated nitrate reductase enzyme; (ii) a polypeptide encoded by the polynucleotide set forth in (i); (iii) a polypeptide comprising, consisting or consisting essentially of a deregulated nitrate reductase enzyme; or (iv) a construct, vector or expression vector comprising the polynucleotide set forth in (i), wherein the expression or activity of said nitrate reductase is deregulated as compared to a control unmodified tobacco plant; and wherein the deregulated nitrate reductase enzyme comprises (I) a nitrate reductase polypeptide comprising an amino acid substitution at a position corresponding to position 523 of SEQ ID NO: 4; or (II) a nitrate reductase polypeptide comprising an amino acid substitution at a position corresponding to position 523 of SEQ ID NO: 4, wherein the amino acid at position 523 of SEQ ID NO: 4 is substituted to an aspartic acid; (b) harvesting tobacco leaves from said modified tobacco plant; and (c) producing a tobacco product from the harvested leaves.

In another aspect, also disclosed herein is a tobacco product having reduced tobacco specific nitrosamine (TSNA) levels which is generated from a tobacco plant, said tobacco plant being modified to comprise: (i) a polynucleotide comprising, consisting or consisting essentially of a sequence encoding a deregulated nitrate reductase enzyme; (ii) a polypeptide encoded by the polynucleotide set forth in (i); (iii) a polypeptide comprising, consisting or consisting essentially of a deregulated nitrate reductase enzyme; or (iv) a construct, vector or expression vector comprising the polynucleotide set forth in (i), wherein the expression or activity of said nitrate reductase is deregulated as compared to a control unmodified tobacco plant; and wherein the deregulated nitrate reductase enzyme comprises (a) a truncated nitrate reductase polypeptide; (b) a nitrate reductase polypeptide which comprises an N-terminal truncation; or (c) a nitrate reductase polypeptide which comprises an N-terminal truncation of 56 amino acids.

In another aspect, also disclosed herein is a method for producing a tobacco product wherein TSNA levels measured in smoke obtained from combustion of leaves of a modified tobacco plant are reduced compared to TSNA levels measured in smoke obtained from combustion of an unmodified tobacco plant, the method comprising (a) modifying a tobacco plant to comprise: (i) a polynucleotide comprising, consisting or consisting essentially of a sequence encoding a deregulated nitrate reductase enzyme; (ii) a polypeptide encoded by the polynucleotide set forth in (i); (iii) a polypeptide comprising, consisting or consisting essentially of a deregulated nitrate reductase enzyme; or (iv) a construct, vector or expression vector comprising the polynucleotide set forth in (i), wherein the expression or activity of said nitrate reductase is deregulated as compared to a control unmodified tobacco plant; and wherein the deregulated nitrate reductase enzyme comprises (I) a truncated nitrate reductase polypeptide; (II) a nitrate reductase polypeptide which comprises an N-terminal truncation; or (III) a nitrate reductase polypeptide which comprises an N-terminal truncation of 56 amino acids; (b) harvesting tobacco leaves from said modified tobacco plant; and (c) producing a tobacco product from the harvested leaves.

The polynucleotide encoding a deregulated nitrate reductase may comprise a polynucleotide sequence of SEQ ID NO: 7.

BRIEF DESCRIPTION OF THE DRAWINGS

FIG. 2 shows an alignment of the region containing position 523 of nitrate reductase amino acid sequences from various plant species.

FIGS. 3A and 3B show construct maps of the 35S:GS1, 35S:ICDH, 35S:GOGAT, E4:GOGAT, 35S:tr-NR, E4:tr-NR, 35S:S523D-NR, and E4:S523D-NR constructs.

DETAILED DESCRIPTION

Figure 1:
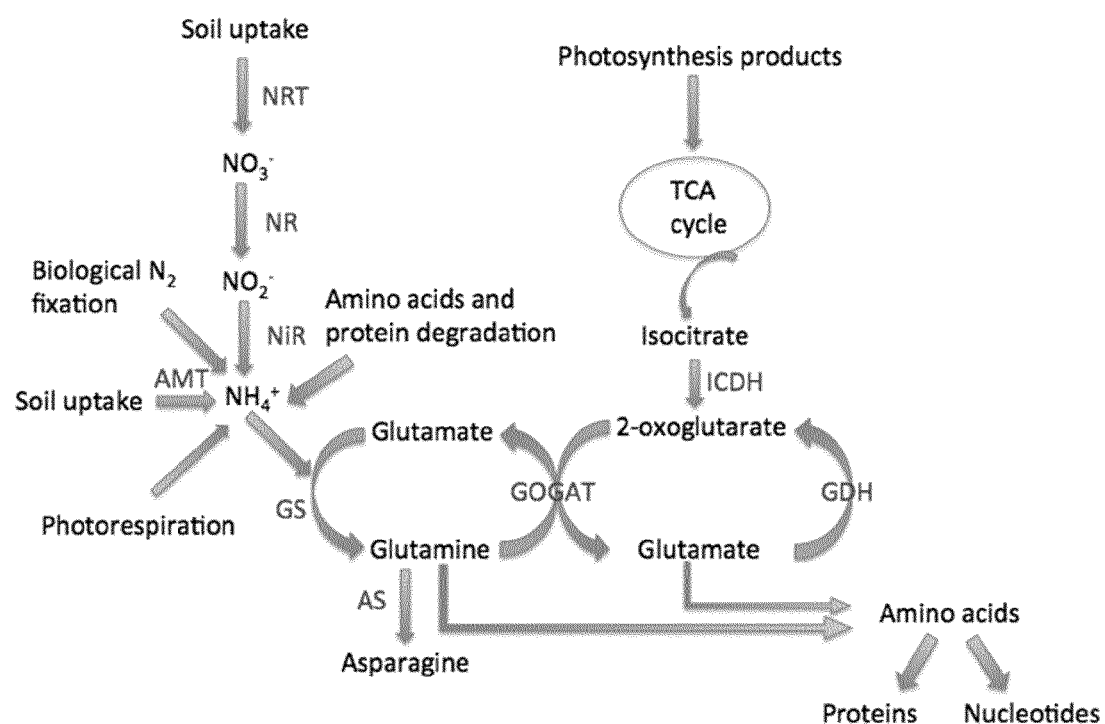
FIG. 1 shows a schematic of the nitrogen assimilation pathway in higher plants. In the primary N-assimilation pathway, nitrate ($NO_3^-$) is converted to nitrite ($NO_2^-$), then subsequently to ammonium ($NH_4^+$) and glutamine, with the primary enzymes involved in these reactions being nitrate and nitrite reductase (NR and NiR, respectively), glutamine synthetase (GS), and glutamate synthase (GOGAT). AMT, ammonium transporters; AS, asparagine synthetase; GDH, NADH-dependent glutamate dehydrogenase; ICDH, NADP-dependent isocitrate dehydrogenase; NRT, nitrate transporters; TCA, tricarboxylic acid cycle.

The present invention is directed, in one aspect, to a novel strategy for reducing free nitrate levels in the leaves of modified tobacco plants by altering the nitrate assimilation pathway, thereby reducing the levels of all TSNAs in the cured leaves from the modified tobacco plant. Free nitrate levels and TSNA content and levels, including total TSNA and/or specific TSNAs, of tobacco leaves were reduced using deregulated nitrate reductases. By targeting the nitrosating agent and reducing the amount of free nitrate that is stored within the leaf, the production of carcinogenic TSNAs in tobacco products is minimized. This technology represents a novel approach for TSNA reduction that could help the tobacco industry produce tobacco products with lower levels of TSNAs than is possible using current practices.

Deregulated nitrate reductases have been described in *Nicotiana plumbaginofolia*, for example by Nussaume et al. Plant Cell 7:611-621 (1995), as well as Lea et al., Plant Physiology 140:1085-1094 (2006). The reduction in nitrate levels observed in *N. plumbaginofolia* is significantly inferior to that observed in *N. tabacum* in the data presented here. Moreover, a reduction in TSNA levels resulting from deregulated nitrate reductases has not previously been demonstrated.

Section headings as used in this section and the entire disclosure herein are merely for organization purposes and are not intended to be limiting.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not. For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

As used throughout the specification and the claims, the following terms have the following meanings:

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered. The coding sequence may be codon optimized.

"Complement" or "complementary" as used herein means a nucleic acid can mean Watson-Crick (e.g., A-T/U and C-G) or Hoogsteen base pairing between nucleotides or nucleotide analogs of nucleic acid molecules. "Complementarity" refers to a property shared between two nucleic acid sequences, such that when they are aligned antiparallel to each other, the nucleotide bases at each position will be complementary.

"Construct" as used herein refers to a double-stranded, recombinant nucleic acid fragment comprising one or more polynucleotides. The construct comprises a "template strand" base-paired with a complementary "sense or coding strand." A given construct can be inserted into a vector in two possible orientations, either in the same (or sense) orientation or in the reverse (or anti-sense) orientation with respect to the orientation of a promoter positioned within a vector—such as an expression vector.

The term "control" as used herein in the context of a control plant or control plant cells means a plant or plant cells in which the expression or activity of nitrate reductase has not been modified (for example, increased or decreased) and so it can provide a comparison with a plant in which the expression or activity of nitrate reductase has been modified. As used herein, a "control plant" is a plant that is substantially equivalent to a test plant or modified plant in all parameters with the exception of the test parameters. For example, when referring to a plant into which a polynucleotide according to the present invention has been introduced, in certain embodiments, a control plant is an equivalent plant into which no such polynucleotide has been introduced. In certain embodiments, a control plant is an equivalent plant into which a control polynucleotide has been introduced. In such instances, the control polynucleotide is one that is expected to result in little or no phenotypic effect on the plant. The control plant may comprise an empty vector. The control plant may correspond to a wild-type plant. The control plant may be a null segregant wherein the T1 segregant no longer possesses the transgene.

"Donor DNA" or "donor template" as used interchangeably herein refers to a double-stranded DNA fragment or molecule that includes at least a portion of the gene of interest. The donor DNA may encode a full-functional protein or a partially-functional protein.

"Endogenous gene" as used herein refers to a gene that originates from the genome of the organism and has not undergone a change, such as a loss, gain, or exchange of genetic material. An endogenous gene undergoes normal gene transmission and gene expression.

"Enhancer sequences" as used herein refer to the sequences that can increase gene expression. These sequences can be located upstream, within introns or downstream of the transcribed region. The transcribed region is comprised of the exons and the intervening introns, from the promoter to the transcription termination region. The enhancement of gene expression can be through various mechanisms which include, but are not limited to, increasing transcriptional efficiency, stabilization of mature mRNA and translational enhancement.

"Expression" as used herein refers to the production of a functional product. For example, expression of a nucleic acid fragment may refer to transcription of the nucleic acid fragment (e.g., transcription resulting in mRNA or functional RNA) and/or translation of mRNA into a precursor or mature protein. "Overexpression" refers to the production of a gene product in transgenic organisms that exceeds levels of production in a null segregating (or non-transgenic) organism from the same experiment.

"Functional" and "full-functional" as used herein describes protein that has biological activity. A "functional gene" refers to a gene transcribed to mRNA, which is translated to a functional protein.

"Genetic construct" as used herein refers to the DNA or RNA molecules that comprise a nucleotide sequence that encodes a protein. The coding sequence includes initiation and termination signals operably linked to regulatory elements including a promoter and polyadenylation signal capable of directing expression in the cells of the individual to whom the nucleic acid molecule is administered.

"Genome editing" as used herein refers to changing an endogenous gene that encodes an endogenous polypeptide or protein, such that protein expression of a truncated endogenous protein or an endogenous protein having an amino acid substitution is obtained. Genome editing may include replacing the region of the endogenous gene to be targeted or replacing the entire endogenous gene with a copy of the gene that has a truncation or an amino acid substitution with a repair mechanism such as homology-directed repair (HDR). Genome editing may include may also include generating an amino acid substitution in the endogenous gene by generating a double stranded break in the endogenous gene that is then repaired using non-homologous end joining (NHEJ). NHEJ may add or delete at least one base pair during repair which may generate an amino acid substitution. Genome editing may also include deleting a gene segment by the simultaneous action of two nucleases on the same DNA strand in order to create a truncation between the two nuclease target sites and repairing the DNA break by NHEJ.

"Heterologous" as used herein with respect to a sequence means a sequence that originates from a foreign species, or, if from the same species, is substantially modified from its native form in composition and/or genomic locus by deliberate human intervention.

"Homology-directed repair" or "HDR" as used interchangeably herein refers to a mechanism in cells to repair double strand DNA lesions when a homologous piece of DNA is present in the nucleus, mostly in G2 and S phase of the cell cycle. HDR uses a donor DNA or donor template to guide repair and may be used to create specific sequence changes to the genome, including the targeted addition of whole genes. If a donor template is provided along with the site specific nuclease, then the cellular machinery will repair the break by homologous recombination, which is enhanced several orders of magnitude in the presence of DNA cleavage. When the homologous DNA piece is absent, non-homologous end joining may take place instead.

The terms "homology" or "similarity" as used herein refer to the degree of sequence similarity between two polypeptides or between two nucleic acid molecules compared by sequence alignment. The degree of homology between two discrete nucleic acid sequences being compared is a function of the number of identical, or matching, nucleotides at comparable positions.

"Identical" or "identity" as used herein in the context of two or more nucleic acids or polypeptide sequences means that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as ClustalW, ClustalX, BLAST®, FASTA or Smith-Waterman.

The term "increase" or "increased" as used herein, refers to an increase of from about 10% to about 99%, or an increase of at least 10%, at least 20%, at least 25%, at least 30%, at least 40%, at least 50%, at least 60%, at least 70%, at least 75%, at least 80%, at least 90%, at least 95%, at least 98%, at least 99%, at least 100%, at least 150%, or at least 200% or more or more of a quantity or an activity, such as but not limited to nitrate levels or TSNA levels.

The term "inhibit" or "inhibited" as used herein, refers to a reduction of from about 98% to about 100%, or a reduction of at least 98%, at least 99%, but particularly of 100%, of a quantity or an activity, such as but not limited to polypeptide activity, transcriptional activity, and/or protein expression.

The term "introduced" as used herein means providing a nucleic acid (e.g., expression construct) or protein into a cell. Introduced includes reference to the incorporation of a nucleic acid into a eukaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

The terms "isolated," "purified" or "biologically pure" as used herein refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated nucleic acid of the present invention is separated from open reading frames that flank the desired gene and encode proteins other than the desired protein. The term "purified" as used herein denotes that a nucleic acid or protein gives rise to essentially one band in an electrophoretic gel. Particularly, it means that the nucleic acid or protein is at least 85% pure, more preferably at least 95% pure, and most preferably at least 99% pure.

Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Nitrate reductase" as used herein refers to an enzyme that reduced nitrate ($NO_3^-$) to nitrite ($NO_2^-$). The term "deregulated nitrate reductase enzyme" typically refers to a nitrate reductase enzyme which is not subject to one or more regulatory mechanisms (e.g. transcriptional, post-transcriptional or post-translational regulatory mechanisms) which control or restrict nitrate reductase expression or activity in a control unmodified tobacco plant. Thus "expression or activity of said nitrate reductase is deregulated" typically means that nitrate reductase expression or activity is increased in the modified tobacco plant compared to a control unmodified tobacco plant. The term "deregulated nitrate reductase polynucleotide" includes polynucleotides encoding a modified nitrate reductase (NR) from *Nicotiana tabacum* and includes polynucleotides comprising, consisting or consisting essentially of polynucleotides with substantial homology (that is, sequence similarity) or substantial identity to SEQ ID NOs: 5 or 7 polynucleotide variants that have at least about 60%, 61%, 62%, 63% 64%, 65%, 66%, 67%, 68%, 69%, 70%, 75%, 80%, 85%, 87%, 88%, 89%, 90%, 91%, 92%, 93%, 94%, 95% 96%, 97%, 98% or 99% sequence identity to the sequence of SEQ ID NOs: 5 or 7; fragments of the polynucleotides including fragments of SEQ ID NOs: 5 or 7; and fragments of SEQ ID NOs: 5 or 7 with substantial homology (that is, sequence similarity) or substantial identity thereto that have at least about 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99% or 100% sequence identity to the corresponding fragments of SEQ ID NOs: 5 or 7. The fragments may be at least about 20, 50, 70, 100, 200, 300, 500, 1000, or 2000 nucleotides in length, e.g. the deregulated nitrate reductase polynucleotide may comprise (i) at least about 20, 50, 70, 100, 200, 300, 500, 1000, or 2000 nucleotides of SEQ ID NOs: 5 or 7, or (ii) a sequence having at least about 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99% or 100% sequence identity to at least about 20, 50, 70, 100, 200, 300, 500, 1000, or 2000 nucleotides of SEQ ID NOs: 5 or 7. Typically the fragment may retain the biological activity of the full length sequence, e.g. the fragment encodes nitrate reductase activity, typically modified or deregulated nitrate reductase activity. The nitrate reductase polynucleotide also includes sequences comprising a sufficient or substantial degree of identity or similarity to SEQ ID NOs: 5 or 7 to encode a polypeptide that functions as a nitrate reductase. In one embodiment, the term "nitrate reductase polynucleotide" refers to a polymer of nucleotides which comprises, consists or consists essentially of a polynucleotide designated herein as SEQ ID NOs: 1 or 3.

The term "deregulated nitrate reductase polypeptide" includes a modified nitrate reductase (NR) from *Nicotiana tabacum* and includes polypeptides comprising, consisting or consisting essentially of polypeptides with substantial homology (that is, sequence similarity) or substantial identity to SEQ ID NOs: 6 or 8, or polypeptide variants that have at least about 60%, 61%, 62%, 63% 64%, 65%, 66%, 67%, 68%, 69%, 70%, 75%, 80%, 85%, 87%, 88%, 89%, 90%, 91%, 92%, 93%, 94%, 95% 96%, 97%, 98% or 99% sequence identity to the sequence of SEQ ID NOs: 6 or 8; fragments of the polypeptides including fragments of SEQ ID NOs: 6 or 8; and fragments of SEQ ID NOs: 6 or 8 with substantial homology (that is, sequence similarity) or substantial identity thereto that have at least about 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99% or 100% sequence identity to the corresponding fragments of SEQ ID NOs: 6 or 8. The fragments may be at least about 10, 30, 50, 100, 200, 300, 400, 500, 600, 700, 800 or 900 amino acid residues in length, e.g. the deregulated nitrate reductase polypeptide may comprise (i) at least about 10, 30, 50, 100, 200, 300, 400, 500, 600, 700, 800 or 900 amino acids of SEQ ID NOs: 6 or 8, or (ii) a sequence having at least about 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99% or 100% sequence identity to at least about 10, 30, 50, 100, 200, 300, 400, 500, 600, 700, 800 or 900 amino acids of SEQ ID NOs: 6 or 8. Typically the fragment may retain the biological activity of the full length sequence, e.g. the fragment comprises nitrate reductase activity, typically modified or deregulated nitrate reductase activity. The nitrate reductase polypeptide also includes sequences comprising a sufficient or substantial degree of identity or similarity to SEQ ID NOs: 6 or 8 that functions as a nitrate reductase. In one embodiment, the term "nitrate reductase polypeptide" refers to a polymer of amino acids which comprises, consists or consists essentially of a polypeptide designated herein as SEQ ID NOs: 2 or 4.

"Non-homologous end joining (NHEJ) pathway" as used herein refers to a pathway that repairs double-strand breaks in DNA by directly ligating the break ends without the need for a homologous template. The template-independent re-ligation of DNA ends by NHEJ is a stochastic, error-prone repair process that introduces random micro-insertions and micro-deletions (indels) at the DNA breakpoint. This method may be used to intentionally disrupt, delete, or alter the reading frame of targeted gene sequences. NHEJ typically uses short homologous DNA sequences called microhomologies to guide repair. These microhomologies are often present in single-stranded overhangs on the end of double-strand breaks. When the overhangs are perfectly compatible, NHEJ usually repairs the break accurately, yet imprecise repair leading to loss of nucleotides may also occur, but is much more common when the overhangs are not compatible. "Nuclease mediated NHEJ" as used herein refers to NHEJ that is initiated after a nuclease cuts double stranded DNA.

"N-terminal truncation" as used herein means a deletion of amino acids at or near the N-terminus. In some embodiments, the deletion of amino acids may occur at the N-terminal end of the polypeptide, i.e., the deletion includes the first amino acid of the transcribed or mature protein. In some embodiments, the deletion of amino acids may occur within the N-terminal end of the polypeptide, i.e., the deletion does not include the first amino acid of the transcribed or mature protein, but occurs within the first half of the polypeptide.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribonucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

The specificity of single-stranded DNA to hybridize complementary fragments is determined by the "stringency" of the reaction conditions (Sambrook et al., Molecular Cloning and Laboratory Manual, Second Ed., Cold Spring Harbor (1989)). Hybridization stringency increases as the propensity to form DNA duplexes decreases. In nucleic acid hybridization reactions, the stringency can be chosen to favor specific hybridizations (high stringency), which can be used to identify, for example, full-length clones from a library. Less-specific hybridizations (low stringency) can be used to identify related, but not exact (homologous, but not identical), DNA molecules or segments.

DNA duplexes are stabilized by: (1) the number of complementary base pairs; (2) the type of base pairs; (3) salt concentration (ionic strength) of the reaction mixture; (4) the temperature of the reaction; and (5) the presence of certain organic solvents, such as formamide, which decrease DNA duplex stability. In general, the longer the probe, the higher the temperature required for proper annealing. A common approach is to vary the temperature; higher relative temperatures result in more stringent reaction conditions.

To hybridize under "stringent conditions" describes hybridization protocols in which nucleotide sequences at least 60% homologous to each other remain hybridized. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. Since the target sequences are generally present at excess, at Tm, 50% of the probes are occupied at equilibrium.

"Stringent hybridization conditions" are conditions that enable a probe, primer, or oligonucleotide to hybridize only to its target sequence (e.g., SEQ ID NOs: 1, 3, 5, or 7). Stringent conditions are sequence-dependent and will differ. Stringent conditions comprise: (1) low ionic strength and high temperature washes, for example 15 mM sodium chloride, 1.5 mM sodium citrate, 0.1% sodium dodecyl sulfate, at 50° C.; (2) a denaturing agent during hybridization, e.g. 50% (v/v) formamide, 0.1% bovine serum albumin, 0.1% Ficoll, 0.1% polyvinylpyrrolidone, 50 mM sodium phosphate buffer (750 mM sodium chloride, 75 mM sodium citrate; pH 6.5), at 42° C.; or (3) 50% formamide. Washes typically also comprise 5×SSC (0.75 M NaCl, 75 mM sodium citrate), 50 mM sodium phosphate (pH 6.8), 0.1% sodium pyrophosphate, 5×Denhardt's solution, sonicated salmon sperm DNA (50 µg/mL), 0.1% SDS, and 10% dextran sulfate at 42° C., with a wash at 42° C. in 0.2×SSC (sodium chloride/sodium citrate) and 50% formamide at 55° C., followed by a high-stringency wash consisting of 0.1× SSC containing EDTA at 55° C. Preferably, the conditions are such that sequences at least about 65%, 70%, 75%, 85%, 90%, 95%, 98%, or 99% homologous to each other typically remain hybridized to each other. These conditions are presented as examples and are not meant to be limiting.

"Moderately stringent conditions" use washing solutions and hybridization conditions that are less stringent, such that a polynucleotide will hybridize to the entire, fragments, derivatives, or analogs of the target sequence (e.g., SEQ ID NOs: 1, 3, 5, or 7). One example comprises hybridization in 6×SSC, 5×Denhardt's solution, 0.5% SDS and 100 µg/mL denatured salmon sperm DNA at 55° C., followed by one or more washes in 1×SSC, 0.1% SDS at 37° C. The temperature, ionic strength, etc., can be adjusted to accommodate experimental factors such as probe length. Other moderate stringency conditions have been described (Ausubel et al., Current Protocols in Molecular Biology, Volumes 1-3, John Wiley & Sons, Inc., Hoboken, N.J. (1993); Kriegler, Gene Transfer and Expression: A Laboratory Manual, Stockton Press, New York, N.Y. (1990); Perbal, A Practical Guide to Molecular Cloning, 2nd edition, John Wiley & Sons, New York, N.Y. (1988)).

"Low stringent conditions" use washing solutions and hybridization conditions that are less stringent than those for moderate stringency, such that a polynucleotide will hybridize to the entire, fragments, derivatives, or analogs of the target sequence (e.g., SEQ ID NOs: 1, 3, 5, or 7). A nonlimiting example of low stringency hybridization conditions includes hybridization in 35% formamide, 5×SSC, 50 mM Tris HCl (pH 7.5), 5 mM EDTA, 0.02% PVP, 0.02% Ficoll, 0.2% BSA, 100 µg/mL denatured salmon sperm DNA, 10% (wt/vol) dextran sulfate at 40° C., followed by one or more washes in 2×SSC, 25 mM Tris HCl (pH 7.4), 5 mM EDTA, and 0.1% SDS at 50° C. Other conditions of low stringency, such as those for cross-species hybridizations, are well-described (Ausubel et al., 1993; Kriegler, 1990).

"Operably linked" as used herein means that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function. "Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

The term "plant" as used herein refers to any plant at any stage of its life cycle or development, and its progenies. In one embodiment, the plant is a tobacco plant, which refers to a plant belonging to the genus *Nicotiana*. "Plant" includes reference to whole plants, plant organs, plant tissues, plant propagules, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores. Preferred species, cultivars, hybrids and varieties of tobacco plant are described herein.

"Polynucleotide", "nucleic acid sequence", "nucleotide sequence", or "nucleic acid fragment" are used interchangeably herein to refer to a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide. A polynucleotide can be, without limitation, a genomic DNA, complementary DNA (cDNA), mRNA, or antisense RNA or a fragment(s) thereof. Moreover, a polynucleotide can be single-stranded or double-stranded, nucleic acid that is a mixture of single-stranded and double-stranded regions, a hybrid molecule comprising DNA and RNA, or a hybrid molecule with a mixture of single-stranded and double-stranded regions or a fragment(s) thereof. In addition, the polynucleotide can be composed of triple-stranded regions comprising DNA, RNA, or both or a fragment(s) thereof. A polynucleotide can contain one or more modified bases, such as phosphothioates, and can be a peptide nucleic acid (PNA). Generally, polynucleotides can be assembled from isolated or cloned fragments of cDNA, genomic DNA, oligonucleotides, or individual nucleotides, or a combination of the foregoing. Although the polynucleotide sequences described herein are shown as DNA sequences, the sequences include their corresponding RNA sequences, and their complementary (for example, completely complementary) DNA or RNA sequences, including the reverse complements thereof.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Promoter" as used herein means a synthetic or naturally-derived molecule which is capable of conferring, activating or enhancing expression of a nucleic acid in a cell. A "promoter" refers to a nucleic acid element/sequence, typically positioned upstream and operably-linked to a double-stranded nucleic acid fragment. Promoters can be derived entirely from regions proximate to a native gene of interest, or can be composed of different elements derived from different native promoters or synthetic nucleic acid segments. A promoter may comprise one or more specific transcriptional regulatory sequences to further enhance expression and/or to alter the spatial expression and/or temporal expression of same. A promoter may also comprise distal enhancer or repressor elements, which may be located as much as several thousand base pairs from the start site of transcription. A promoter may be derived from sources including viral, bacterial, fungal, plants, insects, and animals. A promoter may regulate the expression of a gene component constitutively or differentially with respect to cell, the tissue or organ in which expression occurs or, with respect to the developmental stage at which expression occurs, or in response to external stimuli such as physiological stresses, pathogens, metal ions, or inducing agents. "Tissue-specific promoter" and "tissue-preferred promoter" as used interchangeably herein refer to a promoter that is expressed predominantly but not necessarily exclusively in one tissue or organ, but that may also be expressed in one specific cell. "Developmentally regulated promoter" as used herein refers to a promoter whose activity is determined by developmental events. Promoters that cause a gene to be expressed in most cell types at most times are commonly referred to as "constitutive promoters". Inducible promoters selectively express an operably linked DNA sequence in response to the presence of an endogenous or exogenous stimulus, for example by chemical compounds (chemical inducers) or in response to environmental, hormonal, chemical, and/or developmental signals. Examples of inducible or regulated promoters include, but are not limited to, promoters regulated by light, heat, stress, flooding or drought, pathogens, phytohormones, wounding, or chemicals such as ethanol, jasmonate, salicylic acid, or safeners.

"Recombinant" as used herein refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" as used herein refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature. The terms "recombinant DNA construct" and "recombinant construct" are used interchangeably herein.

The term "reduce" or "reduced" as used herein, refers to a reduction of from about 10% to about 99%, or a reduction of at least 10%, at least 20%, at least 25%, at least 30%, at least 40%, at least 50%, at least 60%, at least 70%, at least 75%, at least 80%, at least 90%, at least 95%, at least 98%, at least 99%, or at least 100% or more of a quantity or an activity, such as but not limited to nitrate levels and tobacco-specific nitrosamines (TSNA) levels. The term "reduced," or the phrase "a reduced amount" is intended to refer to an amount TSNA in a modified tobacco plant or a tobacco product generated from the modified tobacco plant that is less than what would be found in a tobacco plant or a tobacco product from the same variety of tobacco processed in the same manner, which has not been modified. Thus, in some contexts, wild-type tobacco of the same variety that has been processed in the same manner is used as a control by which to measure whether a reduction in nitrate or TSNA has been obtained by the inventive methods described herein.

"Regulatory sequences" and "regulatory elements" as used interchangeably herein refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

"Site-specific nuclease" as used herein refers to an enzyme capable of specifically recognizing and cleaving DNA sequences. The site-specific nuclease may be engineered. Examples of engineered site-specific nucleases include zinc finger nucleases (ZFNs), TAL effector nucleases (TALENs), CRISPR/Cas9-based systems, and meganucleases.

The term "tobacco", in some contexts, as used herein is used in a collective sense to refer to tobacco crops, (e.g., a plurality of tobacco plants grown in the field, i.e., not hydroponically grown tobacco) tobacco plants and parts thereof, including but not limited to, roots, stems, leaves, flowers, and seeds prepared and/or obtained, as described herein. It is understood that "tobacco" refers to *Nicotiana tabacum* plants and products thereof. The term "tobacco products" in some contexts refers to consumer tobacco products, including but not limited to, smoking materials (e.g., cigarettes, cigars, and pipe tobacco), snuff, chewing tobacco, gum, and lozenges, as well as components, materials and ingredients for manufacture of consumer tobacco products. Preferably these tobacco products are manufactured from tobacco (*Nicotiana tabacum*) leaves and stems harvested from the tobacco treated as described above and cut, dried, cured, and/or fermented according to conventional techniques in tobacco preparation.

"Transcription terminator", "termination sequences", or "terminator" as used herein refer to DNA sequences located downstream of a coding sequence, including polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"Transgenic" as used herein refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Transgenic plant" as used herein includes reference to a plant which comprises within its genome a heterologous polynucleotide, i.e., a plant or tree that contains recombinant genetic material not normally found in plants or trees of this type and which has been introduced into the plant in question (or into progenitors of the plant) by human manipulation. For example, the heterologous polynucleotide is stably integrated within the genome such that the polynucleotide is passed on to successive generations. The heterologous polynucleotide may be integrated into the genome alone or as part of a recombinant DNA construct. The commercial development of genetically improved germplasm has also advanced to the stage of introducing multiple traits into crop plants, often referred to as a gene stacking approach. In this approach, multiple genes conferring different characteristics of interest can be introduced into a plant. Gene stacking can be accomplished by many means including but not limited to co-transformation, retransformation, and crossing lines with different transgenes. Thus, a plant that is grown from a plant cell into which recombinant DNA is introduced by transformation is a transgenic plant, as are all offspring of that plant that contain the introduced transgene (whether produced sexually or asexually). It is understood that the term transgenic plant encompasses the entire plant or tree and parts of the plant or tree, for instance grains, seeds, flowers, leaves, roots, fruit, pollen, stems etc.

"Transgenic plant" also includes reference to plants which comprise more than one heterologous polynucleotide within their genome. Each heterologous polynucleotide may confer a different trait to the transgenic plant.

"Transcription activator-like effector" or "TALE" as used herein refers to a protein structure that recognizes and binds to a particular DNA sequence. The "TALE DNA-binding domain" refers to a DNA-binding domain that includes an array of tandem 33-35 amino acid repeats, also known as RVD modules, each of which specifically recognizes a single base pair of DNA. RVD modules may be arranged in any order to assemble an array that recognizes a defined sequence.

A binding specificity of a TALE DNA-binding domain is determined by the RVD array followed by a single truncated repeat of 20 amino acids. A TALE DNA-binding domain may have 12 to 27 RVD modules, each of which contains an RVD and recognizes a single base pair of DNA. Specific RVDs have been identified that recognize each of the four possible DNA nucleotides (A, T, C, and G). Because the TALE DNA-binding domains are modular, repeats that recognize the four different DNA nucleotides may be linked together to recognize any particular DNA sequence. These targeted DNA-binding domains may then be combined with catalytic domains to create functional enzymes, including artificial transcription factors, methyltransferases, integrases, nucleases, and recombinases.

"Transcription activator-like effector nucleases" or "TALENs" as used interchangeably herein refers to engineered fusion proteins of the catalytic domain of a nuclease, such as endonuclease FokI, and a designed TALE DNA-binding domain that may be targeted to a custom DNA sequence. A "TALEN monomer" refers to an engineered fusion protein with a catalytic nuclease domain and a designed TALE DNA-binding domain. Two TALEN monomers may be designed to target and cleave a TALEN target region.

"Transgene" as used herein refers to a gene or genetic material containing a gene sequence that has been isolated from one organism and is introduced into a different organism. This non-native segment of DNA may retain the ability to produce RNA or protein in the transgenic organism, or it may alter the normal function of the transgenic organism's genetic code. The introduction of a transgene has the potential to change the phenotype of an organism.

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change.

The term "variety" as used herein refers to a population of plants that share constant characteristics which separate them from other plants of the same species. While possessing one or more distinctive traits, a variety is further characterized by a very small overall variation between individuals within that variety. A variety is often sold commercially.

"Vector" as used herein means refers to a nucleic acid vehicle that comprises a combination of nucleic acid components for enabling the transport of nucleic acid, nucleic acid constructs and nucleic acid conjugates and the like. A vector may be a viral vector, bacteriophage, bacterial artificial chromosome or yeast artificial chromosome. A vector may be a DNA or RNA vector. Suitable vectors include episomes capable of extra-chromosomal replication such as circular, double-stranded nucleic acid plasmids; linearized double-stranded nucleic acid plasmids; and other vectors of any origin. For example, the vector may encode a deregulated nitrate reductase protein comprising the amino acid sequence of any one of SEQ ID NOs: 5 or 7. An "expression vector" as used herein is a nucleic acid vehicle that comprises a combination of nucleic acid components for enabling the expression of nucleic acid, nucleic acid constructs and nucleic acid conjugates and the like. Suitable expression vectors include episomes capable of extra-chromosomal replication such as circular, double-stranded nucleic acid plasmids; linearized double-stranded nucleic acid plasmids; and other functionally equivalent expression vectors of any origin. An expression vector comprises at least a promoter positioned upstream and operably-linked to a nucleic acid, nucleic acid constructs or nucleic acid conjugate, as defined below.

"Zinc finger" as used herein refers to a protein structure that recognizes and binds to DNA sequences. The zinc finger domain is the most common DNA-binding motif in the human proteome. A single zinc finger contains approximately 30 amino acids and the domain typically functions by binding 3 consecutive base pairs of DNA via interactions of a single amino acid side chain per base pair.

"Zinc finger nuclease" or "ZFN" as used interchangeably herein refers to a chimeric protein molecule comprising at least one zinc finger DNA binding domain effectively linked to at least one nuclease or part of a nuclease capable of cleaving DNA when fully assembled.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event however of any latent ambiguity, definitions provided herein take precedent over any dictionary or extrinsic definition. Further, unless otherwise required by context, singular terms shall include pluralities and plural terms shall include the singular.

2. Modified Tobacco Plant with Reduced Nitrate

The present invention is directed, in one aspect, to modified tobacco plants having reduced free nitrate levels in its leaves. The free nitrate levels are reduced via the Nitrate Assimilation Pathway. A simplified diagram of the nitrogen assimilation pathway in plants is shown in FIG. 1. After plants are exposed to soil nitrate, there are several steps involved in the incorporation of N, including uptake, assimilation, translocation and remobilization. Following uptake by specific transporters located on root cell membranes, nitrate enters a specific pathway of assimilation. Initially, the nitrate is reduced to nitrite ($NO_2^-$) by the enzyme nitrate reductase (NR; EC 1.7.1.1-3). Subsequently, nitrite is reduced to ammonia by the nitrite reductase (NiR) enzyme. The latter step tends to be highly efficient in plants, and as a result, plant cells typically contain very low levels of nitrite. After the reduction of nitrite to ammonia, the enzyme glutamine synthetase (GS) incorporates the nitrogen into the organic molecule glutamine (Gln). The GS enzyme works in conjunction with the enzyme glutamate synthase (GOGAT) to form the GS/GOGAT cycle, which functions to shuttle amino groups from Gln to glutamic acid (Glu) to serve as a gateway for the subsequent redistribution of the nitrogen to other amino acids and ultimately proteins and other nitrogen-containing macromolecules. Another important step in this process is catalyzed by isocitrate dehydrogenase (ICDH), the enzyme that is believed to be responsible for providing the 2-oxoglutarate carbon skeleton required by GOGAT to produce Glu.

Tobacco (*Nicotiana tabacum*) has two highly homologous tobacco NR genes, designated Nia1 and Nia2. The modified tobacco plants as disclosed herein that have reduced free nitrate levels in its leaves have a modified nitrate reductase polynucleotide encoding a deregulated nitrate reductase polypeptide, i.e., a deregulated Nia1 and Nia2 gene product. Nitrate reductase is highly regulated at both the transcriptional and post-transcriptional levels. Because of the post-translational regulatory mechanisms, which include light/dark regulation via phosphorylation, the overexpression of NR genes in transgenic plants typically leads to only modest increases in NR activity in the cell. In some embodiments, the deregulated nitrate reductase polypeptide is an endogenous or heterologous nitrate reductase polypeptide that is constitutively active. The deregulated nitrate reductase polypeptide may have lost the ability to be regulated by phosphorylation because of a loss of a phosphorylation site within the nitrate reductase polypeptide and thus is not regulated by light and dark. The modified tobacco plant may have a polynucleotide encoding a deregulated nitrate reductase polypeptide or a deregulated nitrate reductase polypeptide of SEQ ID NO: 5 or SEQ ID NO: 7, or variants or fragments thereof. For example, the deregulated nitrate reductase may be a truncated nitrate reductase polypeptide or a nitrate reductase polypeptide having an amino acid substitution wherein the phosphorylation site is eliminated.

In some embodiments, the modified tobacco plant shows substantially normal plant growth and development, compared to an unmodified control plant. For instance, the modified tobacco plant may senesce normally, i.e. senescence in the modified tobacco plant may be substantially the same as in the unmodified control tobacco plant. In some embodiments, the visual appearance of the modified tobacco plant may be substantially the same as the unmodified control plant, e.g. 3 or 6 months after field transplant. For example, the chlorophyll content of leaves, coloration of leaves, degree of maturity, number of leaves per plant, stalk height, leaf insertion angle, leaf size (width or length), internode distance and/or lamina-midrib ratio may be substantially the same in modified tobacco plants compared to unmodified control plants.

(1) Truncated Nitrate Reductase

The deregulated nitrate reductase polypeptide may be a nitrate reductase polypeptide with an N-terminal truncation, i.e., a deletion at or near the N-terminus. A truncated tobacco Nia2 gene encoding an NR protein possessing a 56 amino acid deletion in its N-terminal domain has much of the post-translational control of the enzyme abolished. The 56 amino acid deletion enables the nitrate reductase enzyme to be equally active in both the light and dark, compared to the wild type (WT) enzyme that becomes inactivated during dark cycles via phosphorylation. When coupled with a strong constitutive promoter, expression of the truncated nitrate reductase gene may enhance overall N nitrate reductase R activity in the plant, but also deregulated production of glutamine (Gln) and asparagine (Asn).

The deregulated nitrate reductase polypeptide may be a nitrate reductase polypeptide having an N-terminal truncation from about 10 amino acids to about 100 amino acids, about 10 amino acids to about 90 amino acids, about 10 amino acids to about 80 amino acids, about 10 amino acids to about 70 amino acids, about 10 amino acids to about 60 amino acids, about 10 amino acids to about 55 amino acids, about 10 amino acids to about 50 amino acids, about 10 amino acids to about 40 amino acids, about 10 amino acids to about 30 amino acids, about 10 amino acids to about 20 amino acids, about 20 amino acids to about 100 amino acids, about 20 amino acids to about 90 amino acids, about 20 amino acids to about 80 amino acids, about 20 amino acids to about 70 amino acids, about 20 amino acids to about 60 amino acids, about 20 amino acids to about 55 amino acids, about 20 amino acids to about 50 amino acids, about 20 amino acids to about 40 amino acids, about 20 amino acids to about 30 amino acids, about 30 amino acids to about 100 amino acids, about 30 amino acids to about 90 amino acids, about 30 amino acids to about 80 amino acids, about 30 amino acids to about 70 amino acids, about 30 amino acids to about 60 amino acids, about 30 amino acids to about 55 amino acids, about 30 amino acids to about 50 amino acids, about 30 amino acids to about 40 amino acids, about 40 amino acids to about 100 amino acids, about 40 amino acids to about 90 amino acids, about 40 amino acids to about 80 amino acids, about 40 amino acids to about 70 amino acids, about 40 amino acids to about 60 amino acids, about 40 amino acids to about 55 amino acids, about 40 amino acids to about 50 amino acids, about 50 amino acids to about 100 amino acids, about 50 amino acids to about 90 amino acids, about 50 amino acids to about 80 amino acids, about 50 amino acids to about 70 amino acids, about 50 amino acids to about 60 amino acids, about 50 amino acids to about 55 amino acids, about 55 amino acids to about 100 amino acids, about 55 amino acids to about 90 amino acids, about 55 amino acids to about 80 amino acids, about 55 amino acids to about 70 amino acids, or about 55 amino acids to about 60 amino acids, or at least about 10 amino acids, at least about 20 amino acids, at least about 30 amino acids, at least about 40 amino acids, at least about 50 amino acids, at least 51 amino acids, at least about 52 amino acids, at least 53 amino acids, at least about 54 amino acids, at least 55 amino acids, at least about 56 amino acids, at least 57 amino acids, at least about 58 amino acids, at least 59 amino acids, at least about 60 amino acids, or at least 65 amino acids as compared to SEQ ID NO: 4. The deregulated nitrate reductase polypeptide may be a nitrate reductase polypeptide having a 56 amino acid N-terminal truncation.

(2) Amino Acid Substitution

The deregulated nitrate reductase polypeptide may be a nitrate reductase polypeptide having an amino acid substitution at position corresponding to position 523 of SEQ ID NO: 4. Mutating the serine residue in a putative phosphorylation site (see FIG. 2), thus eliminating post-translational regulatory controls via light and dark, increases and maintains high levels of active form of nitrate reductase in transgenic plants to facilitate nitrate assimilation. By changing the serine (Ser) residue at position 523 to an aspartate (Asp) of SEQ ID NO: 4 using site-directed mutagenesis, the nitrate reductase polypeptide no longer serves as a substrate for the protein kinases that normally inactive this enzyme during that dark via the phosphorylation of this Ser residue. In some embodiments, the deregulated nitrate reductase includes a polypeptide comprising an amino acid substitution at a position corresponding to position 523 of SEQ ID NO: 4. In some embodiments, the deregulated nitrate reductase includes a polypeptide comprising an amino acid other than serine at a position corresponding to position 523 of SEQ ID NO: 4. In some embodiments, the deregulated nitrate reductase includes a polypeptide comprising an aspartate at a position corresponding to position 523 of SEQ ID NO: 4.

a. Reduced Nitrate Levels

The modified tobacco plants may have reduced nitrate levels compared to a control tobacco plant, such as a wild-type tobacco plant control. In some embodiments, the modified tobacco plants may have reduced nitrate levels in the leaves when grown with high levels, such as 19 mM nitrate, or medium levels, such as 8 mM nitrate, of nitrate fertilization treatment compared to a control tobacco plant. In some embodiments, the modified tobacco plants may have reduced nitrate levels in the leaves when grown under field conditions compared to a control tobacco plant. In some embodiments, the leaves are freshly harvested. In some embodiments, the leaves are cured, stored, or processed. In some embodiments, the leaves are air-cured.

The modified tobacco plants may have at least about a 1-fold reduction, at least about a 2-fold reduction, at least about a 3-fold reduction, at least about a 4-fold reduction, at least about a 5-fold reduction, at least about a 6-fold reduction, at least about a 7-fold reduction, at least about a 8-fold reduction, at least about a 9-fold reduction, at least about a 10-fold reduction, at least about a 15-fold reduction, at least about a 20-fold reduction, at least about a 25-fold reduction, or at least about a 30-fold reduction in nitrate levels in freshly harvest leaves from a modified tobacco plant grown in high levels of nitrate fertilization treatment compared to freshly harvest leaves from a control tobacco. The freshly harvest leaves from modified tobacco plants may have from about 0.5% to about 99%, about 0.5% to about 95%, about 0.5% to about 90%, about 0.5% to about 85%, about 0.5% to about 80%, about 0.5% to about 75%, about 0.5% to about 70%, about 0.5% to about 65%, about 0.5% to about 60%, about 0.5% to about 55%, about 0.5% to about 50%, about 0.5% to about 45%, about 0.5% to about 40%, about 0.5% to about 35%, about 0.5% to about 30%, about 0.5% to about 25%, about 0.5% to about 20%, about 0.5% to about 15%, about 0.5% to about 13%, about 0.5% to about 10%, about 0.5% to about 5%, about 1% to about 99%, about 1% to about 95%, about 1% to about 90%, about 1% to about 85%, about 1% to about 80%, about 1% to about 75%, about 1% to about 70%, about 1% to about 65%, about 1% to about 60%, about 1% to about 55%, about 1% to about 50%, about 1% to about 45%, about 1% to about 40%, about 1% to about 35%, about 1% to about 30%, about 1% to about 25%, about 1% to about 20%, about 1% to about 15%, about 1% to about 13%, about 1% to about 10%, about 1% to about 5%, about 5% to about 99%, about 5% to about 95%, about 5% to about 90%, about 5% to about 85%, about 5% to about 80%, about 5% to about 75%, about 5% to about 70%, about 5% to about 65%, about 5% to about 60%, about 5% to about 55%, about 5% to about 50%, about 5% to about 45%, about 5% to about 40%, about 5% to about 35%, about 5% to about 30%, about 5% to about 25%, about 5% to about 20%, about 5% to about 15%, about 5% to about 13%, about 5% to about 10%, about 10% to about 99%, about 10% to about 95%, about 10% to about 90%, about 10% to about 85%, about 10% to about 80%, about 10% to about 75%, about 10% to about 70%, about 10% to about 65%, about 10% to about 60%, about 10% to about 55%, about 10% to about 50%, about 10% to about 45%, about 10% to about 40%, about 10% to about 35%, about 10% to about 30%, about 10% to about 25%, about 10% to about 20%, about 10% to about 15%, about 10% to about 13%, about 20% to about 99%, about 20% to about 95%, about 20% to about 90%, about 20% to about 85%, about 20% to about 80%, about 20% to about 75%, about 20% to about 70%, about 20% to about 65%, about 20% to about 60%, about 20% to about 55%, about 20% to about 50%, about 20% to about 45%, about 20% to about 40%, about 20% to about 35%, about 20% to about 30%, about 20% to about 25%, about 30% to about 99%, about 30% to about 95%, about 30% to about 90%, about 30% to about 85%, about 30% to about 80%, about 30% to about 75%, about 30% to about 70%, about 30% to about 65%, about 30% to about 60%, about 30% to about 55%, about 30% to about 50%, about 30% to about 45%, about 30% to about 40%, about 30% to about 35%, about 40% to about 99%, about 40% to about 95%, about 40% to about 90%, about 40% to about 85%, about 40% to about 80%, about 40% to about 75%, about 40% to about 70%, about 40% to about 65%, about 40% to about 60%, about 40% to about 55%, about 40% to about 50%, about 40% to about 45%, about 50% to about 99%, about 50% to about 95%, about 50% to about 90%, about 50% to about 85%, about 50% to about 80%, about 50% to about 75%, about 50% to about 70%, about 50% to about 65%, about 50% to about 60%, about 50% to about 55%, about 60% to about 99%, about 60% to about 95%, about 60% to about 90%, about 60% to about 85%, about 60% to about 80%, about 60% to about 75%, about 60% to about 70%, about 60% to about 65%, or at least about 0.5%, at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% the nitrate levels found in freshly harvest leaves from control tobacco plants, such as a wild-type tobacco plant, when grown in high levels of nitrate fertilization treatment. The modified tobacco plants may have at least about 50 ppm, at least about 100 ppm, at least about 500 ppm, at least about 1000 ppm, at least about 1500 ppm, at least about 2000 ppm, at least about 2500 ppm, at least about 3000 ppm, at least about 3500 ppm, at least about 4000 ppm, or at least about 5000 ppm of nitrate in freshly harvest leaves from a modified tobacco plant grown in medium levels of nitrate fertilization treatment compared to freshly harvest leaves from a control tobacco.

The modified tobacco plants may have at least about a 1-fold reduction, at least about a 2-fold reduction, at least about a 3-fold reduction, at least about a 4-fold reduction, at least about a 5-fold reduction, at least about a 6-fold reduction, at least about a 7-fold reduction, at least about a 8-fold reduction, at least about a 9-fold reduction, at least about a 10-fold reduction, at least about a 15-fold reduction, at least about a 20-fold reduction, at least about a 25-fold reduction, or at least about a 30-fold reduction in nitrate levels in freshly harvest leaves from a modified tobacco plant grown in medium levels of nitrate fertilization treatment compared to freshly harvest leaves from a control tobacco. The freshly harvest leaves from modified tobacco plants may have from about 0.5% to about 99%, about 0.5% to about 95%, about 0.5% to about 90%, about 0.5% to about 85%, about 0.5% to about 80%, about 0.5% to about 75%, about 0.5% to about 70%, about 0.5% to about 65%, about 0.5% to about 60%, about 0.5% to about 55%, about 0.5% to about 50%, about 0.5% to about 45%, about 0.5% to about 40%, about 0.5% to about 35%, about 0.5% to about 30%, about 0.5% to about 25%, about 0.5% to about 20%, about 0.5% to about 15%, about 0.5% to about 13%, about 0.5% to about 10%, about 0.5% to about 5%, about 1% to about 99%, about 1% to about 95%, about 1% to about 90%, about 1% to about 85%, about 1% to about 80%, about 1% to about 75%, about 1% to about 70%, about 1% to about 65%, about 1% to about 60%, about 1% to about 55%, about 1% to about 50%, about 1% to about 45%, about 1% to about 40%, about 1% to about 35%, about 1% to about 30%, about 1% to about 25%, about 1% to about 20%, about 1% to about 15%, about 1% to about 13%, about 1% to about 10%, about 1% to about 5%, about 5% to about 99%, about 5% to about 95%, about 5% to about 90%, about 5% to about 85%, about 5% to about 80%, about 5% to about 75%, about 5% to about 70%, about 5% to about 65%, about 5% to about 60%, about 5% to about 55%, about 5% to about 50%, about 5% to about 45%, about 5% to about 40%, about 5% to about 35%, about 5% to about 30%, about 5% to about 25%, about 5% to about 20%, about 5% to about 15%, about 5% to about 13%, about 5% to about 10%, about 10% to about 99%, about 10% to about 95%, about 10% to about 90%, about 10% to about 85%, about 10% to about 80%, about 10% to about 75%, about 10% to about 70%, about 10% to about 65%, about 10% to about 60%, about 10% to about 55%, about 10% to about 50%, about 10% to about 45%, about 10% to about 40%, about 10% to about 35%, about 10% to about 30%, about 10% to about 25%, about 10% to about 20%, about 10% to about 15%, about 10% to about 13%, about 20% to about 99%, about 20% to about 95%, about 20% to about 90%, about 20% to about 85%, about 20% to about 80%, about 20% to about 75%, about 20% to about 70%, about 20% to about 65%, about 20% to about 60%, about 20% to about 55%, about 20% to about 50%, about 20% to about 45%, about 20% to about 40%, about 20% to about 35%, about 20% to about 30%, about 20% to about 25%, about 30% to about 99%, about 30% to about 95%, about 30% to about 90%, about 30% to about 85%, about 30% to about 80%, about 30% to about 75%, about 30% to about 70%, about 30% to about 65%, about 30% to about 60%, about 30% to about 55%, about 30% to about 50%, about 30% to about 45%, about 30% to about 40%, about 30% to about 35%, about 40% to about 99%, about 40% to about 95%, about 40% to about 90%, about 40% to about 85%, about 40% to about 80%, about 40% to about 75%, about 40% to about 70%, about 40% to about 65%, about 40% to about 60%, about 40% to about 55%, about 40% to about 50%, about 40% to about 45%, about 50% to about 99%, about 50% to about 95%, about 50% to about 90%, about 50% to about 85%, about 50% to about 80%, about 50% to about 75%, about 50% to about 70%, about 50% to about 65%, about 50% to about 60%, about 50% to about 55%, about 60% to about 99%, about 60% to about 95%, about 60% to about 90%, about 60% to about 85%, about 60% to about 80%, about 60% to about 75%, about 60% to about 70%, about 60% to about 65%, or at least about 0.5%, at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 25%, at least about 30%, at least about 35%, at least about 37%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% the nitrate levels found in freshly harvest leaves from control tobacco plants, such as a wild-type tobacco plant when grown in medium levels of nitrate fertilization treatment. The modified tobacco plants may have at least about 50 ppm, at least about 100 ppm, at least about 150 ppm, at least about 200 ppm, at least about 250 ppm, at least about 300 ppm, at least about 350 ppm, at least about 400 ppm, at least about 450 ppm, at least about 500 ppm, at least about 550 ppm, at least about 600 ppm, at least about 650 ppm, at least about 700 ppm, at least about 750 ppm, at least about 800 ppm, at least about 850 ppm, at least about 900 ppm, at least about 950 ppm, or at least about 1000 ppm of nitrate in freshly harvest leaves from a modified tobacco plant grown in medium levels of nitrate fertilization treatment compared to freshly harvest leaves from a control tobacco.

The freshly harvested leaves or cured leaves from modified tobacco plants may have at least about a 1-fold reduction, at least about a 2-fold reduction, at least about a 3-fold reduction, at least about a 4-fold reduction, at least about a 5-fold reduction, at least about a 6-fold reduction, at least about a 7-fold reduction, at least about a 8-fold reduction, at least about a 9-fold reduction, at least about a 10-fold reduction, at least about a 15-fold reduction, at least about a 20-fold reduction, at least about a 25-fold reduction, or at least about a 30-fold reduction in nitrate levels in freshly harvest leaves or cured leaves from a modified tobacco plant grown in a field. The freshly harvest leaves or cured leaves from modified tobacco plants may have from about 0.5% to about 99%, about 0.5% to about 95%, about 0.5% to about 90%, about 0.5% to about 85%, about 0.5% to about 80%, about 0.5% to about 75%, about 0.5% to about 70%, about 0.5% to about 65%, about 0.5% to about 60%, about 0.5% to about 55%, about 0.5% to about 50%, about 0.5% to about 45%, about 0.5% to about 40%, about 0.5% to about 35%, about 0.5% to about 30%, about 0.5% to about 25%, about 0.5% to about 20%, about 0.5% to about 15%, about 0.5% to about 13%, about 0.5% to about 10%, about 0.5% to about 5%, about 1% to about 99%, about 1% to about 95%, about 1% to about 90%, about 1% to about 85%, about 1% to about 80%, about 1% to about 75%, about 1% to about 70%, about 1% to about 65%, about 1% to about 60%, about 1% to about 55%, about 1% to about 50%, about 1% to about 45%, about 1% to about 40%, about 1% to about 35%, about 1% to about 30%, about 1% to about 25%, about 1% to about 20%, about 1% to about 15%, about 1% to about 13%, about 1% to about 10%, about 1% to about 5%, about 5% to about 99%, about 5% to about 95%, about 5% to about 90%, about 5% to about 85%, about 5% to about 80%, about 5% to about 75%, about 5% to about 70%, about 5% to about 65%, about 5% to about 60%, about 5% to about 55%, about 5% to about 50%, about 5% to about 45%, about 5% to about 40%, about 5% to about 35%, about 5% to about 30%, about 5% to about 25%, about 5% to about 20%, about 5% to about 15%, about 5% to about 13%, about 5% to about 10%, about 10% to about 99%, about 10% to about 95%, about 10% to about 90%, about 10% to about 85%, about 10% to about 80%, about 10% to about 75%, about 10% to about 70%, about 10% to about 65%, about 10% to about 60%, about 10% to about 55%, about 10% to about 50%, about 10% to about 45%, about 10% to about 40%, about 10% to about 35%, about 10% to about 30%, about 10% to about 25%, about 10% to about 20%, about 10% to about 15%, about 10% to about 13%, about 20% to about 99%, about 20% to about 95%, about 20% to about 90%, about 20% to about 85%, about 20% to about 80%, about 20% to about 75%, about 20% to about 70%, about 20% to about 65%, about 20% to about 60%, about 20% to about 55%, about 20% to about 50%, about 20% to about 45%, about 20% to about 40%, about 20% to about 35%, about 20% to about 30%, about 20% to about 25%, about 30% to about 99%, about 30% to about 95%, about 30% to about 90%, about 30% to about 85%, about 30% to about 80%, about 30% to about 75%, about 30% to about 70%, about 30% to about 65%, about 30% to about 60%, about 30% to about 55%, about 30% to about 50%, about 30% to about 45%, about 30% to about 40%, about 30% to about 35%, about 40% to about 99%, about 40% to about 95%, about 40% to about 90%, about 40% to about 85%, about 40% to about 80%, about 40% to about 75%, about 40% to about 70%, about 40% to about 65%, about 40% to about 60%, about 40% to about 55%, about 40% to about 50%, about 40% to about 45%, about 50% to about 99%, about 50% to about 95%, about 50% to about 90%, about 50% to about 85%, about 50% to about 80%, about 50% to about 75%, about 50% to about 70%, about 50% to about 65%, about 50% to about 60%, about 50% to about 55%, about 60% to about 99%, about 60% to about 95%, about 60% to about 90%, about 60% to about 85%, about 60% to about 80%, about 60% to about 75%, about 60% to about 70%, about 60% to about 65%, or at least about 0.5%, at least about 1.0%, at least about 2.0%, at least about 3.0%, at least about 4.0%, at least about 4.1%, at least about 4.2%, at least about 4.3%, at least about 4.4%, at least about 4.5%, at least about 5.0%, at least about 5.1%, least about 5.2%, at least about 5.3%, least about 5.4%, at least about 5.5%, at least about 5.6%, at least about 5.7%, at least about 5.8%, at least about 5.9%, at least about 6.0%, at least about 7.0%, at least about 8.0%, at least about 9.0%, at least about 10%, at least about 11%, at least about 12%, at least about 13%, at least about 14%, at least about 15%, at least about 16%, at least about 17%, at least about 18%, at least about 19%, at least about 20%, at least about 25%, at least about 30%, at least about 35%, at least about 37%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% the nitrate levels found in freshly harvest leaves or cured leaves from control tobacco plants, such as a wild-type tobacco plant when grown in a field.

b. Heterologous Nitrate Reductase

The deregulated nitrate reductase polypeptide may be encoded by a heterologous nitrate reductase polynucleotide or gene, i.e., a nitrate reductase gene that is not endogenous to the modified tobacco plant. The heterologous nitrate reductase gene may be introduced into the genome of the modified tobacco plant by plant transformation, as described below. For example, the heterologous nitrate reductase gene may be introduced into the modified tobacco plant by stable transformation or transient transformation methods.

The heterologous nitrate reductase gene may be a plant, fungal or algal nitrate reductase gene. For example, the heterologous nitrate reductase gene may be from *Ricinus communis, Ricinus communis, Vitis vinifera, Populus trichocarpa, Selaginella moellendorffii, Selaginella moellendorffii, Cucumis sativus, Cucurbita maxima, Cucumis sativus, Brassica napus, Populus trichocarpa, Betula pendula, Solanum tuberosum, Nicotiana tomentosiformis, Nicotiana tabacum, Solanum lycopersicum, Nicotiana benthamiana, Medicago truncatula, Nicotiana benthamiana, Brassica rapa* subsp. *chinenis, Beta vulgaris, Nicotiana sylvestris,* a different variety of *Nicotiana tabacum, Nicotiana plumbaginifolia, Glycine max, Solanum tuberosum, Solanum tuberosum, Brassica napus, Arabidopsis lyrata* subsp. *lyrata, Arabidopsis thaliana, Phaseolus vulgaris, Medicago truncatula, Petunia* x hybrid, *Spinacia oleracea, Lotus japonicas, Cichorium intybus, Petuniax hybrid, Spinacia oleracea, Thellungiella halophile, Oryza sativa* Japonica Group, *Zea Mays, Arabidopsis thaliana, Arabidopsis lyrata* subsp. *lyrata, Phaseolus vulgaris, Sorghum bicolor, Oryza sativa* Indica Group, *Oryza sativa Japonica* Group, *Hordeum vulgare* subsp *vulgare, Sorghum bicolor, Oryza sativa Japonica* Group, *Glycine max, Hordeum vulgare* subsp. *vulgare, Sorghum bicolor, Zea mays, Heterosignma akashiwo, Chlorella vulgaris* UTEX259, *Chlorella vulgaris* NJ-7, *Chlorella variabilis, Ectocarpus siliculosus, Volvox carteri f. nagariensis, Gracilaria tenuistipitata, Dunaliella tertiolecta, Chlamydomonas reinhardtii, Dunaliella viridis, Thalassiosira pseudonana* CCMP1335, *Dunaliella salina, Phaeodactylum tricornutum,* or *Ostreococcus lucimarinus* CCE9901.

The heterologous nitrate reductase gene may be a nitrate reductase gene having a sequence of GenBank Accession No. XP_002513830.1, AAG30576.1, XP_002285831.1, XP_002307415.1, XP_002984312.1, XP_002972481.1, ADN96689.1, P17569.1, ADK77877.1, P39867.1, XP_002301015.1, P27783.1, BAB93534.1, 227925, P11605.1, P17570.1, BAE46746.1, ADV03139.1, BAE96752.1, ACF93242.1, ABW05098.1, 227926, P08509.2, P39870.1, AAB18985.1, AAB52786.1, P39868.1, XP_002889158.1, NP_177899.1, P39866.1, ADV03138.1, P36859.1, P23312.1, P39869.1, P43101.1, AAA33712.1, BAA13047.1, BAJ33682.1, NP_001062006.1, AAD38068.1, NP_174901.1, XP_002891229.1, P39865.1, XP_002444490.1, EEC74079.1, NP_001048253.1, P27967.1, XP_002454625.1, NP 001062009.1, P54233.1, P27968.1, XP 002454083.1, P49102.1, ACS44801.1, ABP97095.1, ABJ91208.4, EFN52691.1, CBN78746.1, XP_002955156.1, ACX31652.1, AAL79356.1, AAF17595.1, AAT72293.1, XP 002294410.1, AAP75705.1, AAV66996.1, or XP_001420098.1.

c. Modification of Endogenous Nitrate Reductase Gene

Tobacco (*Nicotiana tabacum*) has two highly homologous tobacco NR genes, designated Nia1 and Nia2, i.e., two endogenous nitrate reductase genes. The deregulated nitrate reductase gene may be an endogenous nitrate reductase gene that is modified or mutagenized by a genome editing system or by a mutagen. Mutations in the nucleotide sequences and polypeptides described herein can include man-made mutations or synthetic mutations or genetically engineered mutations. Mutations in the nucleotide sequences and polypeptides described herein can be mutations that are obtained or obtainable via a process which includes an in vitro or an in vivo manipulation step. Mutations in the nucleotide sequences and polypeptides described herein can be mutations that are obtained or obtainable via a process which includes intervention by man.

Processes for preparing mutants are well known in the art and may include mutagenesis using exogenously added chemicals—such as mutagenic, teratogenic, or carcinogenic organic compounds, for example ethyl methanesulfonate (EMS), that produce random mutations in genetic material. By way of further example, the process may include one or more genetic engineering steps—such as one or more of the genetic engineering steps that are described herein or combinations thereof. Targeting Induced Local Lesions in Genomes (TILLING) may also be used as described elsewhere.

By way of further example, the process may include one or more plant crossing steps. In one embodiment, seeds from plants are mutagenised and then grown into first generation mutant plants. The first generation plants are then allowed to self-pollinate and seeds from the first generation plant are grown into second generation plants, which are then screened for mutations in their loci. Though the mutagenized plant material can be screened for mutations, an advantage of screening the second generation plants is that all somatic mutations correspond to germline mutations. One of skill in the art would understand that a variety of plant materials, including but not limited to, seeds, pollen, plant tissue or plant cells, may be mutagenised in order to create the mutant plants. However, the type of plant material mutagenised may affect when the plant nucleic acid is screened for mutations. For example, when pollen is subjected to mutagenesis prior to pollination of a non-mutagenized plant the seeds resulting from that pollination are grown into first generation plants. Every cell of the first generation plants will contain mutations created in the pollen; thus these first generation plants may then be screened for mutations instead of waiting until the second generation.

(1) Genome Editing System

The genome editing system may bind and cleave the endogenous nitrate reductase gene at a location to generate a truncated nitrate reductase polypeptide or a nitrate reductase polypeptide having an amino acid substitution. The endogenous nitrate reductase gene may be modified by a genome editing system that includes a site-specific nuclease that binds and cleaves the endogenous nitrate reductase gene. The genome editing system may utilize nuclease mediated non-homologous end joining or homology-directed repair. The genome editing system may be introduced into the modified tobacco plant by stable transformation or transient transformation methods.

The site-specific nuclease may be engineered. For example, an engineered site-specific nuclease may be a CRISPR/Cas9-based system, a ZFN, or a TALEN. The site-specific nuclease may bind and cleave an endogenous nitrate reductase gene. The genome editing system may be include an engineered CRISPR/Cas System, such as an engineered CRISPR/Cas-9 system, an engineered transcription activator-like effector nuclease, an engineered zinc finger nuclease, or an engineered meganuclease.

(2) Mutagens

Mutagens that create primarily point mutations and short deletions, insertions, transversions, and or transitions, including chemical mutagens or radiation, may be used to create the mutations in the nitrate reductase gene. Mutagens include, but are not limited to, ethyl methanesulfonate, methylmethane sulfonate, N-ethyl-N-nitrosurea, triethylmelamine, N-methyl-N-nitrosourea, procarbazine, chlorambucil, cyclophosphamide, diethyl sulfate, acrylamide monomer, melphalan, nitrogen mustard, vincristine, dimethylnitrosamine, N-methyl-N'-nitro-Nitrosoguanidine, nitrosoguanidine, 2-aminopurine, 7,12 dimethyl-benz(a)anthracene, ethylene oxide, hexamethylphosphoramide, bisulfan, diepoxyalkanes (diepoxyoctane, diepoxybutane, and the like), 2-methoxy-6-chloro-9 [3-(ethyl-2-chloro-ethyl)aminopropylamino]acridine dihydrochloride and formaldehyde.

d. Combination with Alkaloid Precursor Gene

The deregulated nitrate reductase polypeptide, which targets the nitrosating agent, may be used in combination with a modified alkaloid precursor gene, which inhibits the production of the nornicotine alkaloid precursor. The combination of the deregulated nitrate reductase polypeptide and the modified alkaloid precursor gene may produce an even greater reduction in NNN accumulation compared to using deregulated nitrate reductase or modified alkaloid precursor gene alone. The modified alkaloid precursor gene may be reduce a specific TSNA, such as N'-nitrosonornicotine, by reducing the levels of the precursor alkaloid nornicotine to lower low nornicotine. The modified alkaloid precursor gene may be a modified nicotine demethylase gene or a cytochrome P450 gene. The modified alkaloid precursor gene may be a modified CYP82E4 gene, a modified CYP82E5v2 gene, or a modified CYP82E10 gene, and combinations thereof. In some embodiments, the deregulated nitrate reductase polypeptide may be introduced into a tobacco plant that has a knockout mutation in an endogenous nicotine demethylase gene, such as a DH98-325-6#775 breeding line (Lewis et al. Phytochem. 71:1988-1998 (2010)), or a tobacco plant having a triple mutant nicotine demethylase genetic background. In some embodiments, the deregulated nitrate reductase polypeptide may be introduced into a tobacco plant that has knockout mutations in both the CYP82E4 and CYP82E5 nicotine demethylase genes, such as burley cultivar TN90e4e5, which is a line that represents a backcross-derived variant of commercial variety TN90 and is described in U.S. Patent Application No. 20120216822, which is incorporated herein by reference in its entirety.

3. Constructs, Vector, and Expression Vector

In certain embodiments, the polynucleotides to be introduced into the plant are operably linked to a promoter sequence and may be provided as a construct. As used herein, a polynucleotide is "operably linked" when it is placed into a functional relationship with a second polynucleotide sequence. For instance, a promoter is operably linked to a coding sequence if the promoter is connected to the coding sequence such that it may effect transcription of the coding sequence. In various embodiments, the polynucleotides may be operably linked to at least one, at least two, at least three, at least four, at least five, or at least ten promoters.

The nucleic acid sequences may make up a genetic construct that may be a vector. The vector may be capable of expressing the deregulated nitrate reductase polypeptide or the genome editing system in the cell of a plant. The vector may be recombinant. The vector may comprise heterologous nucleic acid encoding the deregulated nitrate reductase polypeptide or the genome editing system. Suitable vectors include plasmids and virus-derived vectors. Vectors known in the art that are suitable for transformation into plants, cloning, and protein expression may be used. The vector may be useful for transfecting cells with nucleic acid encoding the deregulated nitrate reductase polypeptide or the genome editing system, which the transformed host cell is cultured and maintained under conditions wherein expression of the deregulated nitrate reductase polypeptide or the genome editing system takes place.

The genetic constructs may comprise a nucleic acid sequence that encodes the deregulated nitrate reductase polypeptide or the genome editing system disclosed herein. The genetic construct may be present in the cell as a functioning extrachromosomal molecule. The genetic construct may be a linear minichromosome including centromere, telomeres or plasmids or cosmids. The genetic construct may also be part of a genome of a recombinant viral vector, including recombinant cauliflower mosaic virus, recombinant tobacco mosaic virus, and recombinant potato virus X-based vectors. The genetic construct may be part of the genetic material in attenuated live microorganisms or recombinant microbial vectors which live in cells. The genetic constructs may comprise regulatory elements for gene expression of the coding sequences of the nucleic acid. The regulatory elements may be a promoter, an enhancer an initiation codon, a stop codon, or a polyadenylation signal.

The vector may comprise heterologous nucleic acid encoding the deregulated nitrate reductase polypeptide and may further comprise an initiation codon, which may be upstream of the deregulated nitrate reductase polypeptide coding sequence and a stop codon, which may be downstream of the deregulated nitrate reductase polypeptide coding sequence. The initiation and termination codon may be in frame with the deregulated nitrate reductase polypeptide coding sequence. The vector may also comprise a promoter that is operably linked to the deregulated nitrate reductase polypeptide coding sequence. The promoter that is operably linked to the deregulated nitrate reductase polypeptide coding sequence may be not natively associated with the polynucleotide encoding the deregulated nitrate reductase polypeptide. Promoters useful in the practice of the present invention include, but are not limited to, constitutive, inducible, temporally-regulated, developmentally regulated, chemically regulated, tissue-preferred and tissue-specific promoters. Suitably, the promoter causes sufficient expression in the plant to produce the phenotypes described herein. Suitable promoters include, without limitation, the 35S promoter of the cauliflower mosaic virus, CYP82E4 promoter, ubiquitin, tCUP cryptic constitutive promoter, the Rsyn7 promoter, pathogen-inducible promoters, the maize In2-2 promoter, the tobacco PR-1a promoter, glucocorticoid-inducible promoters, and tetracycline-inducible and tetracycline-repressible promoters.

The vector may also comprise a polyadenylation signal, which may be downstream of the deregulated nitrate reductase polypeptide coding sequence. The vector may also comprise an enhancer upstream of the deregulated nitrate reductase polypeptide coding sequence. The enhancer may be necessary for DNA expression. The vector may also comprise a plant origin of replication in order to maintain the vector extrachromosomally and produce multiple copies of the vector in a cell. The vector may also comprise a regulatory sequence, which may be well suited for gene expression in a plant cell into which the vector is administered. The vector may also comprise a reporter gene, such as green fluorescent protein ("GFP") and/or a selectable marker, such as hygromycin ("Hygro").

Coding sequences may be optimized for stability and high levels of expression. In some instances, codons are selected to reduce secondary structure formation of the RNA such as that formed due to intramolecular bonding.

The vector may be expression vectors or systems to produce protein by routine techniques and readily available starting materials including Sambrook et al., 1989, which is incorporated fully by reference. In some embodiments the vector may comprise the nucleic acid sequence encoding the deregulated nitrate reductase polypeptide. The vector may be pBI121.

4. Plant Transformation

The polynucleotide encoding the deregulated nitrate reductase may be introduced into a plant cell to produce a transgenic plant. As used herein, "introduced into a plant" with respect to polynucleotides encompasses the delivery of a polynucleotide into a plant, plant tissue, or plant cell using any suitable polynucleotide delivery method. Methods suitable for introducing polynucleotides into a plant useful in the practice of the present invention include, but are not limited to, freeze-thaw method, microparticle bombardment, direct DNA uptake, electroporation, sonication, microinjection, plant virus-mediated, and *Agrobacterium*-mediated transfer to the plant. Any suitable *Agrobacterium* strain, vector, or vector system for transforming the plant may be employed according to the present invention. In certain embodiments, the polynucleotide is introduced using at least one of stable transformation methods, transient transformation methods, or virus-mediated methods.

By "stable transformation" is intended that the nucleotide construct introduced into a plant integrates into the genome of the plant and is capable of being inherited by progeny thereof. For example, the introduced nucleotide and/or linked selectable marker gene, such as the genome editing system, may be segregated away in subsequent plant generations using conventional breeding techniques.

By "transient transformation" is intended that a nucleotide construct introduced into a plant does not integrate into the genome of the plant. A plant or plant cell may also be transiently transformed such that the recombinant polynucleotide is not integrated into its genome. Transiently transformed cells typically lose all or some portion of the introduced recombinant polynucleotide with each cell division such that the introduced recombinant polynucleotide cannot be detected in daughter cells after a sufficient number of cell divisions. For example, plant cells may be initially be transformed with the genome editing system lacking a selectable marker and may be grown on media lacking a selection agent. Under such conditions, a fraction of the treated cells will acquire the genome editing system and will express the genome editing system transiently without integrating the genome editing system into the genome. Because it does not account for transformation efficiency, this latter transformation procedure requires that a greater number of treated cells be screened to obtain the desired genome modification.

Suitable methods of introducing nucleotide sequences into plant cells and subsequent insertion into the plant genome include microinjection (Crossway et al., Biotechniques 4:320-334 (1986)), electroporation (Riggs et al., Proc. Natl. Acad. Sci. USA 83:5602-5606 (1986)), *Agrobacterium*-mediated transformation (U.S. Pat. Nos. 5,981, 840 and 5,563,055), direct gene transfer (Paszkowski et al., EMBO J. 3:2717-2722 (1984)), and ballistic particle acceleration (see, for example, U.S. Pat. Nos. 4,945,050; 5,879, 918; 5,886,244; 5,932,782; Tomes et al., in Plant Cell, Tissue, and Organ Culture: Fundamental Methods, ed. Gamborg and Phillips (Springer-Verlag, Berlin) (1995); and McCabe et al., Biotechnology 6:923-926 (1988)), all of which are herein incorporated by reference in their entireties.

In some embodiments, a plant may be regenerated or grown from the plant, plant tissue or plant cell. Any suitable methods for regenerating or growing a plant from a plant cell or plant tissue may be used, such as, without limitation, tissue culture or regeneration from protoplasts. Suitably, plants may be regenerated by growing transformed plant cells on callus induction media, shoot induction media and/or root induction media. See, for example, McCormick et al., Plant Cell Reports 5:81-84 (1986). These plants may then be grown, and either pollinated with the same transformed strain or different strains, and the resulting hybrid having expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. Thus as used herein, "transformed seeds" refers to seeds that contain the nucleotide construct stably integrated into the plant genome.

5. Tobacco Varieties

The varieties of tobacco that can be modified according to the disclosed methods include, but are not limited to, dark varieties (e.g., Burley), Flue or Bright varieties (e.g., Virginia flue), Oriental or Turkish varieties, such as Latakia, and genetically modified varieties (e.g., Vector 2141). Burley tobaccos generally accumulate higher levels of nitrate than other tobacco types and tend to contribute towards a disproportionate share of the TSNAs found in the common "American blend" style of cigarettes (which also contains flue-cured and oriental tobaccos).

6. Tobacco Product with Reduced Tobacco Specific Nitrosamines

The present invention is directed, in one aspect, to a tobacco product having reduced tobacco specific nitrosamines (TSNA). TSNA are produced during the tobacco curing process and during smoking. TSNA are formed by a reaction between a nitrosating agent and alkaloids found naturally in tobacco and are also carcinogens in tobacco smoke. The tobacco product is produced from the modified tobacco plant, as described above.

The modified tobacco plants may be freshly harvested, cured, and processed into tobacco products, which exhibit a reduced carcinogenic potential. The leaves may be air-cured, fire cured, flue cured, or sun-cured. Air-cured tobacco is hung in well-ventilated barns and allowed to dry over a period of four to eight weeks. Air-cured tobacco is low in sugar, which gives the tobacco smoke a light, mild flavor, and high in nicotine. Cigar and burley tobaccos are 'Dark' air cured. Fire cured tobacco is hung in large barns where fires of hardwoods are kept on continuous or intermittent low smolder and takes between three days and ten weeks, depending on the process and the tobacco. Fire curing produces a tobacco low in sugar and high in nicotine. Flue cured tobacco was originally strung onto tobacco sticks, which were hung from tier-poles in curing barns. These barns have flues run from externally fed fire boxes, heat-curing the tobacco without exposing it to smoke, slowly raising the temperature over the course of the curing. The process generally takes about a week and produces cigarette tobacco that is high in sugar and has medium to high levels of nicotine. Most cigarettes incorporate flue-cured tobacco, which produces a milder, more inhalable smoke. Sun-cured tobacco dries uncovered in the sun. This method is used in Turkey, Greece and other Mediterranean countries to produce oriental tobacco. Sun-cured tobacco is low in sugar and nicotine and is used in cigarettes.

Tobacco products including, but not limited to, smoking materials (e.g., cigarettes, cigars, pipe tobacco, flavored shisha tobacco), snuff, dipping tobacco, cigarette substitutes, such as nicotine patch, nicotine mouthwash, spray agent packaged in high pressure gas tank with propellant, nicotine chewing gum, and nicotine drink, and lozenges, prepared from said treated modified tobacco plants are also embodiments. Tobacco products that are utilized as e-liquids or nicotine solution for e-cigarettes, personal vaporizer, or electronic nicotine delivery systems are also embodiments.

The tobacco products produced from the modified tobacco plants described herein may have reduced TSNA levels compared to tobacco products produced from a control tobacco plant, such as a wild-type tobacco plant control. In some embodiments, the tobacco products produced from the modified tobacco plants may have reduced total TSNA levels compared to tobacco products produced from a control tobacco plant, such as a wild-type tobacco plant control. In some embodiments, the tobacco products produced from the modified tobacco plants may have reduced levels of at least one TSNA including, but not limited to, N-nitrosonornicotine (NNN), 4-(methylnitrosamino)-1-(3-pyridyl)-1-butanone (NNK), N-nitrosoanabasine (NAB), N-nitrosoanatabine (NAT), and combinations thereof, as compared to tobacco of the same variety and cultivated by conventional techniques or a tobacco product prepared from conventional tobacco.

The tobacco product produced from cured leaves from the modified tobacco plant may have at least about 5.0% reduction, at least about 10.0% reduction, at least about 15.0% reduction, at least about 20.0% reduction, at least about 25.0% reduction, at least about 30.0% reduction, at least about 35.0% reduction, at least about 40.0% reduction, at least about 45.0% reduction, at least about 50.0% reduction, at least about 55.0% reduction, at least about 60.0% reduction, at least about 65.0% reduction, at least about 70.0% reduction, at least about 75.0% reduction, at least about 80.0% reduction, at least about 85.0% reduction, at least about 90.0%, at least about 95.0% reduction, or at least about 99.0% reduction in total TSNA levels compared to a control tobacco product which is produced from cured leaves from a control tobacco plant. The tobacco product produced from cured leaves from the modified tobacco plant may have from about 5.0% to about 99.0%, about 5.0% to about 95.0%, about 5.0% to about 90.0%, about 5.0% to about 85.0%, about 5.0% to about 80.0%, about 5.0% to about 75.0%, about 5.0% to about 70.0%, about 5.0% to about 65.0%, about 5.0% to about 60.0%, about 5.0% to about 55.0%, about 5.0% to about 50.0%, about 5.0% to about 45.0%, about 5.0% to about 40.0%, about 10.0% to about 99.0%, about 10.0% to about 95.0%, about 10.0% to about 90.0%, about 10.0% to about 85.0%, about 10.0% to about 80.0%, about 10.0% to about 75.0%, about 10.0% to about 70.0%, about 10.0% to about 65.0%, about 10.0% to about 60.0%, about 10.0% to about 55.0%, about 10.0% to about 50.0%, about 10.0% to about 45.0%, about 10.0% to about 40.0%, about 20.0% to about 99.0%, about 20.0% to about 95.0%, about 20.0% to about 90.0%, about 20.0% to about 85.0%, about 20.0% to about 80.0%, about 20.0% to about 75.0%, about 20.0% to about 70.0%, about 20.0% to about 65.0%, about 20.0% to about 60.0%, about 20.0% to about 55.0%, about 20.0% to about 50.0%, about 20.0% to about 45.0%, about 20.0% to about 40.0%, about 30.0% to about 99.0%, about 30.0% to about 95.0%, about 30.0% to about 90.0%, about 30.0% to about 85.0%, about 30.0% to about 80.0%, about 30.0% to about 75.0%, about 30.0% to about 70.0%, about 30.0% to about 65.0%, about 30.0% to about 60.0%, about 30.0% to about 55.0%, about 30.0% to about 50.0%, about 30.0% to about 45.0%, about 40.0% to about 99.0%, about 40.0% to about 95.0%, about 40.0% to about 90.0%, about 40.0% to about 85.0%, about 40.0% to about 80.0%, about 40.0% to about 75.0%, about 40.0% to about 70.0%, about 40.0% to about 65.0%, about 40.0% to about 60.0%, about 40.0% to about 55.0%, about 40.0% to about 50.0%, about 50.0% to about 99.0%, about 50.0% to about 95.0%, about 50.0% to about 90.0%, about 50.0% to about 85.0%, about 50.0% to about 80.0%, about 50.0% to about 75.0%, about 50.0% to about 70.0%, about 50.0% to about 65.0%, about 50.0% to about 60.0%, about 50.0% to about 55.0%, about 60.0% to about 99.0%, about 60.0% to about 95.0%, about 60.0% to about 90.0%, about 60.0% to about 85.0%, about 60.0% to about 80.0%, about 60.0% to about 75.0%, about 60.0% to about 70.0%, or about 60.0% to about 65.0% reduction in the total TSNA levels compared a control tobacco product which is produced from cured leaves from a control tobacco plant.

The tobacco product produced from cured leaves from the modified tobacco plant may have at least about 5.0% reduction, at least about 10.0% reduction, at least about 15.0% reduction, at least about 20.0% reduction, at least about 25.0% reduction, at least about 30.0% reduction, at least about 35.0% reduction, at least about 40.0% reduction, at least about 45.0% reduction, at least about 50.0% reduction, at least about 55.0% reduction, at least about 60.0% reduction, at least about 65.0% reduction, at least about 70.0% reduction, at least about 72.0% reduction, at least about 72.5% reduction, at least about 73.0% reduction, at least about 75.0% reduction, at least about 80.0% reduction, at least about 85.0% reduction, at least about 90.0%, at least about 95.0% reduction, or at least about 99.0% reduction in the levels of at least one TSNA including, but not limited to, N-nitrosonornicotine (NNN), 4-(methylnitrosamino)-1-(3-pyridyl)-1-butanone (NNK), N-nitrosoanabasine (NAB), N-nitrosoanatabine (NAT), and combinations thereof, compared a control tobacco product which is produced from cured leaves from a control tobacco plant. The tobacco product produced from cured leaves from the modified tobacco plant may have from about 5.0% to about 99.0%, about 5.0% to about 95.0%, about 5.0% to about 90.0%, about 5.0% to about 85.0%, about 5.0% to about 80.0%, about 5.0% to about 75.0%, about 5.0% to about 70.0%, about 5.0% to about 65.0%, about 5.0% to about 60.0%, about 5.0% to about 55.0%, about 5.0% to about 50.0%, about 5.0% to about 45.0%, about 5.0% to about 40.0%, about 10.0% to about 99.0%, about 10.0% to about 95.0%, about 10.0% to about 90.0%, about 10.0% to about 85.0%, about 10.0% to about 80.0%, about 10.0% to about 75.0%, about 10.0% to about 70.0%, about 10.0% to about 65.0%, about 10.0% to about 60.0%, about 10.0% to about 55.0%, about 10.0% to about 50.0%, about 10.0% to about 45.0%, about 10.0% to about 40.0%, about 20.0% to about 99.0%, about 20.0% to about 95.0%, about 20.0% to about 90.0%, about 20.0% to about 85.0%, about 20.0% to about 80.0%, about 20.0% to about 75.0%, about 20.0% to about 70.0%, about 20.0% to about 65.0%, about 20.0% to about 60.0%, about 20.0% to about 55.0%, about 20.0% to about 50.0%, about 20.0% to about 45.0%, about 20.0% to about 40.0%, about 30.0% to about 99.0%, about 30.0% to about 95.0%, about 30.0% to about 90.0%, about 30.0% to about 85.0%, about 30.0% to about 80.0%, about 30.0% to about 75.0%, about 30.0% to about 70.0%, about 30.0% to about 65.0%, about 30.0% to about 60.0%, about 30.0% to about 55.0%, about 30.0% to about 50.0%, about 30.0% to about 45.0%, about 30.0% to about 40.0%, about 40.0% to about 99.0%, about 40.0% to about 95.0%, about 40.0% to about 90.0%, about 40.0% to about 85.0%, about 40.0% to about 80.0%, about 40.0% to about 75.0%, about 40.0% to about 70.0%, about 40.0% to about 65.0%, about 40.0% to about 60.0%, about 40.0% to about 55.0%, about 40.0% to about 50.0%, about 50.0% to about 99.0%, about 50.0% to about 95.0%, about 50.0% to about 90.0%, about 50.0% to about 85.0%, about 50.0% to about 80.0%, about 50.0% to about 75.0%, about 50.0% to about 70.0%, about 50.0% to about 65.0%, about 50.0% to about 60.0%, about 50.0% to about 55.0%, about 60.0% to about 99.0%, about 60.0% to about 95.0%, about 60.0% to about 90.0%, about 60.0% to about 85.0%, about 60.0% to about 80.0%, about 60.0% to about 75.0%, about 60.0% to about 70.0%, or about 60.0% to about 65.0% in the levels of at least one TSNA including, but not limited to, N-nitrosonornicotine (NNN), 4-(methylnitrosamino)-1-(3-pyridyl)-1-butanone (NNK), N-nitrosoanabasine (NAB), N-nitrosoanatabine (NAT), and combinations thereof compared a control tobacco product which is produced from cured leaves from a control tobacco plant.

7. Cut Filler Tobacco and Tobacco Smoke with Reduced Tobacco Specific Nitrosamines The present invention is directed, in one aspect, to a tobacco product having reduced tobacco specific nitrosamines (TSNA) in smoke obtained from combustion of leaves when smoked, i.e., tobacco smoke. The TSNA content in the mainsteam smoke of cigarettes following combustion is dependent of the following factors: (1) the amount of pre-existing TSNAs in the cut filler; (2) the efficiency of transfer of the pre-existing TSNAs from the cut filler to the smoke; (3) the extent of the destruction of pre-existing TSNAs via pyrolysis; and (4) the extent of formation of new TSNAs via pyrosynthesis. The tobacco smoke is produced from the modified tobacco plant, as described above, that have reduced free nitrate levels compared to a control tobacco plant, such as a wild-type tobacco plant control.

The cut filler tobacco or tobacco smoke produced from the modified tobacco plants described herein may have reduced TSNA levels compared to cut filler tobacco or tobacco smoke produced from a control tobacco plant, such as a wild-type tobacco plant control. In some embodiments, the cut filler tobacco or tobacco smoke produced from the modified tobacco plants may have reduced total TSNA levels compared to cut filler tobacco or tobacco smoke produced from a control tobacco plant, such as a wild-type tobacco plant control. In some embodiments, the cut filler tobacco or tobacco smoke produced from the modified tobacco plants may have reduced levels of at least one TSNA including, but not limited to, N-nitrosonornicotine (NNN), 4-(methylnitrosamino)-1-(3-pyridyl)-1-butanone (NNK), N-nitrosoanabasine (NAB), N-nitrosoanatabine (NAT), and combinations thereof, as compared to cut filler tobacco or tobacco smoke produced from tobacco of the same variety and cultivated by conventional techniques or a tobacco product prepared from conventional tobacco.

The cut filler tobacco produced from the modified tobacco plant may have at least about 5.0% reduction, at least about 10.0% reduction, at least about 15.0% reduction, at least about 20.0% reduction, at least about 25.0% reduction, at least about 30.0% reduction, at least about 32.0% reduction, at least about 35.0% reduction, at least about 40.0% reduction, at least about 44.0% reduction, at least about 45.0% reduction, at least about 50.0% reduction, at least about 52.0% reduction, at least about 55.0% reduction, at least about 60.0% reduction, at least about 64.0% reduction, at least about 65.0% reduction, at least about 70.0% reduction, at least about 72.0% reduction, at least about 72.5% reduction, at least about 73.0% reduction, at least about 75.0% reduction, at least about 80.0% reduction, at least about 85.0% reduction, at least about 90.0%, at least about 95.0% reduction, or at least about 99.0% reduction in total TSNA levels or in the levels of at least one TSNA including, but not limited to, N-nitrosonomicotine (NNN), 4-(methylnitrosamino)-1-(3-pyridyl)-1-butanone (NNK), N-nitrosoanabasine (NAB), N-nitrosoanatabine (NAT), and combinations thereof, compared to cut filler tobacco produced from a control cut filler tobacco which is produced from a control tobacco plant.

The cut filler tobacco produced from the tobacco product may have from about 5.0% to about 99.0%, about 5.0% to about 95.0%, about 5.0% to about 90.0%, about 5.0% to about 85.0%, about 5.0% to about 80.0%, about 5.0% to about 75.0%, about 5.0% to about 70.0%, about 5.0% to about 65.0%, about 5.0% to about 60.0%, about 5.0% to about 55.0%, about 5.0% to about 50.0%, about 5.0% to about 45.0%, about 5.0% to about 40.0%, about 10.0% to about 99.0%, about 10.0% to about 95.0%, about 10.0% to about 90.0%, about 10.0% to about 85.0%, about 10.0% to about 80.0%, about 10.0% to about 75.0%, about 10.0% to about 70.0%, about 10.0% to about 65.0%, about 10.0% to about 60.0%, about 10.0% to about 55.0%, about 10.0% to about 50.0%, about 10.0% to about 45.0%, about 10.0% to about 40.0%, about 20.0% to about 99.0%, about 20.0% to about 95.0%, about 20.0% to about 90.0%, about 20.0% to about 85.0%, about 20.0% to about 80.0%, about 20.0% to about 75.0%, about 20.0% to about 70.0%, about 20.0% to about 65.0%, about 20.0% to about 60.0%, about 20.0% to about 55.0%, about 20.0% to about 50.0%, about 20.0% to about 45.0%, about 20.0% to about 40.0%, about 30.0% to about 99.0%, about 30.0% to about 95.0%, about 30.0% to about 90.0%, about 30.0% to about 85.0%, about 30.0% to about 80.0%, about 30.0% to about 75.0%, about 30.0% to about 70.0%, about 30.0% to about 65.0%, about 30.0% to about 60.0%, about 30.0% to about 55.0%, about 30.0% to about 50.0%, about 30.0% to about 45.0%, about 30.0% to about 40.0% to about 99.0%, about 40.0% to about 95.0%, about 40.0% to about 90.0%, about 40.0% to about 85.0%, about 40.0% to about 80.0%, about 40.0% to about 75.0%, about 40.0% to about 70.0%, about 40.0% to about 65.0%, about 40.0% to about 60.0%, about 40.0% to about 55.0%, about 40.0% to about 50.0%, about 50.0% to about 99.0%, about 50.0% to about 95.0%, about 50.0% to about 90.0%, about 50.0% to about 85.0%, about 50.0% to about 80.0%, about 50.0% to about 75.0%, about 50.0% to about 70.0%, about 50.0% to about 65.0%, about 50.0% to about 60.0%, about 50.0% to about 55.0%, about 60.0% to about 99.0%, about 60.0% to about 95.0%, about 60.0% to about 90.0%, about 60.0% to about 85.0%, about 60.0% to about 80.0%, about 60.0% to about 75.0%, about 60.0% to about 70.0%, or about 60.0% to about 65.0% reduction in total TSNA levels or in the levels of at least one TSNA including, but not limited to, N-nitrosonornicotine (NNN), 4-(methylnitrosamino)-1-(3-pyridyl)-1-butanone (NNK), N-nitrosoanabasine (NAB), N-nitrosoanatabine (NAT), and combinations thereof compared to cut filler tobacco produced from a control cut filler tobacco which is produced from a control tobacco plant.

The tobacco smoke generated from the tobacco product may have at least about 5.0% reduction, at least about 10.0% reduction, at least about 15.0% reduction, at least about 20.0% reduction, at least about 25.0% reduction, at least about 30.0% reduction, at least about 32.0% reduction, at least about 35.0% reduction, at least about 40.0% reduction, at least about 44.0% reduction, at least about 45.0% reduction, at least about 50.0% reduction, at least about 52.0% reduction, at least about 55.0% reduction, at least about 60.0% reduction, at least about 64.0% reduction, at least about 65.0% reduction, at least about 70.0% reduction, at least about 72.0% reduction, at least about 72.5% reduction, at least about 73.0% reduction, at least about 75.0% reduction, at least about 80.0% reduction, at least about 85.0% reduction, at least about 90.0%, at least about 95.0% reduction, or at least about 99.0% reduction in total TSNA levels or in the levels of at least one TSNA including, but not limited to, N-nitrosonornicotine (NNN), 4-(methylnitrosamino)-1-(3-pyridyl)-1-butanone (NNK), N-nitrosoanabasine (NAB), N-nitrosoanatabine (NAT), and combinations thereof, compared to tobacco smoke from a control tobacco product which is produced from a control tobacco plant.

The tobacco smoke generated from the tobacco product may have from about 5.0% to about 99.0%, about 5.0% to about 95.0%, about 5.0% to about 90.0%, about 5.0% to about 85.0%, about 5.0% to about 80.0%, about 5.0% to about 75.0%, about 5.0% to about 70.0%, about 5.0% to about 65.0%, about 5.0% to about 60.0%, about 5.0% to about 55.0%, about 5.0% to about 50.0%, about 5.0% to about 45.0%, about 5.0% to about 40.0%, about 10.0% to about 99.0%, about 10.0% to about 95.0%, about 10.0% to about 90.0%, about 10.0% to about 85.0%, about 10.0% to about 80.0%, about 10.0% to about 75.0%, about 10.0% to about 70.0%, about 10.0% to about 65.0%, about 10.0% to about 60.0%, about 10.0% to about 55.0%, about 10.0% to about 50.0%, about 10.0% to about 45.0%, about 10.0% to about 40.0%, about 20.0% to about 99.0%, about 20.0% to about 95.0%, about 20.0% to about 90.0%, about 20.0% to about 85.0%, about 20.0% to about 80.0%, about 20.0% to about 75.0%, about 20.0% to about 70.0%, about 20.0% to about 65.0%, about 20.0% to about 60.0%, about 20.0% to about 55.0%, about 20.0% to about 50.0%, about 20.0% to about 45.0%, about 20.0% to about 40.0%, about 30.0% to about 99.0%, about 30.0% to about 95.0%, about 30.0% to about 90.0%, about 30.0% to about 85.0%, about 30.0% to about 80.0%, about 30.0% to about 75.0%, about 30.0% to about 70.0%, about 30.0% to about 65.0%, about 30.0% to about 60.0%, about 30.0% to about 55.0%, about 30.0% to about 50.0%, about 30.0% to about 45.0%, about 40.0% to about 99.0%, about 40.0% to about 95.0%, about 40.0% to about 90.0%, about 40.0% to about 85.0%, about 40.0% to about 80.0%, about 40.0% to about 75.0%, about 40.0% to about 70.0%, about 40.0% to about 65.0%, about 40.0% to about 60.0%, about 40.0% to about 55.0%, about 40.0% to about 50.0%, about 50.0% to about 99.0%, about 50.0% to about 95.0%, about 50.0% to about 90.0%, about 50.0% to about 85.0%, about 50.0% to about 80.0%, about 50.0% to about 75.0%, about 50.0% to about 70.0%, about 50.0% to about 65.0%, about 50.0% to about 60.0%, about 50.0% to about 55.0%, about 60.0% to about 99.0%, about 60.0% to about 95.0%, about 60.0% to about 90.0%, about 60.0% to about 85.0%, about 60.0% to about 80.0%, about 60.0% to about 75.0%, about 60.0% to about 70.0%, or about 60.0% to about 65.0% reduction in total TSNA levels or in the levels of at least one TSNA including, but not limited to, N-nitrosonornicotine (NNN), 4-(methylnitrosamino)-1-(3-pyridyl)-1-butanone (NNK), N-nitrosoanabasine (NAB), N-nitrosoanatabine (NAT), and combinations thereof, compared to tobacco smoke from a control tobacco product which is produced from a control tobacco plant.

8. Method of Producing Tobacco Product Having Reduced TSNA

The present invention is also directed to methods for producing a tobacco product having reduced TSNA levels. In some embodiments, the methods described herein can be used to introducing into a plant cell an isolated polynucleotide encoding a deregulated nitrate reductase polypeptide; regenerating the transformed cell to produce a transgenic plant; and producing a tobacco product from a leaf of the transgenic plant. In some embodiments, the methods described herein can be used to introducing into a plant cell a genome editing system that targets an endogenous nitrate reductase gene; regenerating the transformed cell to produce a transgenic plant; and producing a tobacco product from a leaf of the transgenic plant.

In some embodiments, a plant may be regenerated or grown from the plant, plant tissue or plant cell. Any suitable methods for regenerating or growing a plant from a plant cell or plant tissue may be used, such as, without limitation, tissue culture or regeneration from protoplasts. Suitably, plants may be regenerated by growing transformed plant cells on callus induction media, shoot induction media and/or root induction media. The regenerated plants have substantially all the morphological and physiological characteristics of the modified tobacco plant.

9. Method of Reducing Tobacco Specific Nitrosamines in Tobacco Product

The present invention is directed, in one aspect, to methods for producing a tobacco product having reduced TSNA levels compared to the TSNA levels in an unmodified tobacco plant. The method comprises modifying a tobacco plant to comprise a polynucleotide comprising, consisting or consisting essentially of a sequence encoding a deregulated nitrate reductase enzyme, a polypeptide encoded by the polynucleotide set forth in (i); a polypeptide comprising, consisting or consisting essentially of a sequence encoding a deregulated nitrate reductase enzyme; or a construct, vector or expression vector comprising the polynucleotide set forth in (i), and wherein the expression or activity of said nitrate reductase is deregulated as compared to a control unmodified tobacco plant; harvesting tobacco leaves from said modified tobacco plant; and producing a tobacco product from the harvested leaves.

10. Method of Reducing Tobacco Specific Nitrosamines in Smoke from Tobacco Product The present invention is directed, in one aspect, to methods for producing a tobacco product wherein TSNA levels measured in smoke obtained from combustion of leaves of a modified tobacco plant are reduced compared to TSNA levels measured in smoke obtained from combustion of an unmodified tobacco plant. The method comprises modifying a tobacco plant to comprise a polynucleotide comprising, consisting or consisting essentially of a sequence encoding a deregulated nitrate reductase enzyme, a polypeptide encoded by the polynucleotide set forth in (i); a polypeptide comprising, consisting or consisting essentially of a sequence encoding a deregulated nitrate reductase enzyme; or a construct, vector or expression vector comprising the polynucleotide set forth in (i), and wherein the expression or activity of said nitrate reductase is deregulated as compared to a control unmodified tobacco plant; harvesting tobacco leaves from said modified tobacco plant; and producing a tobacco product from the harvested leaves.

It will be readily apparent to those skilled in the art that other suitable modification and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples which are merely intended only to illustrate some aspects and embodiments of the disclosure, and should not be viewed as limiting to the scope of the disclosure. The disclosures of all journal references, U.S. patents and publications referred to herein are hereby incorporated by reference in their entireties.

The present invention has multiple aspects, illustrated by the following non-limiting examples.

EXAMPLES

Example 1

Methods and Materials

Plasmid Constructs.

The following five genes involved in the nitrate-assimilation (N-assimilation) pathway were cloned using polymerase chain reaction (PCR): "S523D-NR"—a tobacco Nia2 cDNA (Vaucheret et al. Plant Mol. Biol. 12:597-200 (1989)) containing a Ser to Asp substitution mutation introduced at codon 523 using site-directed mutagenesis (Lillo et al. Plant J. 35:566-573 (2003)); "tr-NR"—an N-terminal truncation of the Nia2 cDNA where codons 2-56 were removed by site-directed mutagenesis (Nussaume et al. Plant Cell 7:611-621 (1995)); "GS1"—the full-length cDNA of the tobacco Gln1-3 gene (Dubois et al. Plant Mol. Biol. 31:803-817 (1996)); "GOGAT"—the full-length cDNA of the GLT1 gene of *Arabidopsis thaliana* (Lancien et al. Plant J. 29:347-358 (2002)); and "ICDH"—a full length cDNA of a tobacco cytosolic isocitrate dehydrogenase (GenBank Accession No. 77944).

To express the various constructs in tobacco, each cDNA was inserted individually into the binary vector pBI121 (Chen et al. Mol. Breed. 11:287-293 (2003)) by replacing the GUS reporter gene within this vector with the respective N-assimilation pathway cDNA. This placed the constructs under the transcriptional control of the strong, constitutive 35S promoter of CaMV. Plant expression vector pBI121 contains the nptII gene that enables selection of transformed cells using the antibiotic kanamycin. For constructs containing the CYP82E4 (E4) promoter, the ~850 bp region of the vector containing the 35S promoter was excised and replaced with the 2.2 kb region immediately upstream of the CYP82E4 start codon (Chakrabarti et al. Plant Mol. Biol. 66:415-427 (2008)). The resulting plant expression vectors were introduced into *Agrobacterium tumefaciens* strain EHA105 and grown on YEP medium (1% Bacto-Peptone, 1% Bacto-Yeast Extract and 0.5% NaCl) supplemented with kanamycin (50 mg/L) and rifampicin (20 mg/L).

Plant Materials.

Burley breeding line DH98-325-6#775 was transformed individually with the 35S:tr-NR, 35S:S523D-NR, 35S:GS1, 35S:GOGAT, 35S:ICDH, E4:tr-NR, E4:S523D-NR and E4:GOGAT constructs. Several independent transgenic lines for each construct were assayed using semi-quantitative RT-PCR to identify the individual plants displaying the highest levels of transgene expression, relative to a tobacco actin gene. Green leaf tissue was used for the expression analysis of plants containing constructs under the transcriptional control of the 35S CaMV promoter. For plants containing the E4 promoter, expression analysis was conducted on leaves that were detached and treated with ethephon as described by Chakrabarti et al. (2008). For each high expressing T0 individual, several T1 plants were grown and genotyped using diagnostic primers for the cognate transgenes to distinguish progeny inheriting the transgene from null segregants. Numerous T1 progeny from each T0 plant that assayed positive for possessing a given transgene were again assayed by semi-quantitative RT-PCR to test whether the high expression phenotype was faithfully transmitted to the next generation. Lines that were shown to uniformly transmit the high expression phenotype were used to produce the T2 generation progeny.

Burley cultivar TN90e4e5 was co-transformed with the 35S:S523D-NR and E4:S523D-NR constructs. Equal amounts of two *Agrobacterium* cultures, each harboring one of the S523D-NR constructs, were combined and used to transform leaf discs of TN90e4e5. PCR-based molecular genotyping was conducted to distinguish the complement of transgenes within each T0 individual. Primers specific for the 35S or E4 promoter regions were paired with primers corresponding to S523D-NR to distinguish the two constructs. Vector control plants were generated by transforming TN90e4e5 with an E4:GUS construct (Chakrabarti et al., 2008). Transgene expression levels for each T0 plants were determined by RT-PCR using an Mx3000P QPCR instrument according to the protocol of the manufacturer (Agilent Technologies). RT-PCR data using primers corresponding to S523D-NR were normalized in accordance to the expression of an elongation factor 1α control gene.

Growth Conditions for Controlled Environmental Chamber Experiments.

T2 transgenic tobacco plants from lines 35S:tr-NR, 35S:S523D-NR, 35S:GS1, 35S:GOGAT, 35S:ICDH and WT controls were grown in controlled environmental chambers at the North Carolina State University Phytotron facility. Seeds were germinated on a 2:1 peat-sand mix. Four-week-old seedlings were transplanted to individual cells and grown using a 12 hr 26° C. day/12 hr 22° C. night regime. A photosynthetic photon flux density of 1500 µmol $m^{-2}s^{-1}$ was provided by a 1:1 ratio of metal halide and high-pressure sodium lamps and incandescent lamps. Plants were watered once daily with deionized water, and once daily with a nutrient solution consisting of 106.23 mg/L Nitrogen, 10.41 mg/L Phosphorus, 111.03 mg/L Potassium, 54.4 mg/L Calcium, 12.4 mg/L Magnesium, 5 mg/L Iron, 13.13 mg/L Sulfur, 0.113 mg/L Manganese, 0.24 mg/L Boron, 0.013 mg/L Zinc, 0.005 mg/L Copper, 0.00003 mg/L Cobalt, 0.05 mg/L Molybdenum and 11.04 mg/L sodium.

Approximately two months after planting, 18 plants per genotype were transplanted to 6" pots filled with steam-sterilized river sand. Care to taken to select individuals of similar size. Six plants per genotype were exposed to each of the nitrate-fertilization treatments. Plant death and/or the observance of abnormally stunted growth phenotypes resulted in the loss of four 35S:ICDH, two 35S:S523D-NR and one 35S:GS1 plant.

During the first seven days after transplant to 6" pots, all plants were watered with a nutrient solution containing excess nitrate (19 mM $NO_3$) to allow them to adjust to transplant shock. The 19 mM nitrate nutrient solution consisted of the following: 5 mM $Ca(NO_3)_2$, 2 mM $Mg(NO_3)_2$, 5 mM $KNO_3$, 1 mM $KH_2PO_4$, 0.5 mM $K_2SO_4$, 19 µM $H_3BO_3$, 3.7 µM $MnCl_2$, 0.3 µM $ZnSO_4$, 0.13 µM $CuSO_4$, 0.05 µM $Na_2MoO_4$, and 10.0 µM 330 Fe-Sequestrene. After the seven-day adjustment period, plants from each genotypic group were divided equally into three groups and watered with either a very low nitrate (0.2 mM $NO_3$), a medium nitrate (8 mM $NO_3$), or a high N (19 mM $NO_3^-$) nutrient solution over the course of the next 16 days. To maintain ionic and osmotic balance, $SO_4^2$ was substituted for $NO_3^-$ across the low and medium solutions as appropriate. Therefore, the low (0.2 mM $NO_3$) N nutrient consisted of 0.1 mM $Ca(NO_3)_2$, 3 mM $K_2SO_4$, 2 mM $MgSO_4$ and 4.9 mM $CaSO_4.2H_2O$ (with no $Mg(NO_3)_2$ or $KNO_3$) and the medium (8 mM $NO_3$) N nutrient contained 4 mM $Ca(NO_3)_2$, 3 mM $K_2SO_4$, 2 mM $MgSO_4$ and 1 mM $CaSO_4.2H_2O$ (with no $Mg(NO_3)_2$ or $KNO_3$).

During the course of the 16 day experiment, each plant was watered three times daily: in the morning with 200 mL of the appropriate nutrient solution, at noon with 200 mL DI water, and in the afternoon with 1000 mL DI water to leach out the nutrients, followed by 200 mL of the appropriate nutrient solution. The chamber conditions were 26° C./22° C. day/night, with a 12 hr/12 hr day/night period.

Chlorophyll Assays.

At the end of the treatment period, chlorophyll assays were conducted according to the protocol published in the Protocol Exchange (Ni et al. (2009) doi:10.1038/nprot.2009.12) using a DUO 640 Spectrophotometer (Beckman™ Coulter). The chlorophyll a (Ca), chlorophyll b (Cb) and chlorophyll a+b (Ca+b) concentrations were calculated according to the following formulas (Arnon Plant Physiol 24:1-15 (1949)), where V is volume of the extract (mL) and W is fresh leaf weight (g).

$$Ca\ (mg/g) = (12.7 \times A663 - 2.69 \times A645) \times V/(1000 \times W)$$

$$Cb\ (mg/g) = (22.9 \times A645 - 4.68 \times A663) \times V/(1000 \times W)$$

$$Ca+b\ (mg/g) = (8.02 \times A663 + 20.20 \times A645) \times V/(1000 \times W)$$

Fresh Weight Analysis and Sample Preparation.

After the 16 day treatment period, total plant biomass measurements were taken by cutting each plant at the base and recording their fresh weights Immediately after each sample was weighed, a single leaf from a similar position on each plant ($4^{th}$ or $5^{th}$ leaf from the top) was excised, its midrib removed, and the remaining lamina frozen in liquid nitrogen and stored at −80° C. for amino acid analysis. A small leaf sample (~300 mg) was also collected from a similar position from each plant for chlorophyll assays. The rest of the leaves on each plant were subsequently stripped from the main stem, placed in a paper bag, and incubated in a drying oven at 65° C. for two days. The dried leaf samples were subsequently ground to a fine powder for nitrate and ammonia analysis.

Nitrate, Nitrite and Ammonia Assays.

For the growth chamber experiments, approximately 100 mg of dried leaf powder from each sample was weighed, and extracted using 10 mL deionized water. After filtering through #4 Whatman™ filter paper, the supernatants were assayed for nitrate and ammonium concentrations using a multi-channel Auto-Analyzer in the Environmental and Agricultural Testing Service (EATS) lab in North Carolina State University. Nitrate and ammonium quantities were calculated according to the protocol in the Lachat Instruments Handbook.

For field grown samples and the greenhouse grown T0 materials, ground leaf tissue was analyzed for nitrate at the University of Kentucky Tobacco Analytical Laboratory. Nitrate quantification was determined according to the protocol outlined in Crutchfield and Grove (J. AOAC International 94:1898-1905 (2011)). Nitrite analysis was conducted on the ground air-cured field samples using the method described by Crutchfield and Burton (Anal. Letters 22:555-571 (1989)).

Amino Acid Assays.

Leaf samples from growth chamber grown plants that had been frozen in liquid nitrogen were dried to completeness by placing them in a freeze dryer for two days. The dried samples were then ground in liquid nitrogen to fine powder using a mortar and pestle. Approximately 100 mg dried leaves powder was weighed and provided to the analytical lab at the Biomanufacturing Training and Education Center at North Carolina State University for amino acid assay measurements. Briefly, each sample was extracted with 1.0 mL of 80% MeOH-20% $H_2O$ and vortexed, followed by centrifugation at 20,000×g. 200-µL aliquots of the clarified supernatant were chilled at −80° C. for approximately 2 hr then lyophilized overnight. The dried material was dissolved in 200 µL of borate buffer (pH 8.0) then diluted again 1:10 with borate buffer. Samples were derivatized by adding 10 µL of extracted sample to 70 µL borate buffer and 20 µL of derivatization reagent. Vials were heated at 55° C. for 10 minutes, cooled to room temperature and vortexed to mix the contents. The derivatized samples were analyzed using ultra high performance liquid chromatography.

Alkaloid and TSNA Analysis of Air-Cured Leaves.

The nicotine, nornicotine, anatabine and anabasine levels in cured leaf samples were quantitated using a Perkin-Elmer Autosystem XL Gas Chromatography according to previously established protocols (Jack et al. Rec. Adv. Tob. Sci. 33:58-79 (2007)). Total alkaloids were calculated as the sum of nicotine, nornicotine, anatabine and anabasine. Quantifications of NNN, NNK, NAT and NAB were conducted in accordance to "Method 1" of Morgan et al. (Beit. Tabakforschung 23:192-203 (2004)). Total TSNAs represented the sum of NNN, NNK, NAT and NAB.

TSNA Extraction and Analysis in Cut Filler Tobacco and Smoke.

Samples of cut filler tobacco were extracted with a 100 mM ammonium acetate solution containing deuterated internal standards to enable quantification. Extracts were filtered using a PVDF syringe filter (0.45 µm pore size) and analyzed by liquid chromatography tandem mass spectrometry (LC-MS/MS) coupled with electrospray ionization (ESI). D4-N-nitrosonornicotine (D4-NNN) was used as an internal standard for NNN, while D4-4-(methyl-nitrosamine)-1-(3-pyridyl)-1-butanone (D4-NNK) served as an internal standard for NNK, NAT and NAB.

Test cigarettes made from the cut filler were conditioned, and smoked according to the smoking procedure specified in Health Canada Method No. T-115. Mainstream smoke was collected onto Cambridge filters and extracted with 100 mM ammonium acetate containing D4-NNN and D4-NNK standards followed by filtration with a 0.45 µm pore PVDF syringe filter. Ammonium acetate extracts were analyzed by LC-MS/MS coupled with ESI and quantitated in accordance with the D4-NNN and D4-NNK standards.

Statistical Analysis.

The PROC GLM procedure of SAS 9.1 (SAS Institute, Cary, N.C.) was used to conduct an analysis of variance and to calculate means for each of the transgenic and WT lines included. Because of heterogeneous variances, natural logarithmic data transformations were conducted to approximate normal distributions for the fresh weight, nitrate and ammonia data collected for the growth chamber experiments. Nontransformed values were used for all other datasets. Significance levels were established in accordance with the Ryan-Einot-Gabriel-Welsch (REGWQ) multiple range test.

Example 2

Overexpression of N-Assimilation Genes in Burley Tobacco

Figure 3A:
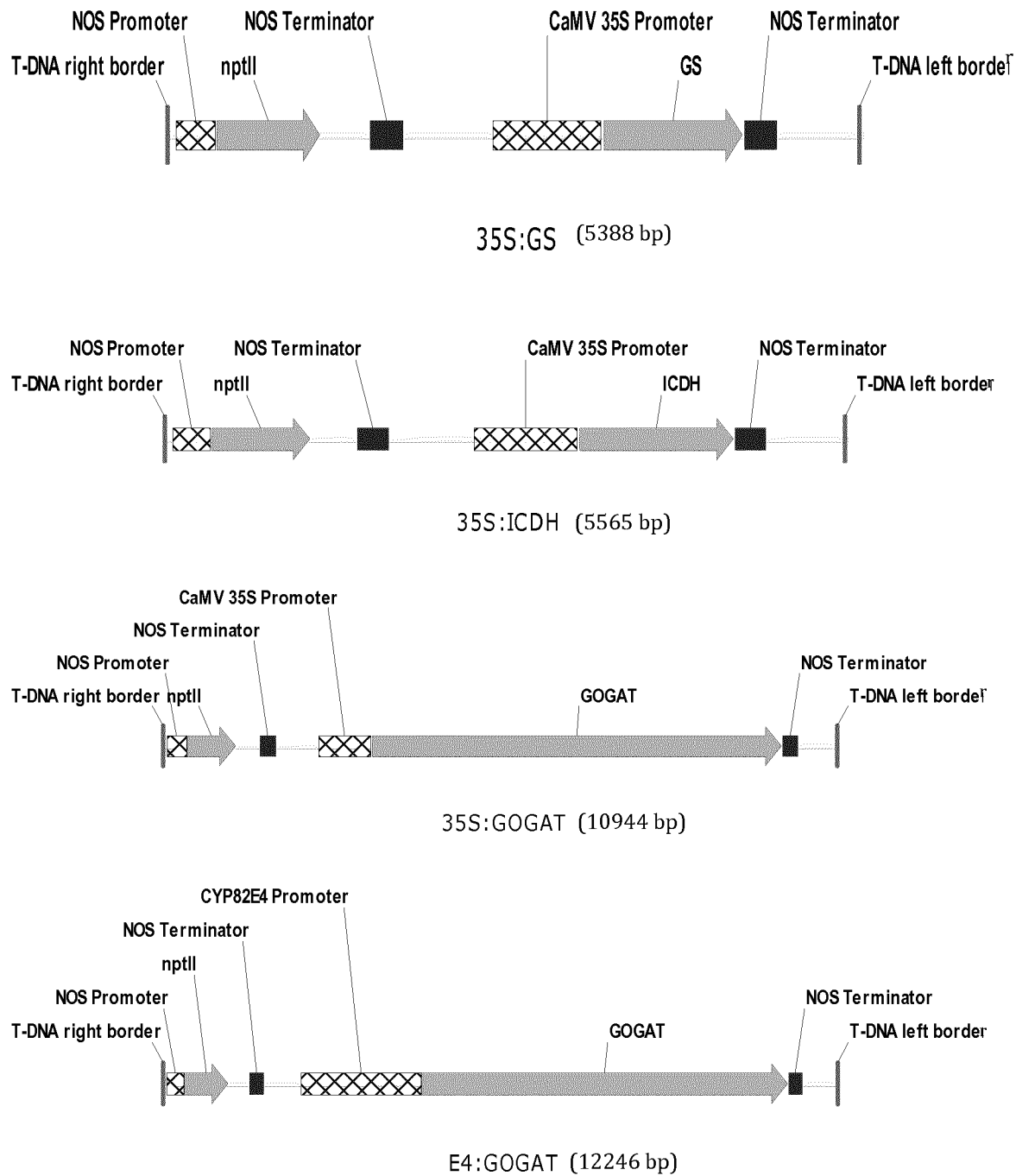

The GS1, NADH-GOGAT, ICDH or deregulated NR enzymes (either the 56 amino acid truncation mutation or the S523D point mutation) were overexpressed in burley tobacco plants to determine if ecotopic expression of any of these N-assimilation pathway genes 1) compensated for the chlorophyll deficiency and/or N-fertilization-associated growth defects characteristic of burley tobaccos; and/or 2) reduced the levels of free nitrate that accumulates in the leaf and help reverse the high nitrate accumulation phenotype that is characteristic of this class of tobacco plants. Replacement of the GUS reporter gene in the plant expression vector pBI121 with the N-assimilation pathway genes placed each of these constructs under the regulatory control of the strong constitutive 35S promoter of Cauliflower Mosaic Virus (CaMV), and the 3' nos terminator sequence of the nopaline synthase gene of *Agrobacterium tumefaciens* (Chen et al. Mol. Breed. 11:287-293 (2003)). A diagram of the constructs used is shown in FIGS. 3A-3B.

Burley tobacco line DH98-325-6#775 was transformed individually with each of the five constructs using standard *Agrobacterium*-mediated transformation protocols. DH98-325-6#775 represents a selection from an ethylmethane sulfonate (EMS) mutagenized burley population that contains a knockout mutation in CYP83E4, the major nicotine demethylase gene of tobacco (Lewis et al. Phytochem. 71:1988-1998 (2010)). Burley tobaccos are prone to a phenomenon called nicotine conversion in which the normally inactive CYP82E4 gene becomes spontaneously activated, giving rise to a high proportion of progeny that accumulates exceptionally high levels of the TSNA precursor nornicotine. The CYP82E4 knockout mutation in DH98-325-6#775 prevents nicotine conversion, and this line was selected to avoid potential complications that may have arisen in interpreting TSNA data among the various transgenic materials generated that would likely have become a factor if a standard burley cultivar had been used (due to the great variability in nornicotine levels that would have been expected to be observed using a normal burley background).

To enable the selection of plants that express the respective transgenes at a high level, at least 10 independent T0 plants for each construct were assayed by semi-quantitative RT-PCR. Seed was harvested from the three T0 lines of each construct that displayed the highest levels of transgene accumulation. Because of phenomena such as transgene silencing, or situations where a weakly expressing transgene and a highly expressing transgene may have become integrated at independent loci within the same T0 plant, it is possible that some T0 lines that show high transgene expression can produce progeny that segregate for both high and low transgene expression. Therefore, semi-quantitative RT-PCR was also conducted on numerous progeny of each selected high expressing T0 plants to test whether the T1 progeny that inherited the transgene(s) continued to express it at a high level. All plants used in subsequent studies were T2 plants taken from T1 seed lots where all progeny that tested positive for the transgene (via molecular genotyping) continued to express the transgene at a high level. T1 segregants that no longer possessed a transgene were used as the source for WT (null segregant) controls.

Example 3

Analysis of Transgenic Plants in a Controlled Growth Chamber Environment

To examine the effects of N-assimilation pathway gene overexpression in burley plants grown under varying conditions of nitrate availability, three sets of plants comprised of six young T2 plants for each transgene genotype (35S: tr-NR, 35S:S523D-NR, 35S:GS1, 35S:GOGAT and 35S: ICDH) and a the WT control were grown in a controlled environmental growth chamber. Each set of plants was watered with a nutrient solution containing 0.2 mM, 8 mM or 19 mM nitrate for 16 days. During the execution of the experiment, however, a small number of plants died or showed stunted growth and thus were not included in the analysis. At the end of the 16-day treatment period, dramatic differences were observed between sets of plants exposed to different levels of nitrate. As expected, tobacco plants watered with media containing 0.2 mM nitrate were chlorotic and displayed the least amount of growth, while plants provided with 19 mM nitrate were the largest and darkest green. No clear differences, however, were observed in the overall growth phenotype of plants containing any specific transgene in comparison to the WT controls at any given N-fertilization treatment.

Figure 4:
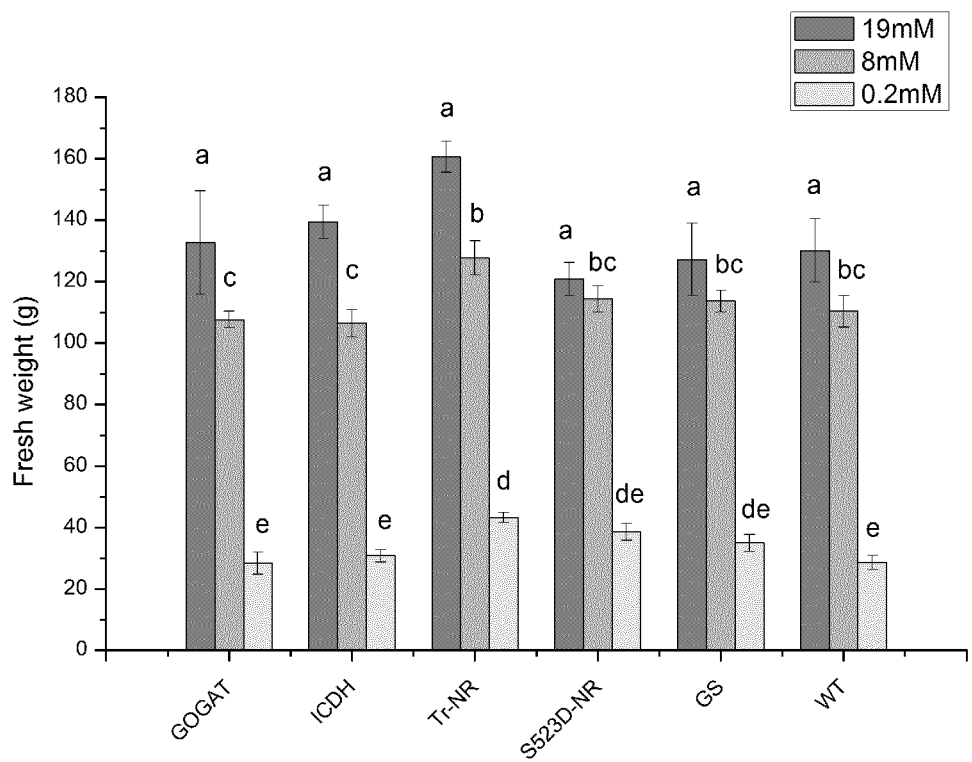
FIG. 4 shows the fresh weights of wild-type (WT) plants and 35S:tr-NR, 35S:S523D-NR, 35S:GS1, 35S:GOGAT, and 35S:ICDH transgenic lines grown under three levels of nitrate (N) fertilization.

Fresh weight measurements of the aerial portions of all plants were taken at the end of the treatment period, and are shown in Table 1 and FIG. 4. The values shown in FIG. 4 represent the nontransformed means±standard errors of 4-6 plants for each genotype. Statistical tests were performed on transformed data (natural logarithmic transformation). For each nitrate treatment level, means sharing the same letter were not significantly different from each other (P<0.5). For example, the letter "a" only applies to plants treated with 19 mM nitrate, letters "b" and "c" applies only to plants watered with the 8 mM nitrate media, and "d" and "e" only applies to plants treated with 0.2 mM nitrate. Table 1 shows the mean fresh weight, chlorophyll, nitrate and ammonia measurements of plants expressing N-assimilation pathway genes grown under three conditions of N-fertilization, where "Ca" is chlorophyll a and "Cb" is chlorophyll b. No significant differences were observed between the various transgenic genotypes versus the WT control for plants given the 8 mM and 19 mM nitrate treatments. At the very low nitrate treatment, however, the fresh weight of plants expressing the 35S:tr-NR construct was moderately greater than WT, a difference that was considered statistically significant.

TABLE 1

| Transgenic construct | N Treatment | Fresh weight (g) | Ca (mg/g) | Cb (mg/g) | Ca + b (mg/g) | Nitrate Conc (ppm) | Ammonia Conc (ppm) |
|---|---|---|---|---|---|---|---|
| 35S:GOGAT (n = 6) | 0.2 mM | 28.420 | 0.053 | 0.022 | 0.075 | 99.100 | 166.692 |
| 35S:GOGAT (n = 6) | 8 mM | 107.688 | 0.808 | 0.246 | 1.053 | 1923.283 | 475.642 |
| 35S:GOGAT (n = 6) | 19 mM | 132.798 | 0.763 | 0.232 | 0.995 | 15643.513 | 767.839 |
| 35S:ICDH (n = 5) | 0.2 mM | 30.796 | 0.069 | 0.027 | 0.096 | 67.085 | 118.261 |
| 35S:ICDH (n = 4) | 8 mM | 106.528 | 0.759 | 0.228 | 0.986 | 2257.586 | 269.833 |
| 35S:ICDH (n = 5) | 19 mM | 139.472 | 0.794 | 0.237 | 1.031 | 10118.411 | 621.612 |
| 35S:tr-NR (n = 6) | 0.2 mM | 43.270 | 0.050 | 0.021 | 0.071 | 59.426 | 119.206 |
| 35S:tr-NR (n = 6) | 8 mM | 127.707 | 0.725 | 0.218 | 0.942 | 846.754 | 273.316 |
| 35S:tr-NR (n = 6) | 19 mM | 160.602 | 0.838 | 0.255 | 1.093 | 8953.107 | 817.139 |
| 35S:S523D-NR (n = 5) | 0.2 mM | 38.548 | 0.048 | 0.018 | 0.066 | 59.917 | 117.472 |
| 35S:S523D-NR (n = 5) | 8 mM | 114.420 | 0.594 | 0.185 | 0.779 | 124.627 | 440.455 |
| 35S:S523D-NR (n = 6) | 19 mM | 120.892 | 0.739 | 0.215 | 0.954 | 2026.337 | 1544.655 |
| 35S:GS1 (n = 6) | 0.2 mM | 34.953 | 0.037 | 0.015 | 0.052 | 79.219 | 134.696 |
| 35S:GS1 (n = 6) | 8 mM | 113.643 | 0.647 | 0.197 | 0.844 | 2391.705 | 386.519 |
| 35S:GS1 (n = 5) | 19 mM | 127.266 | 0.985 | 0.306 | 1.290 | 12614.557 | 890.905 |
| Wild type (n = 6) | 0.2 mM | 28.673 | 0.024 | 0.011 | 0.035 | 75.771 | 128.621 |
| Wild type (n = 6) | 8 mM | 110.357 | 0.678 | 0.201 | 0.879 | 2295.164 | 328.894 |
| Wild type (n = 6) | 19 mM | 130.175 | 1.000 | 0.300 | 1.300 | 14918.953 | 798.592 |

Figure 5A:
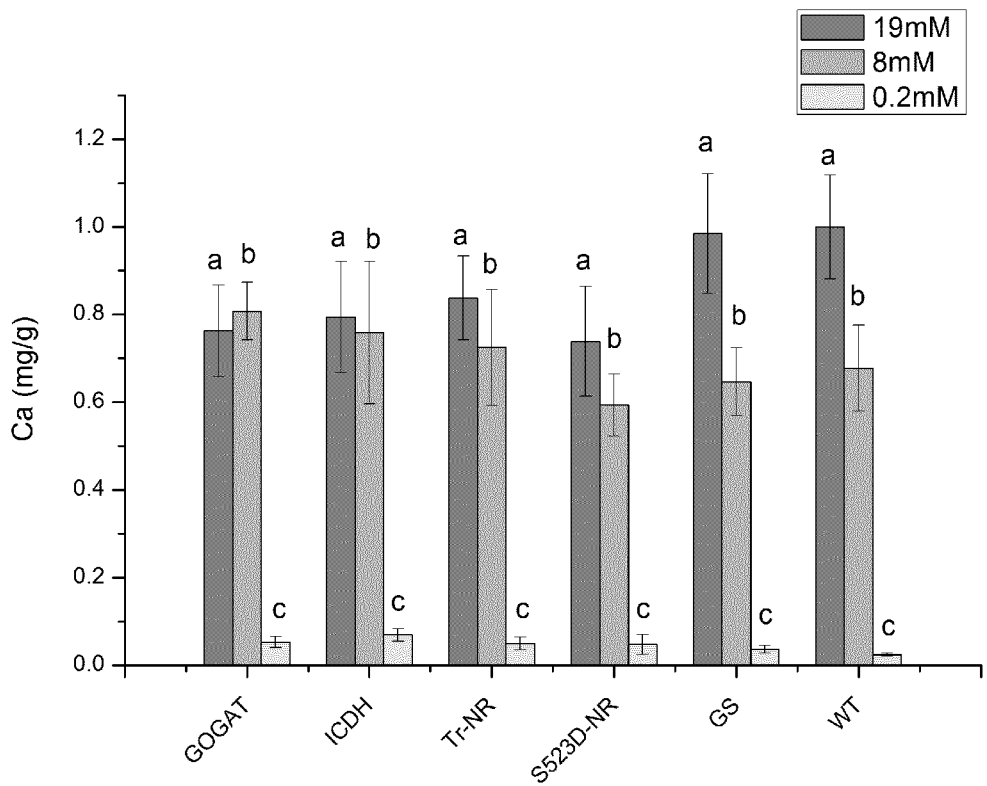
FIGS. 5A-5C show the chlorophyll a (Ca, FIG. 5A), chlorophyll b (Cb, FIG. 5B), and chlorophyll a+b (Ca+b, FIG. 5C) contents of WT plants and 35S:tr-NR, 35S:S523D-NR, 35S:GS1, 35S:GOGAT, and 35S:ICDH transgenic lines grown under three levels of N-fertilization.
Figure 5B:
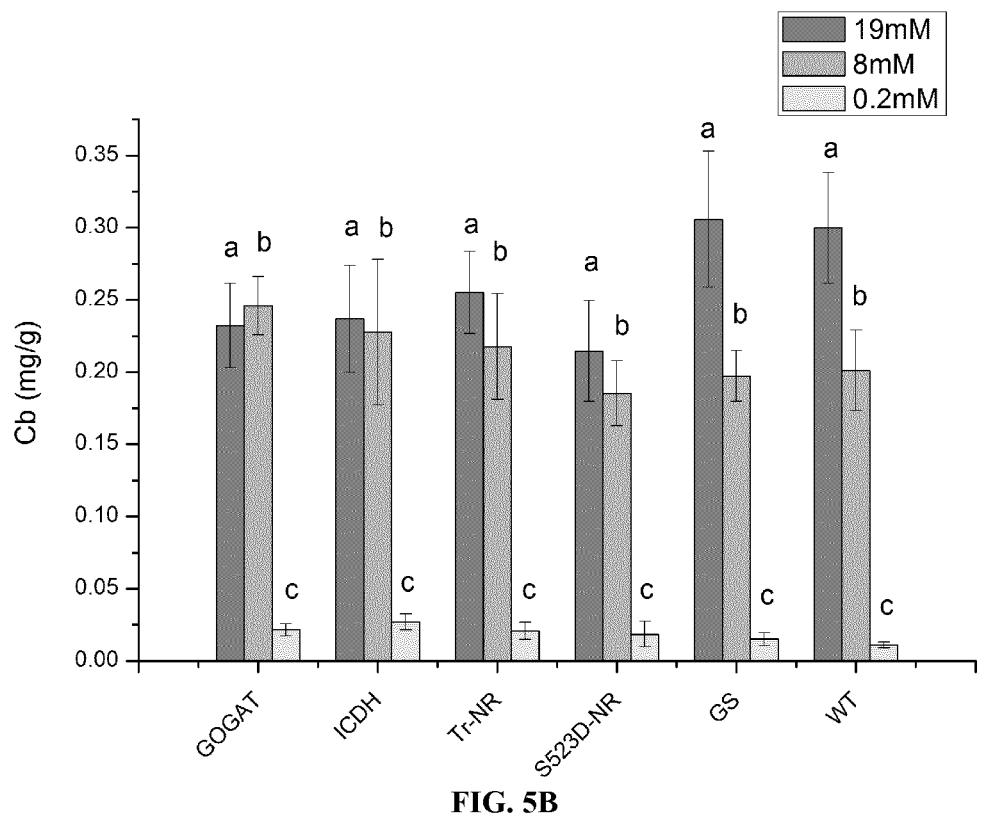
Figure 5C:
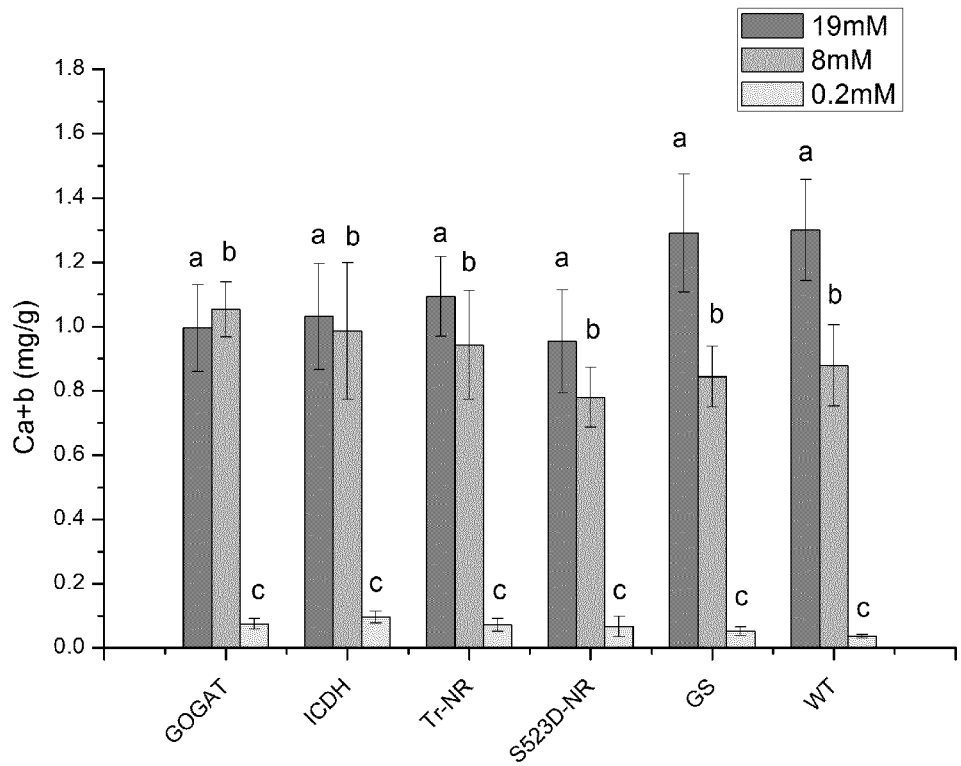

Burley tobacco plants show chlorophyll deficiencies, and are clearly distinguished from other tobacco types by their lighter green appearance. If any of the transgenes overexpressed were capable of compensating for the yb1 and/or yb2 mutations that characterize burley types, one might expect to see an increase in the chlorophyll content of these plants. Although no obvious differences were observed by mere visual observation between WT controls and the various transgenic genotypes tested, direct measurements of chlorophyll a, b and a+b contents were taken in the event that more subtle differences were present (Table 1). Similar to the fresh weight measurements, there was a very strong treatment effect with chlorophyll content being positively correlated with increasing nitrate fertilization. No significant differences in chlorophyll concentrations, however, were observed between any transgene genotype and the WT controls within any of the three nitrate treatments (FIGS. 5A-5C). The values shown in FIGS. 5A-5C represent the mean±standard error of 4-6 plants for each genotype. For each nitrate treatment level, means sharing the same letter are not significantly different from each other (P<0.5).

Figure 6A:
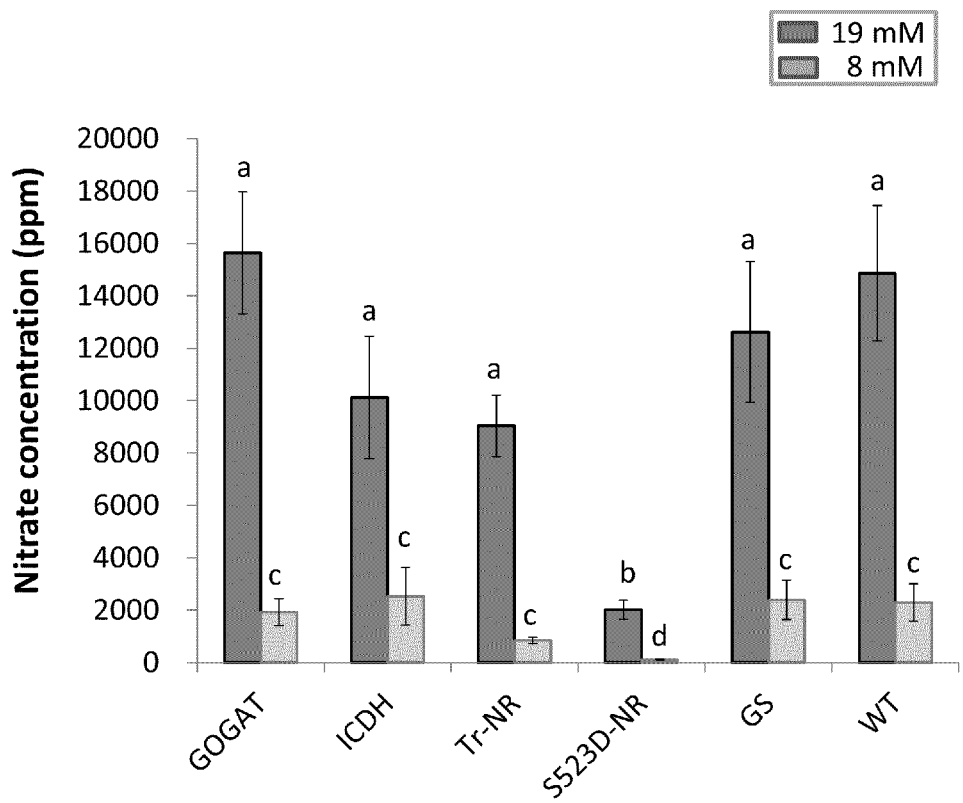
FIGS. 6A and 6B show the total nitrate content in leaves of WT plants and 35S:tr-NR, 35S:S523D-NR, 35S:GS1, 35S:GOGAT, and 35S:ICDH transgenic lines grown under three levels of N-fertilization.
Figure 6B:
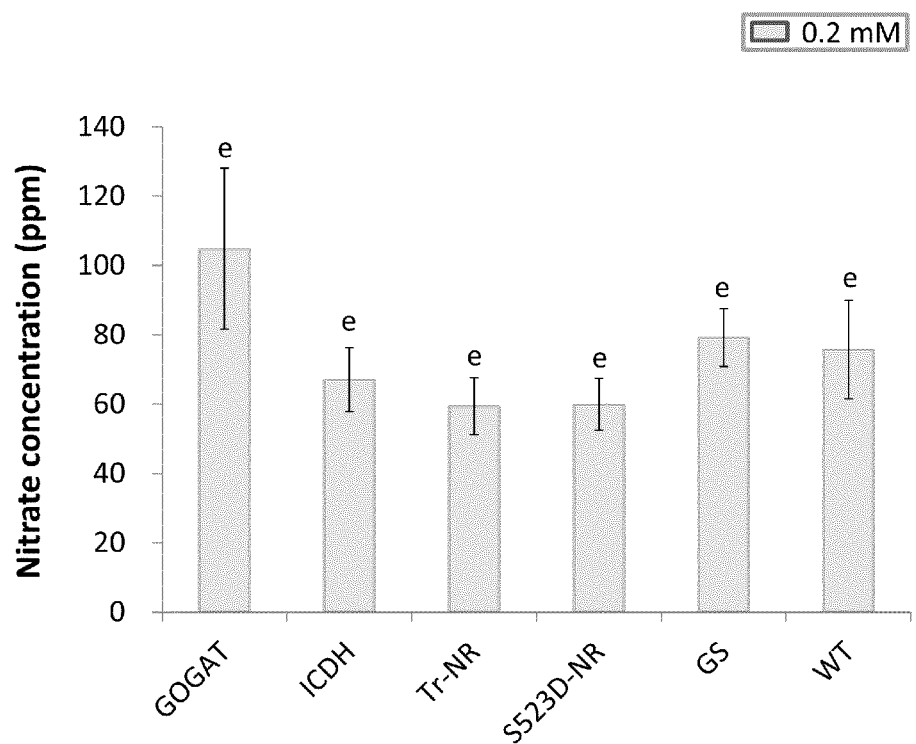

The average nitrate and ammonia concentrations for the various genotypes at each nitrate fertilization level are also shown in Table 1. At the 0.2 mM nitrate treatment level, all plants displayed exceptionally low nitrate accumulation, and no significant differences were observed between any transgene genotype and the WT controls (FIG. 6). FIG. 6A shows data from plants grown using the 19 mM $NO_3^-$ and 8 mM $NO_3^-$ treatments; results from the 0.2 mM $NO_3^-$ treatment are shown in FIG. 6B. The values shown represent the nontransformed means±standard errors of 4-6 plants for each genotype. Statistical tests were performed on transformed data (natural logarithmic transformation). For each nitrate treatment level, means sharing the same letter are not significantly different (P<0.5).

Under the 8 mM and 19 mM nitrate treatments, the average concentration of nitrate measured in the 35S:tr-NR plants were only 37% and 60% of that observed in the WT controls, respectively. There was a dramatic decrease in nitrate measured in the leaves of plants expressing the 35S:S523D-NR construct when fertilized with 8 mM or 19 mM nitrate. On average, plants containing this deregulated NR construct accumulated only about 5% of the amount of nitrate present in the control plants when watered under the 8 mM nitrate fertilization regime. Using the 19 mM N-fertilization treatment, WT plants averaged approximately 14,900 ppm nitrate, compared with only ~2000 ppm observed in the 35S:S523D-NR plants, a near 8-fold reduction in the transgenic individuals (FIG. 6A).

Figure 7:
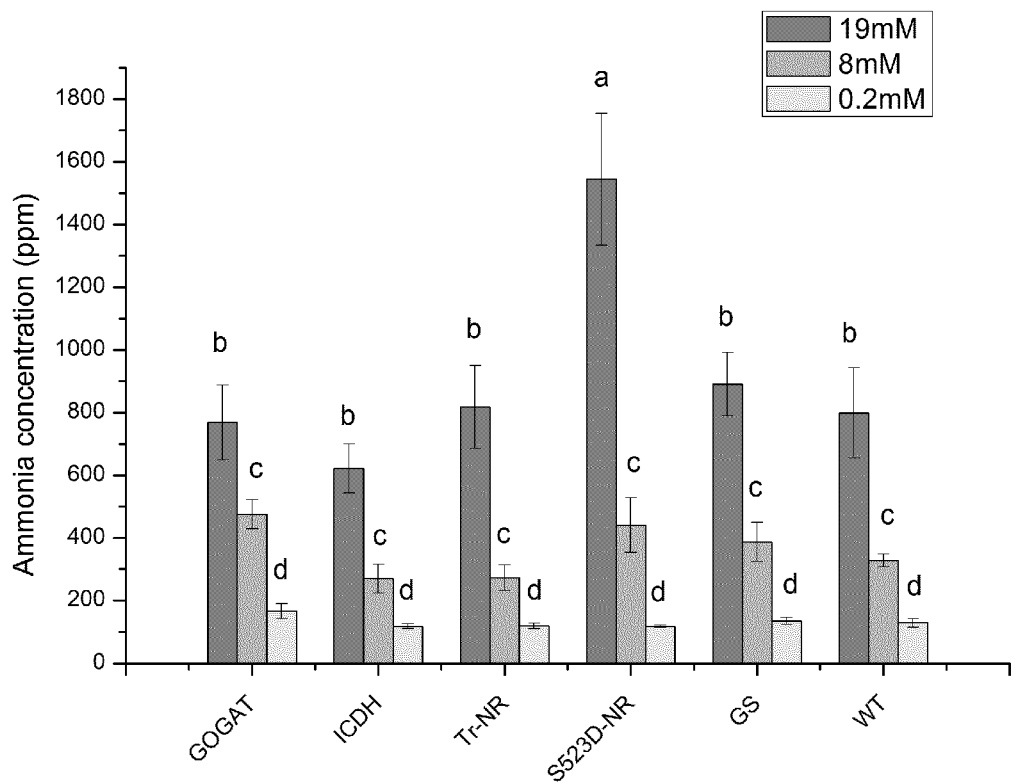
FIG. 7 shows the average ammonia content in leaves of WT plants and 35S:tr-NR, 35S:S523D-NR, 35S:GS1, 35S:GOGAT, and 35S:ICDH transgenic lines grown under three levels of N-fertilization.

The ammonia concentrations of the plants assayed in this experiment are shown in FIG. 7. The values shown in FIG. 7 represent the nontransformed means±standard errors of 4-6 plants for each genotype. Statistical tests were performed on transformed data (natural logarithmic transformation). For each nitrate treatment level, means sharing the same letter are not significantly different from each other (P<0.5). Although ammonia levels did not vary as greatly as nitrate, the 35S:S523D-NR plants accumulated approximately twice as much of this N-assimilation pathway metabolite as the control plants at the 19 mM nitrate treatment level. At the low and medium N treatment levels, however, no given transgenic genotype was statistically different in its average ammonia content from the WT controls, or any other transgenic genotype.

Since the N-assimilation pathway feeds directly into amino acid biosynthesis, the degree by which the concentrations of free amino acids may have been altered in the transgenic plants were established. Regardless of the transgene genotype, only minimal differences in nitrate and ammonium levels were observed in plants fertilized with the 0.2 mM nitrate media (FIGS. 6 and 7); therefore, the quantification of free amino acid content was only conducted on the plants treated with 8 mM and 19 mM nitrate. Table 2 shows the average concentrations (μmol/g dry weight) for all 20 amino acids across each transgenic and control genotype grown under the medium (8 mM) and high (19 mM) nitrate conditions.

TABLE 2

| Metabolite concentration (μmol/g dry weight) | | | | | | |
|---|---|---|---|---|---|---|
| Construct | | | | | | |
| | WT | | tr-NR | | S523D-NR | |
| | Nitrate Concentration | | | | | |
| | 8 mM | 19 mM | 8 mM | 19 mM | 8 mM | 19 mM |
| His | 0.916 | 1.670 | 0.934 | 1.830 | 1.450 | 7.584 |
| Asn | 4.057 | 17.934 | 7.079 | 33.443 | 13.880 | 98.851 |
| Ser | 22.750 | 33.695 | 18.203 | 27.970 | 17.308 | 46.370 |
| Gln | 36.651 | 111.772 | 30.583 | 151.395 | 72.416 | 968.148 |
| Arg | 0.490 | 2.898 | 5.767 | 3.869 | 0.791 | 15.292 |
| Gly | 4.461 | 27.494 | 2.832 | 11.812 | 1.856 | 48.442 |
| Asp | 18.533 | 26.219 | 10.239 | 17.290 | 15.605 | 44.033 |
| Glu | 82.841 | 86.255 | 70.556 | 81.072 | 78.470 | 144.897 |
| Thr | 36.234 | 28.762 | 24.079 | 30.702 | 22.548 | 41.732 |
| Ala | 11.124 | 28.160 | 16.904 | 23.089 | 10.784 | 40.634 |
| Pro | 15.916 | 20.291 | 20.839 | 31.498 | 22.776 | 58.392 |
| Cys | 0.041 | 0.154 | 0.135 | 0.096 | 0.077 | 0.090 |
| Lys | 1.522 | 1.696 | 1.613 | 1.925 | 1.686 | 3.295 |
| Tyr | 3.774 | 5.830 | 3.697 | 6.429 | 3.486 | 6.773 |
| Met | 0.224 | 0.720 | 0.537 | 0.492 | 0.601 | 1.447 |
| Val | 12.749 | 16.961 | 12.747 | 19.509 | 13.227 | 31.370 |
| Ile | 1.549 | 2.367 | 1.450 | 2.192 | 1.395 | 4.594 |
| Leu | 4.088 | 3.705 | 2.966 | 4.562 | 3.053 | 7.697 |
| Phe | 4.700 | 6.572 | 4.047 | 5.461 | 3.070 | 8.943 |
| Trp | 1.377 | 1.422 | 1.628 | 1.787 | 1.429 | 3.121 |
| Total | 263.998 | 424.578 | 236.835 | 456.424 | 285.909 | 1581.703 |
| Construct | | | | | | |
| | GS | | ICDH | | GOGAT | |
| | Nitrate Concentration | | | | | |
| | 8 mM | 19 mM | 8 mM | 19 mM | 8 mM | 19 mM |
| His | 1.024 | 1.091 | 1.060 | 1.605 | 1.013 | 1.713 |
| Asn | 3.599 | 10.052 | 2.715 | 14.428 | 7.400 | 11.330 |
| Ser | 17.576 | 28.809 | 5.631 | 32.661 | 22.804 | 30.923 |
| Gln | 20.609 | 77.103 | 5.325 | 93.425 | 17.624 | 73.545 |
| Arg | 0.215 | 1.758 | 3.134 | 4.797 | 0.598 | 2.266 |
| Gly | 1.731 | 23.584 | 0.441 | 32.613 | 1.761 | 19.006 |
| Asp | 12.647 | 25.376 | 6.358 | 18.297 | 15.992 | 27.733 |
| Glu | 67.637 | 84.602 | 37.214 | 71.596 | 77.295 | 78.855 |
| Thr | 55.242 | 36.986 | 13.128 | 28.333 | 51.094 | 40.043 |
| Ala | 10.023 | 21.379 | 6.448 | 25.789 | 22.996 | 22.634 |
| Pro | 13.612 | 18.443 | 8.120 | 29.038 | 16.345 | 26.077 |
| Cys | 0.145 | 0.110 | 0.148 | 0.302 | 0.115 | 0.055 |
| Lys | 1.650 | 1.850 | 1.819 | 2.157 | 1.944 | 2.033 |
| Tyr | 2.705 | 4.905 | 2.069 | 4.616 | 3.643 | 4.683 |
| Met | 0.635 | 0.730 | 0.332 | 0.649 | 0.515 | 0.567 |

TABLE 2-continued

| Metabolite concentration (μmol/g dry weight) | | | | | | |
|---|---|---|---|---|---|---|
| Val | 9.064 | 18.887 | 6.092 | 13.562 | 13.749 | 16.397 |
| Ile | 1.701 | 2.148 | 1.038 | 2.601 | 2.179 | 3.928 |
| Leu | 4.558 | 4.642 | 2.006 | 3.645 | 4.008 | 3.902 |
| Phe | 3.718 | 5.718 | 1.964 | 6.798 | 4.606 | 6.093 |
| Trp | 1.411 | 1.515 | 0.620 | 1.677 | 1.610 | 2.687 |
| Total | 229.501 | 369.688 | 105.663 | 388.590 | 267.292 | 374.471 |

Figure 8:
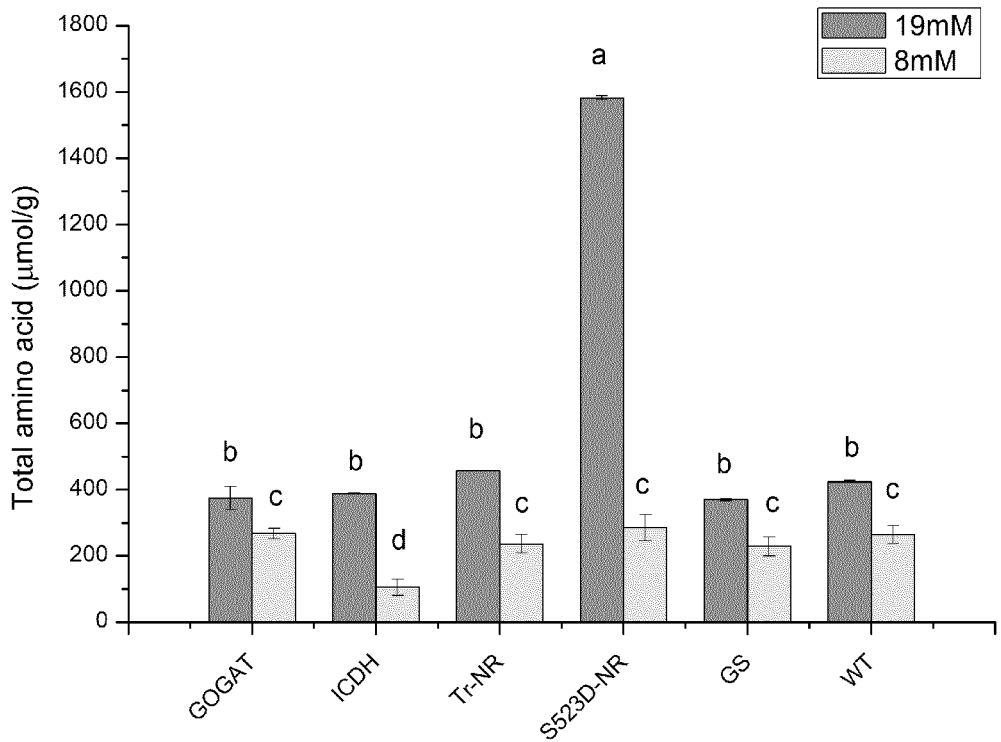
FIG. 8 shows the total free amino acid content in leaves of 35S:GOGAT, 35S:ICDH, 35S:tr-NR, 35S:S523D-NR, 35S:GS1, and WT plants grown under medium (8 mM) and high (19 mM)N-fertilization.

There was a great increase in total free amino acids in plants harboring the 35S:S523D-NR construct treated with 19 mM nitrate (FIG. 8). The values shown in FIG. 8 represent the mean±standard error of 4-6 plants for each genotype. For each nitrate treatment level, means sharing the same letter are not significantly different from each other (P<0.5). Tobacco plants expressing this construct accumulated on average 3.7 times more total free amino acids than WT plants. Although virtually every amino acid was higher in the 35S:S523D-NR group versus WT at the high N treatment, levels of Gln, Asn and Arg were particularly elevated, showing increases of 8.5-, 5.5- and 5.3-fold respectively (FIG. 9). The values shown in FIG. 9 represent the mean±standard error of 4-6 plants for each genotype. For each nitrate treatment level, means sharing the same letter are not significantly different from each other (P<0.5). When grown using the 8 mM nitrate nutrient solution, the levels of Gln and Asn were also significantly higher in the 35S:S523D-NR plant than the control (2- and 3.4-fold, respectively), yet the total amino acid concentrations between the two lines were nearly identical (FIG. 8), due to mean decreases in the levels of several other amino acids in the 35S:S523D-NR plants compared to WT (Table 2). As a whole, the amino acid profile of plants expressing the other deregulated NR gene construct (35S:tr-NR) was similar to WT plants.

Figure 9A:
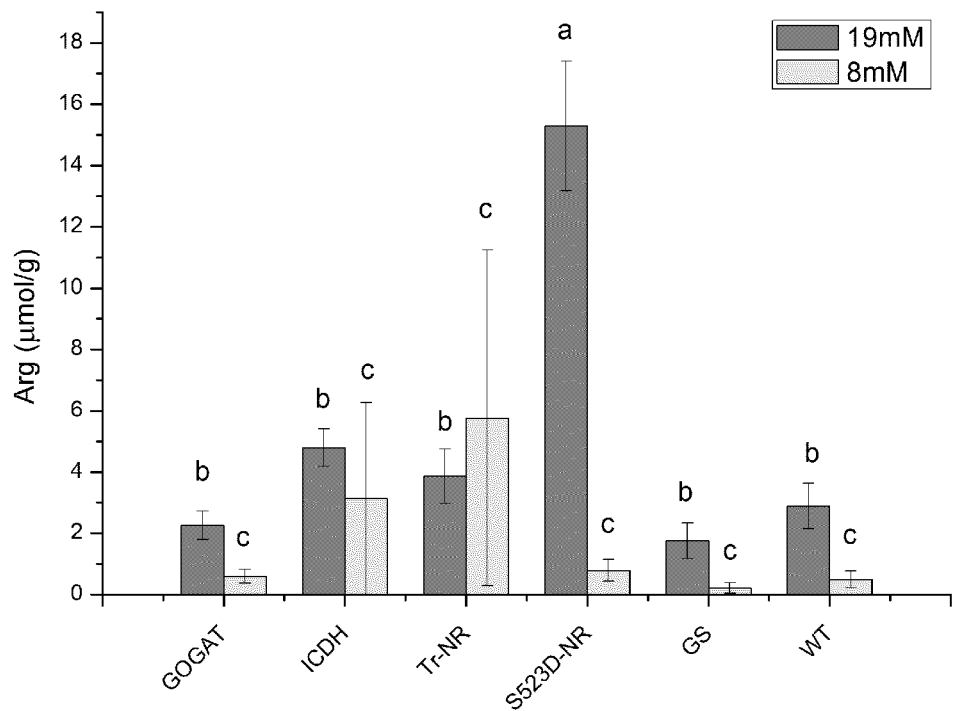
FIGS. 9A-9D show the arginine (Arg) (FIG. 9A), glutamine (Gln) (FIG. 9B), asparagine (Asn) (FIG. 9C), and glutamate (Glu) (FIG. 9D), and content in tobacco leaves of WT plants and 35S:tr-NR, 35S:S523D-NR, 35S:GS1, 35S:GOGAT, and 35S:ICDH transgenic lines grown under medium (8 mM) and high (19 mM)N-fertilization.
Figure 9B:
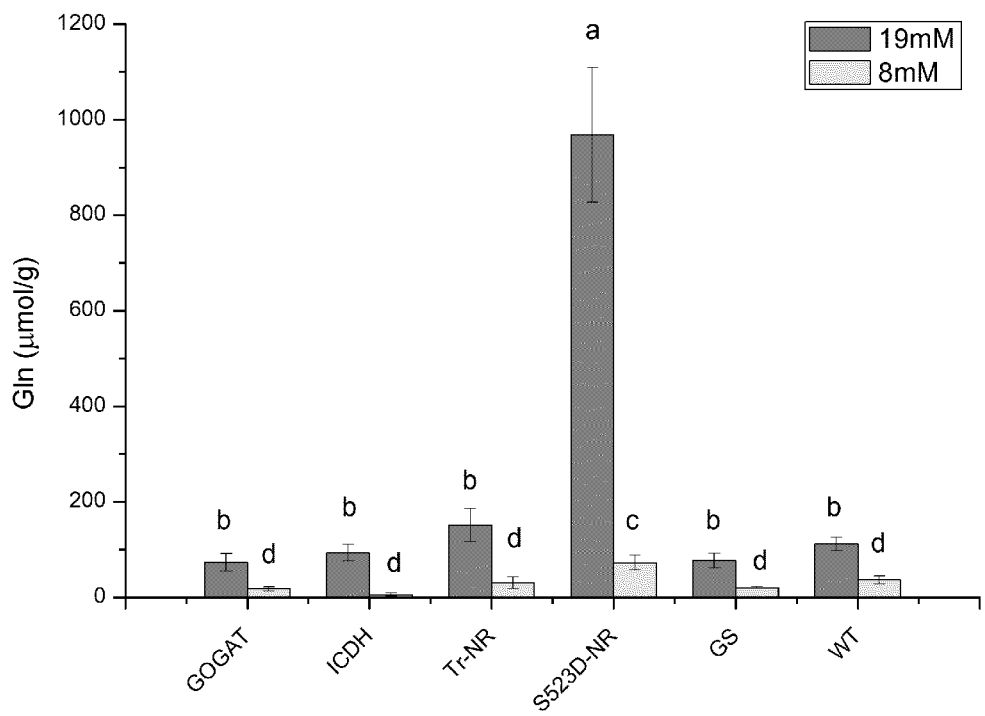
Figure 9C:
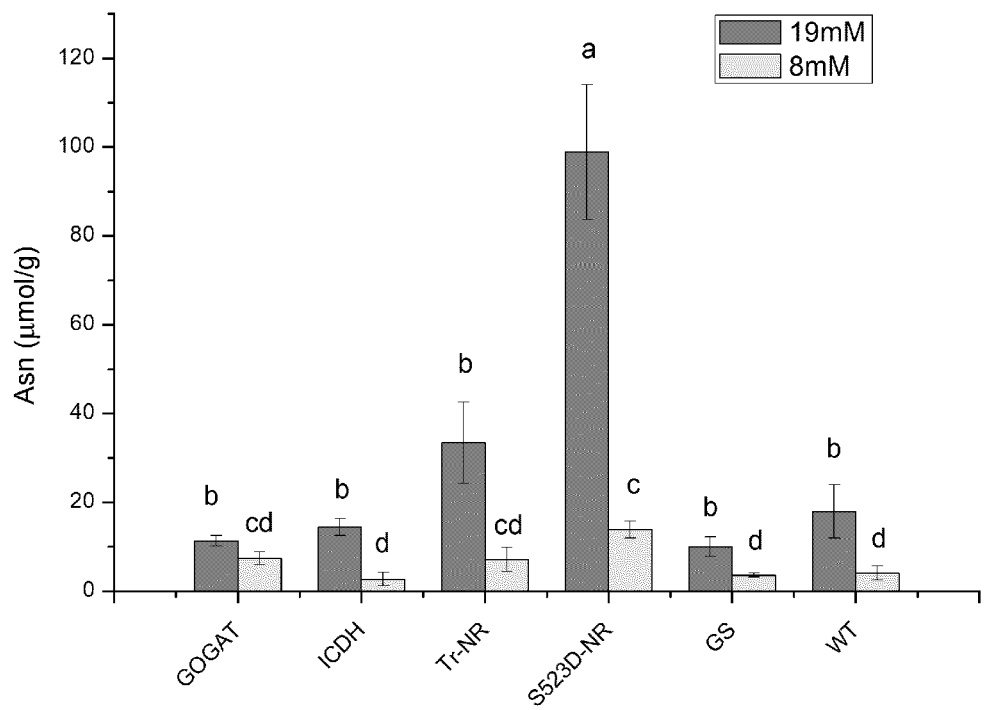
Figure 9D:
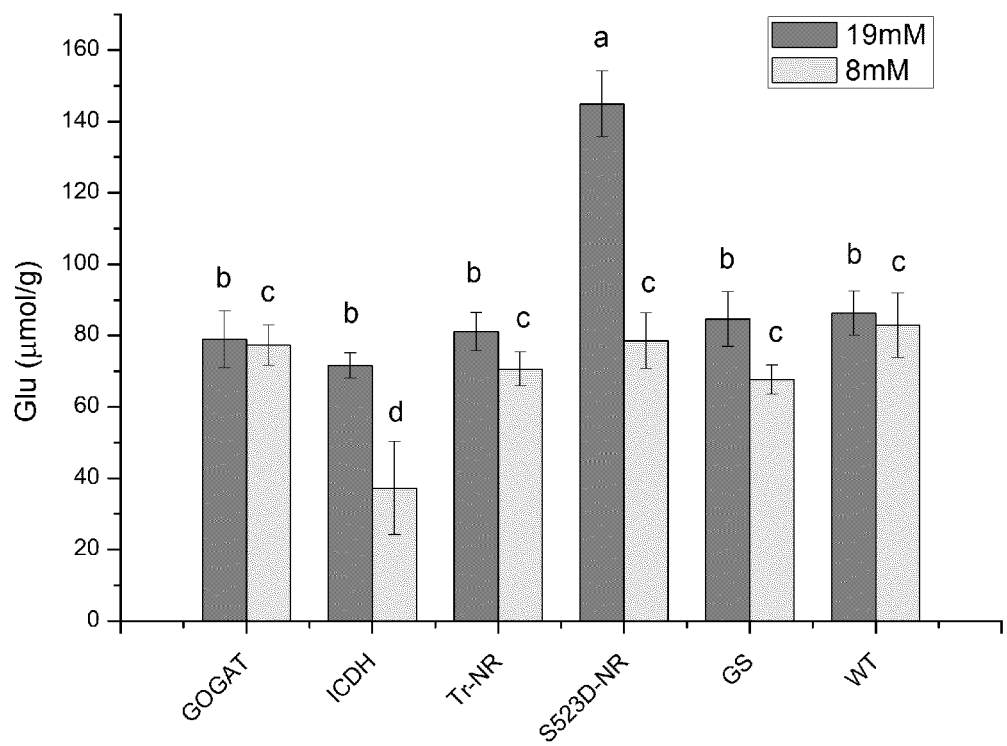

Glutamine is the reaction product of the GS enzyme. Thus, it is interesting that the levels of Gln were not increased in plants overexpressing the GS gene (FIG. 9B). This is in contrast to a 2-fold increase in Gln observed when an alfalfa GS cDNA was overexpressed in tobacco plants and fertilized with a high nitrate solution. Likewise, the levels of Glu were not significantly increased in the transgenic plants overexpressing the gene encoding the GOGAT enzyme that is directly responsible for its synthesis (FIG. 9). At the 8 mM nitrate fertilization level, plants overexpressing ICDH displayed lower amino acids in total (FIG. 8), and lower amounts of Glu specifically (FIG. 9D) than each of the other genotypes.

Chlorophyll deficiency represents one of the hallmarks of burley tobaccos, and is a trait that has been specifically attributed to the yb1 and yb2 loci. Whether grown in a growth chamber, greenhouse or field environment, all plants showed the same light green phenotype that is distinctive of this tobacco type. In the growth chamber experiments, the chlorophyll content of the WT and transgenic lines was directly measured and no differences were observed among any of these materials. These results suggest that the overexpression of the N-assimilation pathway associated genes (tr-NR, S523D-NR, GS1, GOGAT and ICDH) is not complementing, or otherwise functionally bypassing, the yb1 and/or yb2 mutant loci that define the burley phenotype.

Although no evidence was found that overexpression of any of the N-assimilation pathway transgenes tested could overcome the N-fertilization-associated growth defects or chlorophyll deficiencies that are characteristic of burley tobaccos, overexpression of deregulated NR activities were clearly effective in lowering the levels of free nitrate.

Example 4

Analysis of Transgenic Plants Grown Under Field Conditions

Constitutive expression of the deregulated S523D-NR construct mediated dramatic reductions in free nitrate accumulation in the leaf when grown under conditions of moderate or high N-fertilization. It also appeared that the deregulated tr-NR construct may confer a modest reduction in nitrate content. To determine the effects of the 35S:S523D-NR and 35S:tr-NR constructs on leaf nitrate concentration when grown in a field environment, T2 plants from the same seed lots used in the growth chamber experiments were germinated on float trays and transplanted to the field. Because the consequences of excess free nitrate within the leaf with respect to TSNA formation is primarily manifest during leaf senescence and curing, the deregulated NR constructs were placed under the transcriptional control of a strong senescence-specific promoter. The promoter controlling the CYP82E4 nicotine demethylase gene mediates a high level of gene expression specifically during senescence and air-curing. Constructs placing the S532D-NR and tr-NR cDNAs under the control of the CYP82E4 (E4) promoter were generated by initially replacing the CaMV 35S promoter from plant expression vector pBI121 with the 2.2 kb region immediately upstream of the CYP82E4 initiation of translation Met start codon, followed by the insertion of the NR cDNA downstream of the E4 promoter. As a control representing the overexpression of an N-assimilation pathway gene that does not influence leaf nitrate content, 35S:GOGAT and E4:GOGAT transgenic plants were also included in the field experiments. Diagrams of these vectors are shown in FIGS. 3A-3B. The specific T2 populations tested in the field possessing the E4 promoter-driven constructs came from seed lots of T1 plants that were shown to express the transgenes at a high level when treated with the senescence-inducing compound ethephon (Chakrabarti et al., 2008). Similar to the growth chamber studies, null segregants from T1 plants that no longer possessed a transgene were used as the source for WT controls for the field experiments.

Approximately 100 young plants for each of the seven genotypes tested (WT, 35S:S523D-NR, E4:S523D-NR, 35S:tr-NR, E4:tr-NR, 35S:GOGAT and E4:GOGAT) were divided equally and transplanted at two field locations in North Carolina using a randomized complete block design. Plants were grown at either a field research station near the town of Clayton, N.C., or the town of Rocky Mount, N.C. Because a substantial number of plants died after transplanting, the total number of plants that grew to maturity ranged from 60 to 79 per genotype. The tobacco plants were grown, topped and harvested according to standard industry practice for burley tobaccos. At maturity, the plants were stalk harvested and two leaves from a stalk position about one-third from the top were stripped from each plant, the mid-rib removed and the remaining lamina tissue placed in a paper bag. The plants were then hung on sticks and transferred to a rain-protected structure for air-curing. The leaf materials in the paper bags were placed in a drying oven and dried to completeness at 65° C. Dried leaf samples were ground and analyzed for nitrate content.

Average nitrate concentration in T2 plants expressing different genes involved in nitrate assimilation are shown in Table 3. As shown in Table 3, the average nitrate levels observed across the different genotypes assayed were very similar between the two field locations (one near Clayton, N.C., the other near Rocky Mount, N.C.). The most dramatic observation in this dataset was the great reduction in nitrate in the leaves of the 35S:S523D-NR plants. On average, tobacco plants containing the 35S:S523D-NR construct displayed only 4.2% and 5.6% of the amount of nitrate observed in the WT controls at the Clayton and Rocky Mount locations, respectively.

TABLE 3

|  | Mean ppm $NO_3^-$ | Standard Error of Mean |
|---|---|---|
| Clayton |  |  |
| WT (n = 40) | 1510 | 116 |
| 35S:S523D-NR (n = 31) | 63 | 7 |
| E4:S523D-NR (n = 32) | 1107 | 102 |
| 35S:tr-NR (n = 37) | 988 | 103 |
| E4:tr-NR (n = 31) | 1124 | 96 |
| 35S:GOGAT (n = 36) | 1277 | 119 |
| E4:GOGAT (n = 31) | 1426 | 113 |
| Rocky Mount |  |  |
| WT (n = 38) | 1240 | 121 |
| 35S:S523D-NR (n = 27) | 69 | 10 |
| E4:S523D-NR (n = 43) | 1135 | 96 |
| 35S:tr-NR (n = 31) | 838 | 95 |
| E4:tr-NR (n = 43) | 1084 | 88 |
| 35S:GOGAT (n = 43) | 1247 | 110 |
| E4:GOGAT (n = 32) | 1292 | 121 |

A statistical analysis of the combined dataset for both locations is shown in Table 4. Table 4 shows the effects of nitrate-related gene constructs on $NO_3^-$ (N) content (ppm of dry weight) in the leaves of T2 generation transgenic burley plants at maturity. The 35S:S523D-NR group accumulated significantly less nitrate than any other genotype. Though not nearly as dramatic of a reduction, the free nitrate levels in the other plant genotypes containing a deregulated nitrate reductase cDNA (35S:tr-NR, E4:tr-NR and E4:S532D-NR) also accumulated less nitrate than the WT group, but only the plants containing the 35S:tr-NR construct were considered significantly different than the GOGAT-expressing control genotypes. The nitrate content of the E4:GOGAT and 35S:GOGAT groups was not considered significantly different than WT.

TABLE 4

Means with the same letter are not significantly different at $\alpha = 0.05$.

| REGWQ Grouping | Mean | N | Genotype |
|---|---|---|---|
| A | 1378.29 | 78 | WT |
| BA | 1358.02 | 63 | E4:GOGAT |
| BAC | 1260.73 | 79 | 35S:GOGAT |
| BDC | 1123.07 | 75 | E4:S523D-NR |
| DC | 1100.96 | 74 | E4:tr-NR |
| D | 919.35 | 68 | 35S:tr-NR |
| E | 65.73 | 59 | 35S:S523D-NR |

The stalked-harvested plants that were transferred to the curing barn were allowed to air-cure for approximately 10 weeks. At the end of this period an additional two leaves from the upper third stalk position were harvested, stripped of the mid-rib, and placed in paper bags. Although the materials were very dry at the post-cure harvest, the bags were placed in a dryer at room temperature with the blowers running to ensure complete dryness (heat was not added due to the potential influence of high temperature on TSNA formation). The dried samples were ground and subjected to nitrate analysis. Table 5 shows the effects of nitrate-related gene constructs on $NO_3^-$ N content (ppm of dry weight) in the leaves of T2 generation transgenic burley plants after eight weeks of air-curing. Comparison of the data on Table 4 with those presented on Table 5 reveal that the nitrate content in the lamina of the leaves for all genotypes was ~2-fold higher after air-curing. Although the mechanism is unknown, an increase in leaf nitrate concentration is commonly observed after air-curing in burley tobaccos. Similar to the results obtained using mature, non-cured tissue, plants of the 35S:S523D-NR genotype accumulated far less free nitrate than any other genotypic group, and only ~4% of that observed in WT plants (Table 5). Cured leaf samples of other genotypes containing deregulated NR constructs also continued to display statistically significant reductions in nitrate content compared to WT plants, ranging from 70% to 77% of the nitrate concentration observed in the WT group.

TABLE 5

Means with the same letter are not significantly different at α = 0.05.

| REGWQ Grouping | MEAN | N | Genotype |
|---|---|---|---|
| A | 2806.1 | 79 | WT |
| BA | 2493.3 | 63 | E4:GOGAT |
| BA | 2451.4 | 79 | 35S:GOGAT |
| BC | 2149.9 | 76 | E4:tr-NR |
| C | 2035.1 | 75 | E4:S523D-NR |
| C | 1974.7 | 70 | 35S:tr-NR |
| D | 107.4 | 60 | 35S:S523D-NR |

Although nitrite levels in plants are generally very low, presumably due to the efficiency of the endogenous nitrite reductase activities, the dramatic metabolism of the cellular nitrate reserves mediated by the constitutively expressed S523D-NR enzyme may result in an increase in the levels of its end product nitrite. Given that nitrite is ultimately the compound believed to be responsible for TSNA formation during air-cure, it is important that genetic modifications that lead to reductions in nitrate pools do not result in an increase in the levels of nitrite within the cured leaf. To determine whether the overexpression of any of the transgene constructs was associated with changes in leaf nitrite content, nitrite assays were conducted on all of the air-cured leaf samples collected. Overall, the nitrite levels among the various genotypes were similar (Table 6). Table 6 shows the effects of nitrate-related gene constructs on $NO_2^-$ content (ppm of dry weight) in the leaves of T2 generation transgenic burley plants after eight weeks of air-curing.

TABLE 6

Means with the same letter are not significantly different at α = 0.05.

| REGWQ Grouping | Mean | N | Genotype |
|---|---|---|---|
| A | 2.4403 | 63 | E4:GOGAT |
| BA | 2.3559 | 79 | WT |
| BA | 2.3236 | 75 | E4:S523D-NR |
| BA | 2.3052 | 79 | 35S:GOGAT |
| BA | 2.279 | 76 | E4:tr-NR |
| BA | 2.1125 | 70 | 35S:tr-NR |
| B | 1.9574 | 60 | 35S:S523D-NR |

Although the numeric mean of the 35S:S523D-NR group was the lowest of all the genotypes, it was not considered to be statistically significant from the WT controls (though it was deemed significantly lower than the E4:GOGAT line). These results show that the constitutive expression of the deregulated S523D-NR construct does not result in increased nitrite levels; instead it is possible that this transgene may mediate a modest decrease in the nitrite concentrations of the cured leaf.

To test whether reducing leaf nitrate content would impact TSNA or alkaloid accumulation, a subset of the above described cured leaf samples of the WT, 35S:S523D-NR and 35S:GOGAT genotypes were selected for further analysis. For each genotype, a total of 33 leaf samples were chosen, evenly distributed between the two locations (16 from Clayton, 17 from Rocky Mount) and selected from individual rows in which all three genotypes were represented (i.e., no dead plants for any of the three genotypes within an given selected row). The results of the TSNA and alkaloid analyses are shown in Table 7. Table 7 shows the TSNA and alkaloid content in cured leaves of WT, 35S:GOGAT and 35S:S523D-NR plants. Cumulatively, the total reduction in TSNA content in the 35S:S523D-NR genotype compare with WT was 77.5%. No statistically significant differences were observed between any individual TSNA, or total TSNA content in WT plants versus the 35S:GOGAT plants. These results clearly demonstrate that constitutive expression of the S523D-NR construct lead to substantial reductions in the TSNA content of air-cured tobacco leaves, a phenomenon most likely attributable to its ability to dramatically reduce the levels of free nitrate within the leaf.

TABLE 7

|  | WT | 35S:GOGAT | 35S:S523D-NR |
|---|---|---|---|
| Total TSNA (ng/g) | 709 | 649 | 162 |
|  | A | A | B |
| NNN (ng/g) | 287 | 288 | 31 |
|  | A | A | B |
| NAT (ng/g) | 293 | 257 | 83 |
|  | A | A | B |
| NAB (ng/g) | 17 | 14 | 0.3 |
|  | A | A | B |
| NNK (ng/g) | 111 | 91 | 48 |
|  | A | A | B |
| Total alkaloid (%) | 2.6 | 2.8 | 2.6 |
|  | A | A | A |
| Nicotine (%) | 2.5 | 2.6 | 2.4 |
|  | A | A | A |
| Nornicotine (%) | 0.058 | 0.063 | 0.058 |
|  | A | A | A |
| Anabasine (%) | 0.011 | 0.011 | 0.012 |
|  | A | A | A |
| Anatabine (%) | 0.075 | 0.075 | 0.091 |
|  | A | A | A |
| Conversion (%) | 2.4 | 2.6 | 2.5 |
|  | A | A | A |

Means with the same letter are not significantly different at alpha = 0.01. Alkaloid measurements represent % dry weight. Means are grouped according to the REGWG method, N = 33.

No significant differences were observed in either total alkaloid content, or for any individual alkaloid assayed (nicotine, nornicotine, anabasine and anatabine) among the three genotypes. In contrast, major differences in TSNA content were apparent in the low nitrate containing 35S:S523D-NR leaf materials. A 90% reduction in the levels of NNN was observed in the 35S:S523D-NR group compared to WT controls. N-nitrosoanatabine (NAT) and NNK accumulation was reduced by 72.5% and 55%, respectively, in 35S:S523D-NR versus WT plants. While N-nitrosoanabasine (NAB) is typically the least abundant of the TSNAs in cured tobacco leaves, in the 35S:S523D-NR plants the presence of this compound was nearly undetectable (Table 7).

The low nitrate phenotype mediated by the 35S:S523D-NR construct was associated with major reductions in the TSNA content of the cured leaf, consistent with the model of TSNA formation in air-cured tobaccos that postulates that leaf surface microbes utilize leaf nitrate pools to produce the nitrite that is directly responsible for the nitrosation of tobacco alkaloids. Although the concentrations of nitrate, alkaloids and TSNAs varied considerably in the tobacco plant in accordance to the stalk position of the leaf, the 35S:S523D-NR construct was effective in mediating reductions in nitrate and TSNAs throughout the entire plant, as major reductions in these compounds were observed both in select upper position leaves, and in samples of cut filler tobacco produced from the remainder of the plant, skewed heavily in favor of lower stalk leaves. In contrast, nicotine levels were not significantly altered as a consequence of 35S:S523D-NR-mediated nitrate reduction.

Example 5

Analysis of the Cut Filler and Smoke from Cigarettes Made with Low Nitrate Tobacco Plants To determine the impact of the reduced nitrate phenotype on the prevalence of TSNAs in mainstream smoke, cigarettes were made from pooled samples of the remaining cured leaf materials of the 35S:S523-NR plants and the WT controls. The first two leaf samplings described in the previous section were taken from the upper third stock position; therefore, the remaining leaf tissue used for making the cut filler was greatly skewed towards leaves from lower stalk positions of the plant. Because the relative concentrations of nitrate, nicotine and TSNAs differ in accordance to stalk position, it was important to independently determine the levels of these compounds as represented in the cut filler in order to accurately interpret the corresponding smoke data.

Figure 10:
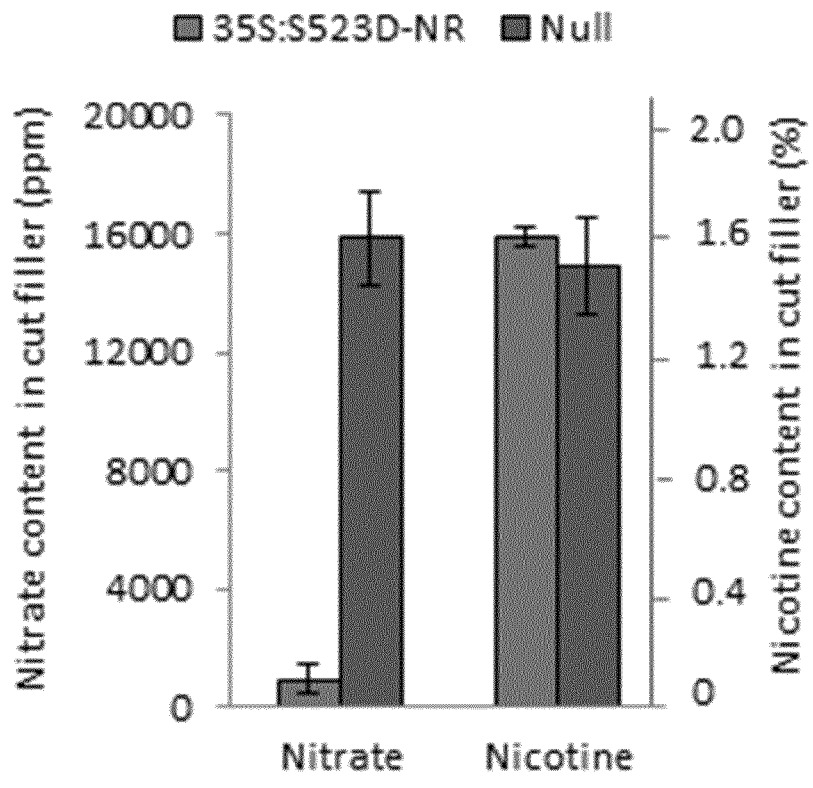
FIG. 10 shows the average nitrate and nicotine content in cut tobacco filler derived from the lamina of WT and 35S:S523D-NR genotypes.
Figure 11A:
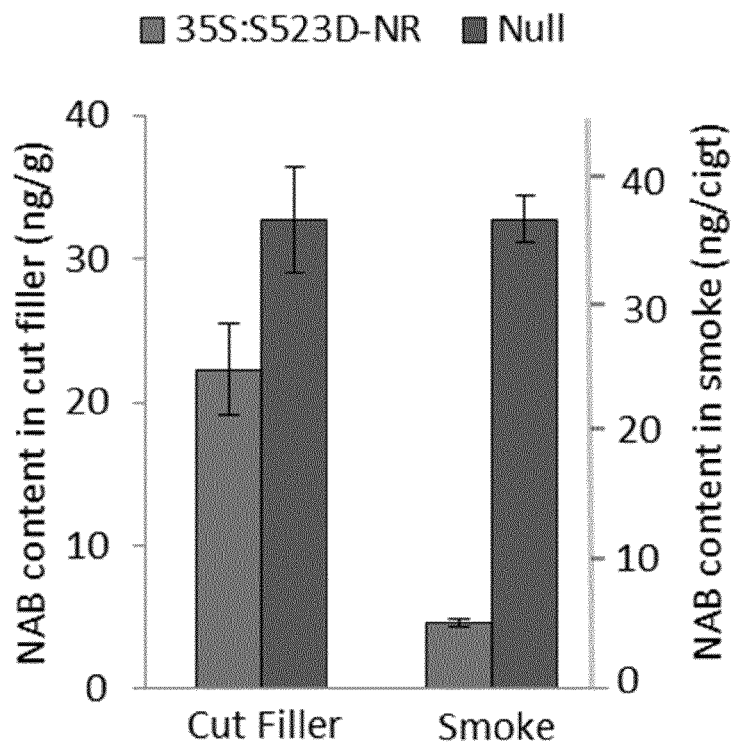
FIGS. 11A-11E shows the average content of NAB (FIG. 11A), NAT (FIG. 11B), NNK (FIG. 11C), NNN (FIG. 11D), and total TSNAs (FIG. 11E) in the cut filler and smoke of cigarettes made from the lamina of WT and 35S:S523D-NR leaves.
Figure 11B:
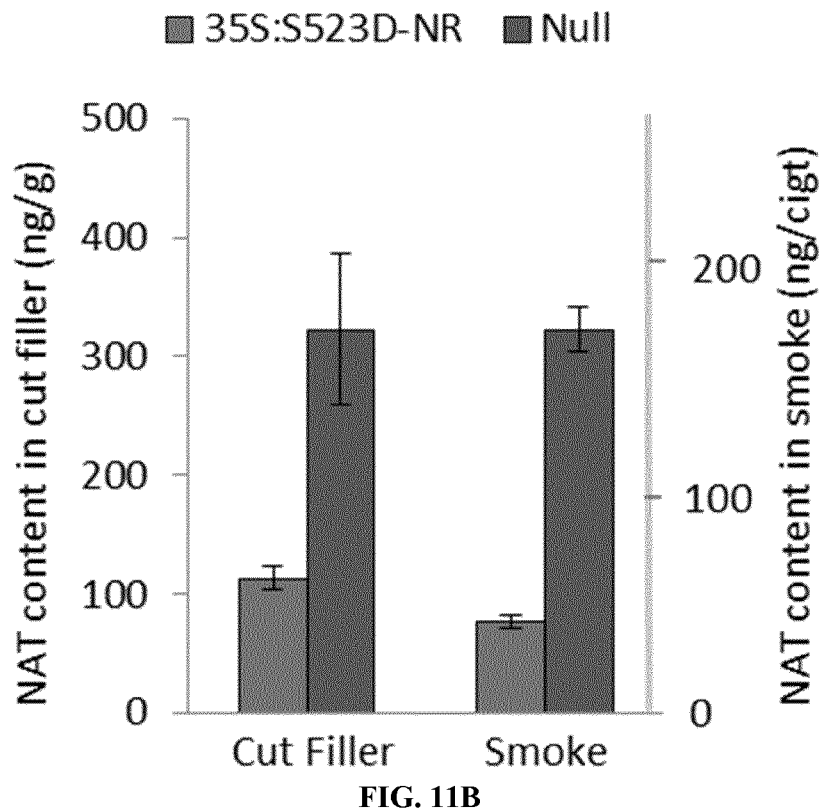
Figure 11C:
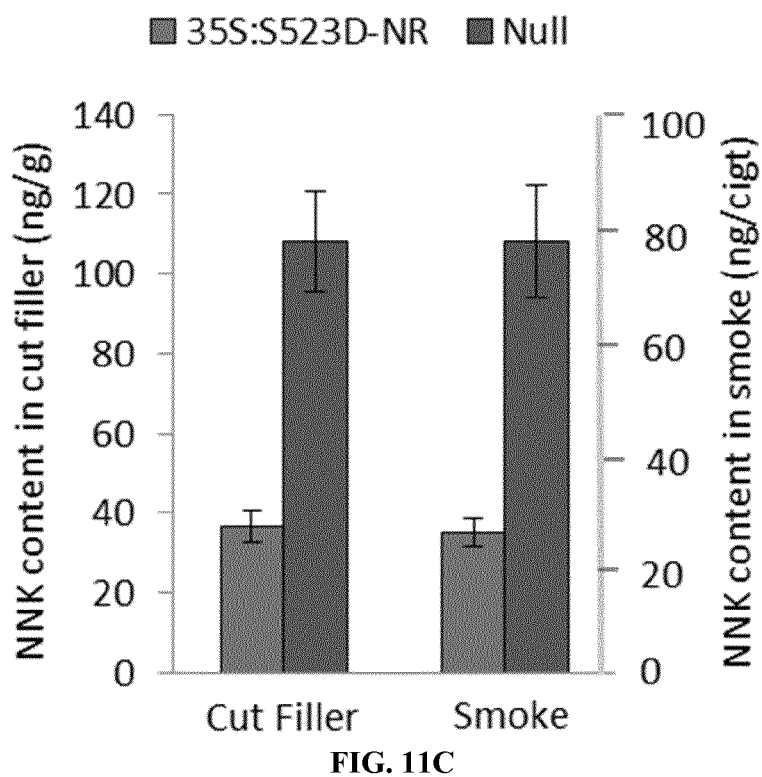
Figure 11D:
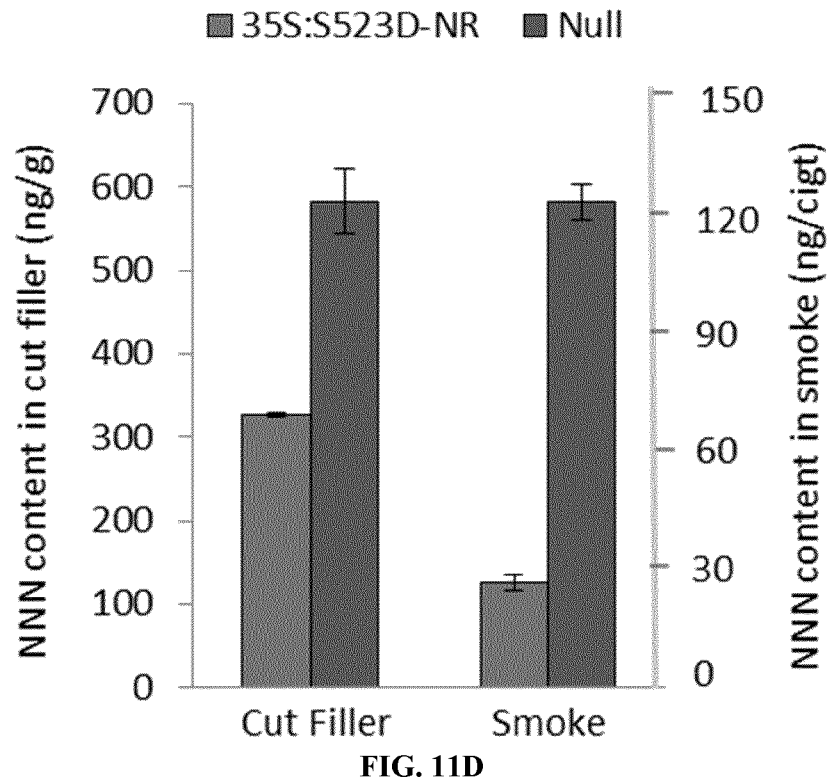
Figure 11E:
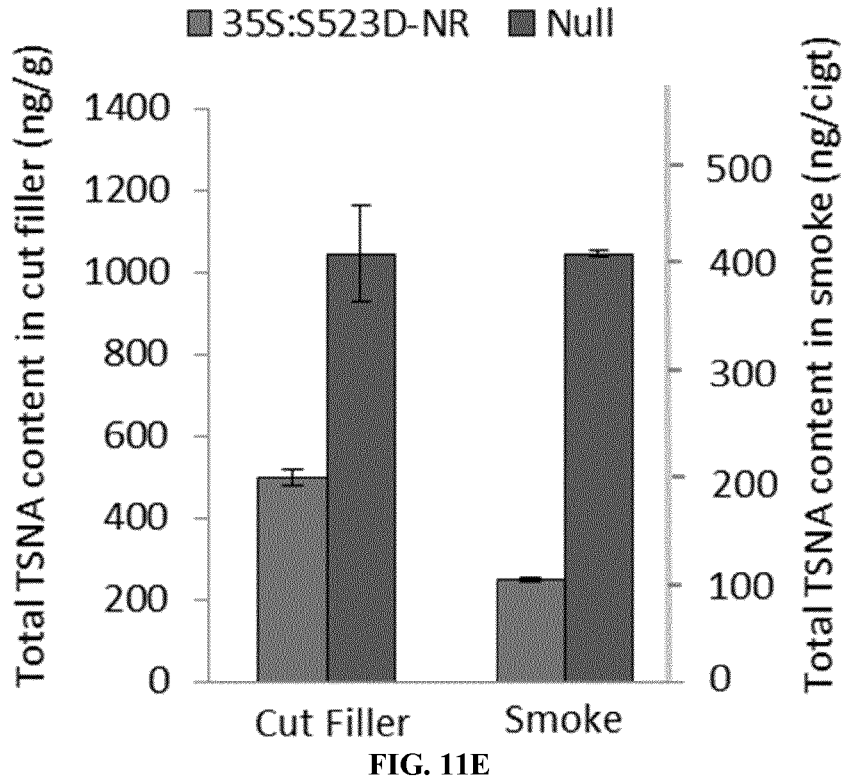

As shown in FIG. 10, the nitrate concentration averaged 15,800 ppm in the cut filler made from WT leaf lamina. In contrast, in cut filler generated from 35S:S523D-NR plants, nitrate levels averaged 930 ppm, a value approximately 5.9% of that observed in the WT filler, and consistent with the ratio observed between these two genotypes in cured, upper stalk leaves (Table 5). The overall higher concentrations of nitrate measured in the cut filler of WT and 35S:S523D-NR plants compared to the upper leaf readings (compare Table 5 and FIG. 10) is consistent with previous observations that the nitrate levels in the bottom leaves of tobacco are greatly higher than that found in the top leaves. In FIG. 10, all plant materials of each genotype were pooled according to location (about 30 plants each from Clayton and Rocky Mount for 35S:S523D-NR; about 40 plants each from the two locations for WT). Data shown represents the average and standard error across both locations. Nicotine concentration in tobacco leaves displays the opposite trend, with the upper leaves showing higher concentrations than the lower leaves though the magnitude of the differential is not as extreme as observed with nitrate. Nicotine content in the cut filler of WT and 35S:S523D-NR plants averaged 1.6% and 1.7% dry weight, respectively (FIG. 10), compared to 2.5% and 2.4% in their respective upper leaves (Table 7). In either case, despite its tremendous impact on leaf nitrate content, constitutive expression of the S523D-NR construct did not significantly alter the nicotine levels of the leaf.

Results of the TSNA analyses of the cut filler tobaccos are shown in FIGS. 11A-11E. Similar to the observations using cured upper leaf materials (Table 7), major reductions were observed in each of the four TSNA species using leaf material from low nitrate plants, though some differences were observed in the relative extent of the respective reductions. Cut filler derived from 35S:S523D-NR plants contained 44%, 64%, 65% and 32% less NNN, NNK, NAT and NAB, respectively, than filler made from WT control plants, with a total observed TSNA reduction of 52%. Overall TSNA levels were somewhat higher in the cut filler material compared to cured upper leaves (compare Table 7 and FIG. 11), a result consistent with previous observations that TSNA accumulation is higher in leaves from lower stalk positions than top position leaves. In FIG. 11, leaf materials of each genotype were pooled according to each of two locations as described in FIG. 10. Data shown represents the combined means and standard error of two replications per location for the TSNA content of the cut filler, and three replications per location for TSNA content in mainstream smoke.

TSNA data from mainstream smoke derived from cigarettes made with the WT and 35S:S523D-NR cut filler is also shown in FIG. 11. Surprisingly, the amount of total TSNA reduction attributable to the low nitrate phenotype is even greater in the mainstream smoke than that observed in the corresponding cut filler. The mainstream smoke of 35S:S523D-NR cigarettes showed a 76% reduction in total TSNA content compared to WT cigarettes, as opposed to the 52% reduction observed in their cut filler tobacco (FIG. 11E). The differences in the extent of reduction in TSNA content between 35S:S523D-NR and WT cut filler tobaccos versus their corresponding mainstream smoke are most pronounced for NNN and NAB. The NNN content of unburned filler tobacco from 35S:S523D-NR plants was 44% less than the WT filler, yet the differential in the mainstream smoke increased to 78% (FIG. 11D). Likewise, NAB levels of 35S:S523D-NR plants were 32% lower than WT in the filler, compared to an 86% reduction in the mainstream smoke (FIG. 11A). Of the four TSNA species measured, only NNK failed to show a statistically significant differential in its relative reduction in the cut filler versus mainstream smoke when the results of WT and 35S:S523D-NR cigarettes were compared. In both the cut filler and mainstream smoke, NNK was reduced by approximately 67% in cigarettes made using the low nitrate 35S:S523D-NR tobacco compared to the WT tobacco control (FIG. 11C). The relative reduction in the levels of all TSNA species, except NNK, was even greater in the mainstream smoke of the low nitrate cigarettes than in the corresponding unburned cut filler.

The 35S:S523D-NR-mediated reduction in nitrate levels may mitigate the problem of TSNAs in tobacco products at two levels: (1) by reducing the production of TSNAs within the cured leaf per se; and (2) by further inhibiting the processes by which TSNAs appear in the mainstream smoke.

Example 6

Overexpression of S523D-NR in an Additional Burley Background Results in Dramatic Reductions in Leaf Nitrate Accumulation The plant expression vectors containing the 35S:S523D-NR and E4:S523D-NR constructs were used to transform burley cultivar TN90e4e5. In addition to generating plants containing the 35S:S523D-NR and E4:S523D-NR constructs individually, both constructs were combined into the same plant to determine if additional reductions in nitrate beyond that attainable by a single construct could be obtained. To obtain T0 plants with each transgene and transgene combination, a co-transformation strategy was employed. To distinguish the complement of transgenes in each T0 plant recovered, PCR-based genotyping was conducted using a 5' primer specific for either the 35S or E4 promoter regions, paired with a 3' primer directed against the S523D-NR region of the construct. As a vector control, TN90e4e5 leaf discs were also transformed with a construct containing the GUS reporter gene under the transcriptional control of the E4 promoter.

Once the plants were large enough to transfer to soil, the following T0 lines were grown to maturity in a greenhouse: E4:GUS vector control (12 events); 35S:S523D-NR (10 events); E4:S523D-NR (11 events); and 35S:S523D-NR+ E4:S523D-NR (7 events). Plants were grown in a standard soil mix fertilized with Multicote 4, a controlled release fertilizer (14-14-16 NPK+minor nutrients). Just prior to the initiation of flowering, two leaves from the mid-upper section of each plant were harvested, the mid-ribs removed, and the remaining lamina dried at 65° C. At the same harvest date, two additional leaves were taken from the same section of each plant and treated with ethephon to induce senescence as described by Jack et al. (Rec. Adv. Tob. Sci. 33:58-79 (2007)). Once the ethephon-treated leaves had completely yellowed (7-8 days after treatment), a portion of each leaf was frozen for real time PCR (RT-PCR) analysis, while the remaining leaf tissue was allowed to dry to completeness for subsequent nitrate analysis.

Table 8 shows the nitrate content of the green and "artificially senescent" leaf samples from the T0 plants (i.e., TN90 e4e5 T0 plants). All 12 independent E4:GUS vector control plants displayed high levels of nitrate in their leaves, ranging from 3,938 to 12,730 parts per million (ppm). In general, the nitrate concentration in the green leaf was very similar to that observed in the ethephon treated leaves. Unlike the E4:GUS controls, five out of ten independent 35S:S523D-NR T0 events accumulated less than 1000 ppm, with three individuals accumulating 300 ppm or less in both green and ethephon treated samples. All 11 E4:S523D-NR individuals showed high nitrate accumulation in the green leaf (greater than 3,987 ppm).

TABLE 8

| Transgene construct | Green Leaf NO3 (ppm) | Ethephon Treated Leaf NO3 (ppm) |
| --- | --- | --- |
| Vector control 1-3 | 11,122 | 12,102 |
| Vector control 2-7 | 9,965 | 10,615 |
| Vector control 3-6 | 10,933 | 11,786 |
| Vector control 4-2 | 11,006 | 10,135 |
| Vector control 5-7 | 7,466 | 7,238 |
| Vector control 6-1 | 4,646 | 6,473 |
| Vector control 7-2 | 3,938 | 5,344 |
| Vector control 8-6 | 11,091 | 9,956 |
| Vector control 9-3 | 8,930 | 11,325 |
| Vector control 10-4 | 9,875 | 11,964 |
| Vector control 11-5 | 10,983 | 10,841 |
| Vector control 12-2 | 12,730 | 10,499 |
| 35S:S523D-NR 1-2 | 10,978 | 8,869 |
| 35S:S523D-NR 2-2 | 4,200 | 2,616 |
| 35S:S523D-NR 3-1 | 404 | 383 |
| 35S:S523D-NR 4-3 | 779 | 888 |
| 35S:S523D-NR 5-5 | 126 | 106 |
| 35S:S523D-NR 6-3 | 3,197 | 2,648 |

TABLE 8-continued

| Transgene construct | Green Leaf NO3 (ppm) | Ethephon Treated Leaf NO3 (ppm) |
| --- | --- | --- |
| 35S:S523D-NR 7-4 | 162 | 136 |
| 35S:S523D-NR 8-5 | 188 | 300 |
| 35S:S523D-NR 9-6 | 10,751 | 10,034 |
| 35S:S523D-NR 10-5 | 8,241 | 8,659 |
| E4:S523D-NR 1-4 | 9,487 | 3,299 |
| E4:S523D-NR 3-4 | 10,549 | 3,052 |
| E4:S523D-NR 4-1 | 8,853 | 3,886 |
| E4:S523D-NR 5-3 | 9,725 | 4,043 |
| E4:S523D-NR 6-2 | 6,795 | 2,517 |
| E4:S523D-NR 7-1 | 3,987 | 1,804 |
| E4:S523D-NR 8-2 | 7,670 | 3,437 |
| E4:S523D-NR 9-7 | 6,797 | 2,859 |
| E4:S523D-NR 10-3 | 4,938 | 3,218 |
| E4:S523D-NR 11-2 | 9,685 | 3,993 |
| E4:S523D-NR 12-3 | 8,470 | 4,334 |
| 35S + E4:S523D-NR 1-7 | 7,689 | 3,921 |
| 35S + E4:S523D-NR 3-3 | 7,348 | 3,808 |
| 35S + E4:S523D-NR 4-5 | 5,501 | 5,694 |
| 35S + E4:S523D-NR 5-2 | 146 | 159 |
| 35S + E4:S523D-NR 7-7 | 6,686 | 2,256 |
| 35S + E4:S523D-NR 8-1 | 238 | 0 |
| 35S + E4:S523D-NR 9-5 | 8,522 | 9,680 |

In ethephon treated leaves derived from the same plants, however, a 2- to 3-fold reduction in nitrate levels was observed (Table 8). It is expected that the E4 promoter that controls the expression of S523D-NR in these plants is inactive in green leaves, but becomes highly expressed during ethephon treatment, senescence and air-curing. Two of the seven T0 plants containing both the 35S:S523D-NR and E4:S523D-NR constructs showed very low levels of nitrate in the green leaf (146 and 238 ppm). Low levels of nitrate in the green tissue of these plants suggest that the 35S:S523D-NR construct is actively expressed in these two individuals. In one of these plants (35S+E4:S523D-NR 5-2), the levels of nitrate in the green versus ethephon treated leaves remained virtually the same. In the other plant (35S+E4:S523D-NR 8-1), however, free nitrate was undetectable in the ethephon treated leaves. Maximal reduction in nitrate accumulation may be achieved by combining a construct driving strong constitutive expression of S523D-NR with a construct mediating strong senescence/curing-specific expression of S523D-NR. Notably, there were no obvious phenotypic differences observed between T0 plants possessing exceptionally low levels of free nitrate and T0 individuals displaying normal levels of nitrate.

Figure 12:
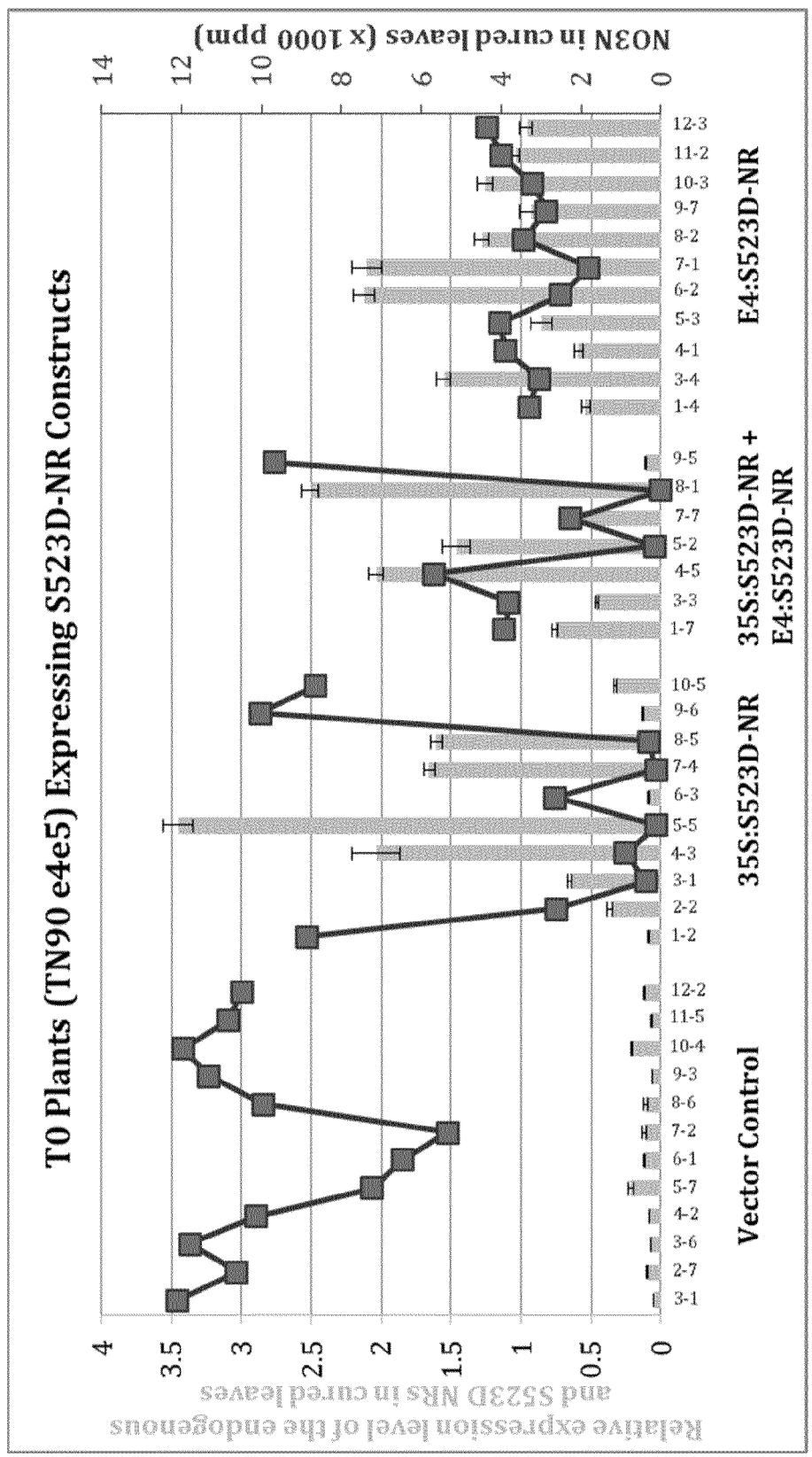
FIG. 12 shows the nitrate concentration and relative NR transcript levels in ethephon-treated tobacco leaves containing S523D-NR constructs under the transcriptional control of the 35S CaMV promoter and/or the ethephon-inducible CYP82E4 (E4) promoter.

Due to phenomena such as "position effects" and gene silencing, it is common in any given transformation experiment to observe great variability in the transcript accumulation levels among different T0 events. The results of the nitrate assays on the T0 plants suggested that the S523D-NR transgene was being effectively expressed in some individuals, but not in others (particularly with respect to the 35S:S523D-NR construct). To test this, an RT-PCR analysis was conducted on the yellowed ethephon-treated samples described above. RT-PCR analysis using green leaf tissues were confounded by the fact that the assay did not distinguish between the endogenous Nia2 transcripts and the S523D-NR-derived transcripts (as their coding regions only differ at a single codon), and a high level of native NR transcript was detected in green leaf tissue of the control plants. In contrast, minimal endogenous NR transcript accumulation was detected in the artificially senescent ethephon-treated leaves. FIG. 12 shows the relative NR transcripts levels (normalized to a tobacco elongation factor 1α gene) in the ethephon-treated leaves of each T0 plant listed in Table 8, together with the corresponding nitrate concentration. In FIG. 12, the RT-PCR data (yellow bars, scale on left) show the relative accumulation of NR transcripts (both endogenous NR and S523D-NR) after normalization to a tobacco elongation factor 1α reference transcript. Red boxes indicate nitrate concentration (scale on right). Endogenous NR transcript accumulation is relatively low and nitrate content is high (greater than 5,000 ppm) in all vector control plants. In T0 plants containing only the 35S:S523D-NR construct there is a very good correlation between high NR transcript accumulation and the low nitrate phenotype. All T0 plants possessing only the E4:S523D-NR transgene displayed a higher level of NR transcript accumulation than the vector controls, and their corresponding nitrate levels were also uniformly lower. It is not surprising that nitrate levels are not driven as low in the E4:S523D-NR plants compared to the high expressing 35S:S523D-NR plants, given that the deregulated NR enzyme would be expected to be contributing toward reducing the nitrate pools only after ethephon treatment in the former plants, and not throughout the entire life of the plant as would be expected for the latter individuals. A substantial proportion of the NR transcripts in plants 5-2 and 8-1 within this group may initiate from the 35S:S523D-NR construct, given the exceptionally low levels of nitrate observed in both the green and ethephon-treated leaf samples from these plants (Table 8).

Example 7

Over-Expression of S523D-NR in T1 Plants Shows Dramatic Reduction in Leaf Notrate Accumulation T1 transgenic plants in the TN90e4e5 background (including controls, 1920 plants) from float trays were genotyped and transplanted at two field locations (fully randomized field design). Leaf tissue samples (lamina) from each plant were collected for nitrate analysis and the plants placed then in an air-curing structure to generate cut-filler for cigarette smoke analyses.

Nitrate data from green leaves collected at mid-stalk position at the two field locations are presented in Tables 9 and 10. The data showed in both case a strong reduction of nitrate due to the presence of the transgene.

TABLE 9

The effects of deregulated nitrate reductase gene constructs on free NO3N content in green leaves of T1 transgenic plants under 300 kg/ha N fertilization

| REGWQ Grouping | Mean (ppm) | N | T1 Line | Genotype |
|---|---|---|---|---|
| A | 1357 | 40 | | Wild Type |
| A | 864 | 39 | GH10-4 | E4:GUS |
| B | 22 | 27 | GH8-1 | 35S:S523D-NR + E4:S523D-NR |
| B | 20 | 35 | GH3-1 | 35S:S523D-NR |
| B | 18 | 34 | GH5-2 | 35S:S523D-NR |
| B | 18 | 39 | GH8-5 | 35S:S523D-NR |
| B | 15 | 36 | GH5-2 | 35S:S523D-NR + E4:S523D-NR |
| B | 15 | 34 | GH8-1 | 35S:S523D-NR |
| B | 14 | 36 | C3-11 | 35S:S523D-NR |
| B | 13 | 36 | GH5-5 | 35S:S523D-NR |

Means with the same letter are not significantly different at alpha = 0.05. All "GH" lines are in a TN90e4e5 background; C3-11 is a line in DH98-325-6#775 that was included in the 2013 field study. Logarithms of the original data were used in analyses, but the means of the original data are shown for convenience.

TABLE 10

The effects of deregulated nitrate reductase gene constructs on free NO3N content in cured leaves of T1 transgenic plants under 300 kg/ha N fertilization

| REGWQ Grouping | Mean (ppm) | N | T1 Line | Genotype |
|---|---|---|---|---|
| A | 1698 | 40 | | Wild Type |
| A | 1215 | 39 | GH10-4 | E4:GUS |
| B | 29 | 34 | GH5-2 | 35S:S523D-NR |
| B | 28 | 36 | C3-11 | 35S:S523D-NR |
| B | 21 | 36 | GH5-5 | 35S:S523D-NR |
| B | 20 | 36 | GH3-1 | 35S:S523D-NR |
| B | 20 | 38 | GH8-5 | 35S:S523D-NR |
| B | 19 | 34 | GH8-1 | 35S:S523D-NR |
| B | 17 | 29 | GH8-1 | 35S:S523D-NR + E4:S523D-NR |
| B | 15 | 34 | GH5-2 | 35S:S523D-NR + E4:S523D-NR |

Means with the same letter are not significantly different at alpha = 0.05. All "GH" lines are in a TN90e4e5 background; C3-11 is a line in DH98-325-6#775 that was included in the 2013 field study. Logarithms of the original data were used in analyses, but the means of the original data are shown for convenience.

We can conclude from this experiment that expressing the 35S:S523D-NR transgene in the more vigorous TN90e4e5 background is just as effective in lowering leaf nitrate content as was observed in the inferior line DH98 325-6#775.

Figure 13:
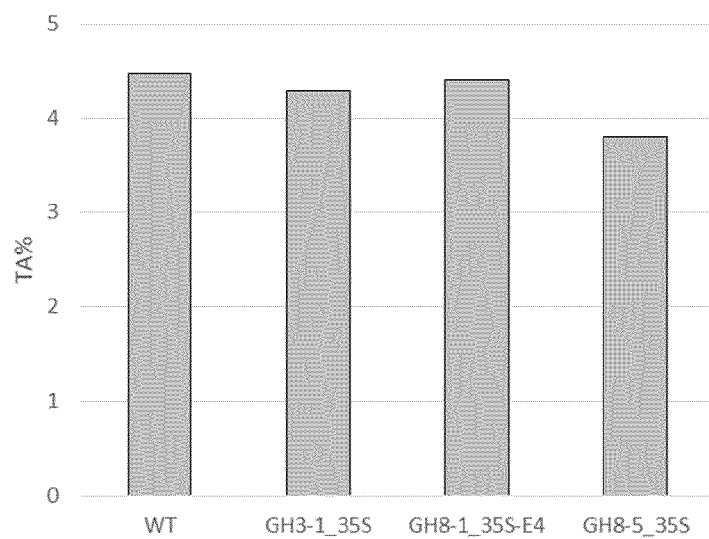
FIG. 13 shows total alkaloid content (TA % DW) in 35S:S523D-NR and 35S:S523D-NR/E4:S523D-NR transgenic lines, GH3-1, GH8-1 and GH8-5, respectively.

Some lines (GH3-1, GH8-1 and GH8-5) were selected to analyze nitrate and total alkaloids in cured leaves (mid-stalk position, bulk powder representative of plant plots). Generally, as observed before, total alkaloids and nicotine were not affected by the presence of the transgene (35S:S523D-NR). However in the TN90e4e5 background, a slight reduction (15%) was observed in one line, GH8-5 (FIG. 13).

Figure 14:
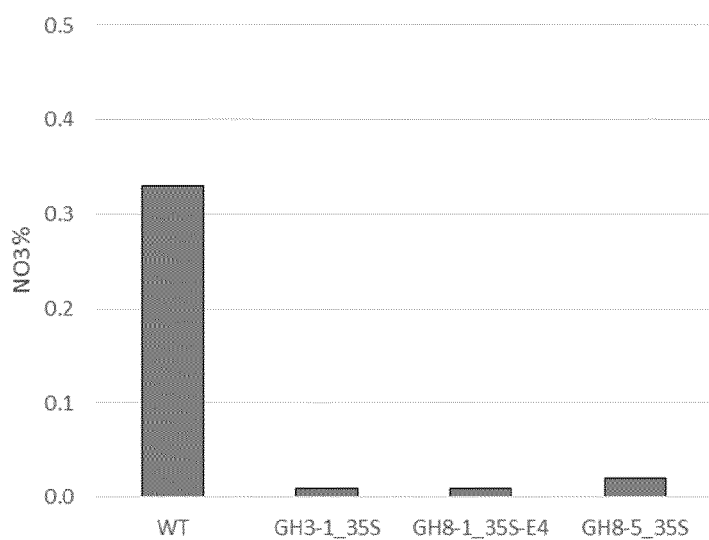
FIG. 14 illustrates nitrate content (NO3% DW) in three 35S:S523D-NR and 35S:S523D-NR/E4:S523D-NR transgenic lines, GH3-1, GH8-1 and GH8-5, respectively.

As expected from previous results, leaf nitrate is strongly reduced (>95%) in the lamina due to a more active nitrate assimilation. The addition of a transgene regulated by the senescence promoter E4 did not affect the data, thereby suggesting that the activity of the transgenic nitrate reductase under the control of the constitutive promoter 35S is strongly efficient in the green (see Tables 9 and 10) and enough to reduce nitrate stored in the leaf lamina (FIG. 14).

Cut-filler were produced from cured leaves and analyzed for TSNAs. Interestingly, TSNAs were markedly reduced (~72% for NNN, ~45% for NNK, ~76% for NAT and ~78% for NAB), indicating that lowering nitrate in green leaves strongly affect the production of TSNAs in cut-filler material (FIG. 15).

Figure 15:
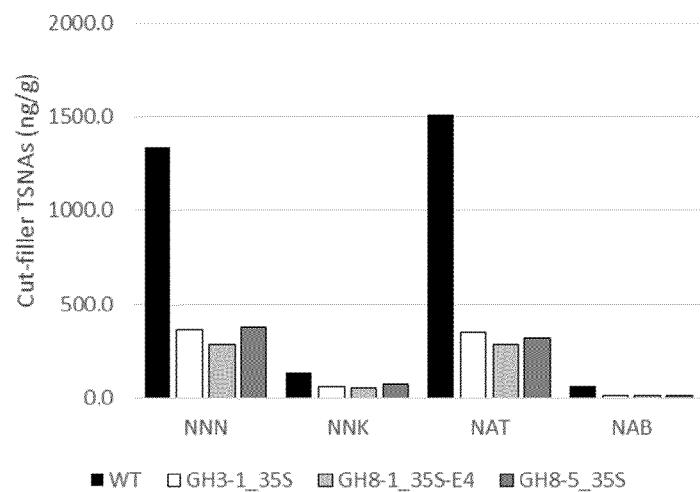
FIG. 15 shows TSNAs (NNN, NNK, NAT and NAB, ng/g) content in the cut-filler of three 35S:S523D-NR and 35S:S523D-NR/E4:S523D-NR transgenic lines, GH3-1, GH8-1 and GH8-5, respectively.
Figure 16:
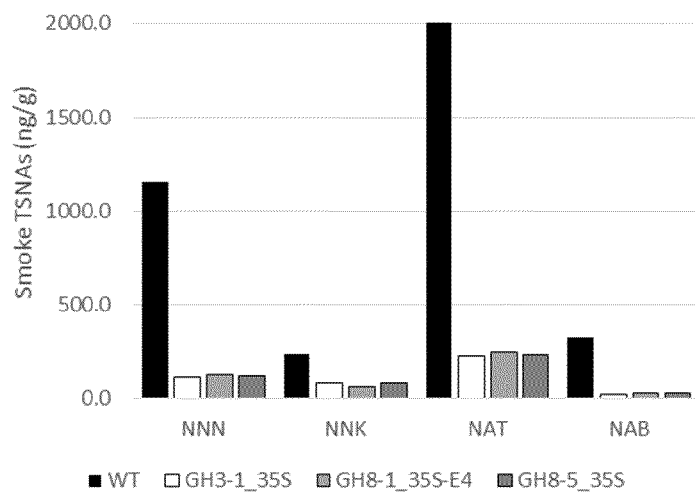
FIG. 16 shows TSNAs (NNN, NNK, NAT and NAB, ng/g) content in smoke of cigarettes made with the cut-filler of three 35S:S523D-NR and 35S:S523D-NR/E4:S523D-NR transgenic lines, GH3-1, GH8-1 and GH8-5, respectively.

Exactly as for the inferior line DH98 325-6#775 transformed with 35S:S523D-NR (see Example 2), cigarettes were made with the material analyzed in FIG. 15 and smoked. The TSNAs were determined in smoke and the data reported in the FIG. 16. TSNAs were even more reduced in smoke (~90% for NNN, ~66% for NNK, ~88% for NAT and ~92% for NAB) than in cut-filler, certainly due to the impact of lower nitrosation during pyrolysis. Thus, globally, this indicates that lowering nitrate in green leaves by overexpressing a deregulated form of nitrate reductase strongly reduce the production of TSNAs in smoke of commercial tobacco, like TN90e4e5.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limita- For reasons of completeness, various aspects of the invention are set out in the following numbered clauses:

Clause 1. A tobacco product having reduced tobacco specific nitrosamine (TSNA) levels which is generated from a tobacco plant, said tobacco plant being modified to comprise: (i) a polynucleotide comprising, consisting or consisting essentially of a sequence encoding a deregulated nitrate reductase enzyme; (ii) a polypeptide encoded by the polynucleotide set forth in (i); (iii) a polypeptide comprising, consisting or consisting essentially of a deregulated nitrate reductase enzyme; or (iv) a construct, vector or expression vector comprising the polynucleotide set forth in (i), and wherein the expression or activity of said nitrate reductase is deregulated as compared to a control unmodified tobacco plant.

Clause 2. A tobacco product according to clause 1, wherein the deregulated nitrate reductase enzyme is a nitrate reductase enzyme that is constitutively active.

Clause 3. A tobacco product according to clause 1 or 2, wherein the sequence encoding a deregulated nitrate reductase enzyme encodes (i) a truncated nitrate reductase polypeptide; (ii) a nitrate reductase polypeptide which comprises an N-terminal truncation; (iii) a nitrate reductase polypeptide which comprises an N-terminal truncation of 56 amino acids; (iv) a nitrate reductase polypeptide comprising an amino acid substitution at a position corresponding to position 523 of SEQ ID NO: 4; or (v) a nitrate reductase polypeptide comprising an amino acid substitution at a position corresponding to position 523 of SEQ ID NO: 4, wherein the amino acid at position 523 of SEQ ID NO: 4 is substituted to an aspartic acid.

Clause 4. A tobacco product according to any preceding clauses, wherein the polynucleotide encoding a deregulated nitrate reductase is a heterologous polynucleotide encoding a modified nitrate reductase polypeptide.

Clause 5. A tobacco product according to clause 4, wherein the heterologous polynucleotide is linked to a promoter not natively associated with an endogenous nitrate reductase gene.

Clause 6. A tobacco product according to clause 5, wherein the promoter is the Cauliflower Mosaic Virus 35S promoter or CYP82E4 promoter.

Clause 7. A tobacco product according to any preceding clauses, wherein the polynucleotide encoding a deregulated nitrate reductase comprises a polynucleotide sequence of SEQ ID NO: 5 or SEQ ID NO: 7.

Clause 8. A tobacco product according to any one of clauses 1 to 3, wherein the polynucleotide encoding a deregulated nitrate reductase is an endogenous nitrate reductase gene that has been modified by a genome editing system or by a mutagen.

Clause 9. A tobacco product according to clause 8, wherein the genome editing system comprises an engineered CRISPR/Cas-based system, an engineered Transcription Activator-Like effector nuclease, an engineered zinc finger nuclease, or an engineered meganuclease.

Clause 10. A tobacco product according to any preceding clauses, wherein the tobacco is a burley, oriental, dark, cigar-type, and flue-cured tobaccos tobacco.

Clause 11. A tobacco product according to any preceding clauses, having reduced tobacco specific nitrosamine (TSNA) levels compared to a tobacco product derived from a control tobacco plant in which the nitrate reductase enzyme has not been deregulated.

Clause 12. A tobacco product of clause 11, wherein the total TSNA level is measured in a leaf from the tobacco plant, wherein (a) the leaf is freshly harvested; (b) the leaf is cured, stored or processed; or (c) the leaf is air-cured.

Clause 13. The tobacco product of clause 11 or 12, wherein the level of at least one TSNA in the tobacco product is reduced compared to a control level for the at least one TSNA, wherein the at least one TSNA is selected from the group consisting of N-nitrosonornicotine (NNN), 4-(methylnitrosamino)-1-(3-pyridyl)-1-butanone (NNK), N-nitrosoanabasine (NAB), N-nitrosoanatabine (NAT), and combinations thereof.

Clause 14. A tobacco product according to any one of clauses 11 to 13, wherein total levels of TSNA are reduced by at least 50%.

Clause 15. A tobacco product according to clause 11, wherein the TSNA levels are measured in smoke obtained from combustion of leaves of the tobacco plant.

Clause 16. A tobacco product according to clause 15, wherein total TSNA levels in smoke are reduced by at least 70%.

Clause 17. A method for producing a tobacco product wherein TSNA levels measured in smoke obtained from combustion of leaves of a modified tobacco plant are reduced compared to TSNA levels measured in smoke obtained from combustion of an unmodified tobacco plant, comprising: (a) modifying a tobacco plant to comprise: (i) a polynucleotide comprising, consisting or consisting essentially of a sequence encoding a deregulated nitrate reductase enzyme; (ii) a polypeptide encoded by the polynucleotide set forth in (i); (iii) a polypeptide comprising, consisting or consisting essentially of a deregulated nitrate reductase enzyme; or (iv) a construct, vector or expression vector comprising the polynucleotide set forth in (i), and wherein the expression or activity of said nitrate reductase is deregulated as compared to a control unmodified tobacco plant; (b) harvesting tobacco leaves from said modified tobacco plant; and (c) producing a tobacco product from the harvested leaves.

Clause 18. The tobacco product of any one of the preceding clauses, wherein the tobacco plant further comprises a modified nornicotine pathway gene.

Clause 19. The tobacco product of clause 18, wherein the modified nomicotine pathway gene comprises a modified nicotine demethylase gene or cytochrome P450 gene.

Clause 20. The tobacco product of clause 18 or 19, wherein the tobacco plant comprises a modified CYP82E4 or modified CYP82E10 gene.

Clause 21. The tobacco product of clause 20, wherein the modified CYP82E4 gene or modified CYP82E10 gene are inactivated.

Clause 22. The tobacco product of any one of the preceding clauses, wherein the tobacco plant is a variety selected from group consisting of burley, oriental, dark, cigar-type, and flue-cured tobaccos.

Clause 23. The tobacco product of any one of the preceding clauses, wherein the tobacco product is a smoking material, snuff, chewing tobacco, gum, lozenge, or nicotine solution.

Clause 24. A method of producing a tobacco product of any one of clauses 1 to 23, the method comprising: (a) introducing into a plant cell an isolated polynucleotide encoding a modified nitrate reductase gene or modified nitrate transporter gene; (b) regenerating the transformed cell to produce a transgenic plant; and (c) producing a tobacco product from a leaf of the transgenic plant.

Clause 25. A method of producing a tobacco product of any one of clauses 1 to 23, the method comprising: (a) introducing into a plant cell a genome editing system that targets an endogenous nitrate reductase gene; (b) regenerating the transformed cell to produce a transgenic plant; and (c) producing a tobacco product from a leaf of the transgenic plant.

Clause 26. The method of clause 25, wherein the genome editing system binds and cleaves the endogenous nitrate reductase gene to generate the modified nitrate reductase gene.

Clause 27. The method of clause 25 or 26, wherein the genome editing system comprises an engineered CRISPR/Cas9-based system, an engineered Transcription Activator-Like effector nuclease, an engineered zinc finger nuclease, or an engineered meganuclease.

Clause 28. The method of any one of clauses 25 to 27 wherein the genome editing system is transiently expressed in the tobacco plant.

Clause 29. The method of any one of clauses 25 to 27, wherein the genome editing system is incorporated into the genome of the tobacco plant.

Clause 30. The method of any one of clauses 25 to 29, wherein the tobacco plant further comprises a modified nornicotine pathway gene.

Clause 31. The method of clause 30, wherein the modified nornicotine pathway gene comprises a modified nicotine demethylase gene or cytochrome P450 gene.

Clause 32. The method of clause 30 or 31, wherein the tobacco plant comprises a modified CYP82E4 or modified CYP82E10 gene.

Clause 33. The method of clause 32, wherein the modified CYP82E4 gene or modified CYP82E10 gene are inactivated.

Clause 34. The method of any one of clauses 25 to 33, wherein the plant cell is of a tobacco variety selected from group consisting of burley, oriental, dark, cigar-type, and flue-cured tobaccos.

Clause 35. The method of any one of clauses 25 to 34 wherein the tobacco product is a smoking material, snuff, chewing tobacco, gum, lozenge, or nicotine solution.

The following nucleic acid and amino acid sequences are disclosed in the sequence listing attached hereto:
SEQ ID NO:1—Coding region of Nia1 cDNA
SEQ ID NO:2—Predicted protein sequence of Nia1p
SEQ ID NO:3—Coding region of Nia2 cDNA (contains a Ser residue at position 523)
SEQ ID NO:4—Predicted protein sequence of Nia2p
SEQ ID NO:5—Coding region of Nia2 S523D-NR cDNA
SEQ ID NO:6—Predicted protein sequence of S523D-NRp (contains an Asp residue at position 523)
SEQ ID NO:7—Coding region of tr-NR cDNA

The invention claimed is:

1. A tobacco product having reduced tobacco specific nitrosamine (TSNA) levels, wherein the tobacco product comprises cured plant tissue from a from a tobacco plant of the species *Nicotiana tabacum*, said tobacco plant being modified to comprise:
   (i) a polynucleotide comprising, consisting or consisting essentially of a sequence encoding a deregulated nitrate reductase enzyme;
   (ii) a polypeptide encoded by the polynucleotide set forth in (i);
   (iii) a polypeptide comprising, consisting or consisting essentially of a deregulated nitrate reductase enzyme; or
   (iv) a construct, vector or expression vector comprising the polynucleotide set forth in (i),
   wherein the expression or activity of said nitrate reductase is deregulated as compared to a control unmodified tobacco plant;
and wherein the deregulated nitrate reductase enzyme comprises:
   (a) a nitrate reductase polypeptide having the sequence of SEQ ID NO:4 and comprising an amino acid substitution at position 523; or
   (b) a nitrate reductase polypeptide having the sequence of SEQ ID NO:4 and comprising an amino acid substitution at position 523, wherein the amino acid at position 523 of SEQ ID NO: 4 is substituted to an aspartic acid,
   wherein said tobacco product has reduced tobacco specific nitrosamine (TSNA) levels compared to a tobacco product derived from a control tobacco plant in which the nitrate reductase enzyme has not been deregulated, wherein total levels of TSNA are reduced by at least 50%.

2. The tobacco product according to claim 1, wherein the deregulated nitrate reductase enzyme is a nitrate reductase enzyme that is constitutively active.

3. The tobacco product according to claim 1, wherein the polynucleotide encoding a deregulated nitrate reductase is a heterologous polynucleotide encoding a modified nitrate reductase polypeptide.

4. The tobacco product according to claim 3, wherein the heterologous polynucleotide is linked to a promoter not natively associated with an endogenous nitrate reductase gene.

5. The tobacco product according to claim 4, wherein the promoter is the Cauliflower Mosaic Virus 35S promoter.

6. The tobacco product according to claim 1, wherein the polynucleotide encoding a deregulated nitrate reductase comprises the polynucleotide sequence of SEQ ID NO: 5.

7. The tobacco product according to claim 1, wherein the polynucleotide encoding a deregulated nitrate reductase is an endogenous nitrate reductase gene that has been modified by a genome editing system or by a mutagen.

8. The tobacco product according to claim 7, wherein the genome editing system comprises an engineered CRISPR/Cas-based system, an engineered Transcription Activator-Like effector nuclease, an engineered zinc finger nuclease, or an engineered meganuclease.

9. The tobacco product according to claim 1, wherein the tobacco is a burley tobacco.

10. The tobacco product of claim 1, wherein the total TSNA level is measured in a leaf from a tobacco plant comprising the tobacco plant cell, wherein
   (a) the leaf is freshly harvested;
   (b) the leaf is cured, stored or processed; or
   (c) the leaf is air-cured.

11. The tobacco product of claim 1, wherein the level of at least one TSNA in the tobacco product is reduced compared to a control level for the at least one TSNA, wherein the at least one TSNA is selected from the group consisting of N-nitrosonornicotine (NNN), 4-(methylnitrosamino)-1-(3-pyridyl)-1-butanone (NNK), N-nitrosoanabasine (NAB), N-nitrosoanatabine (NAT), and combinations thereof.

12. The tobacco product according to claim 1, wherein the TSNA levels are measured in smoke obtained from combustion of leaves of a tobacco plant comprising the tobacco plant cell.

13. The tobacco product according to claim 12, wherein total TSNA levels in smoke are reduced by at least 70%.

14. The tobacco product according to claim 11, wherein the level of NNN is reduced by about 90%.

15. The tobacco product according to claim 11, wherein the level of NNK is reduced by about 66%.

16. The tobacco product according to claim 11, wherein the level of NAB is reduced by about 92%.

17. The tobacco product according to claim 11, wherein the level of NAT is reduced by about 88%.

18. The tobacco product according to claim 1, wherein the tobacco plant cell further comprises a modified nornicotine pathway gene.

19. The tobacco product according to claim 18, wherein the modified nornicotine pathway gene comprises a modified nicotine demethylase gene or cytochrome P450 gene.

20. The tobacco product according to claim 18, wherein the tobacco plant cell comprises a modified CYP82E4 or modified CYP82E10 gene.

21. The tobacco product according to claim 20, wherein the modified CYP82E4 gene or modified CYP82E10 gene are inactivated.

* * * * *